(12) United States Patent
Schecter

(10) Patent No.: US 7,689,283 B1
(45) Date of Patent: Mar. 30, 2010

(54) DIASTOLIC MECHANICAL ALGORITHM FOR OPTIMIZATION OF AV TIMING USING A PLURALITY OF SENSORS

(75) Inventor: Stuart O. Schecter, Great Neck, NY (US)

(73) Assignee: Pacesetter, Inc., Sylmar, CA (US)

(*) Notice: Subject to any disclaimer, the term of this patent is extended or adjusted under 35 U.S.C. 154(b) by 274 days.

(21) Appl. No.: 11/679,030

(22) Filed: Feb. 26, 2007

Related U.S. Application Data

(63) Continuation-in-part of application No. 11/280,715, filed on Nov. 15, 2005.

(60) Provisional application No. 60/627,889, filed on Nov. 15, 2004, provisional application No. 60/634,165, filed on Dec. 8, 2004.

(51) Int. Cl.
*A61N 1/362* (2006.01)
(52) U.S. Cl. ....................................................... 607/18
(58) Field of Classification Search ............. 607/17–18; 600/528
See application file for complete search history.

(56) References Cited

U.S. PATENT DOCUMENTS

| | | | | |
|---|---|---|---|---|
| 5,554,177 | A * | 9/1996 | Kieval et al. | 607/17 |
| 5,836,987 | A * | 11/1998 | Baumann et al. | 607/17 |
| 6,044,298 | A * | 3/2000 | Salo et al. | 607/17 |
| 6,643,548 | B1 * | 11/2003 | Mai et al. | 607/17 |
| 6,792,308 | B2 * | 9/2004 | Corbucci | 607/17 |
| 7,010,347 | B2 | 3/2006 | Schecter | |
| 7,065,400 | B2 | 6/2006 | Schecter | |

* cited by examiner

*Primary Examiner*—Mark W Bockelman
*Assistant Examiner*—Roland Dinga

(57) ABSTRACT

Systems and methods are provided for adjusting atrioventricular timing of a cardiac resynchronization therapy device, based upon multi-modal sensory data. In one particular embodiment, one or more acoustic signals are processed and categorized into certain cardiac-related mechanical events. Impedance waveforms are obtained from implanted electrodes and analyzed to identify certain valvular events. The acoustic and impedance data is analyzed to optimize AV timing and improve cardiac performance.

10 Claims, 35 Drawing Sheets

*** REPRESENTS INTERVAL TIMING W/BEST MEASUREMENT OF CARDIAC PERFORMANCE, LEAST DYSYNCHRONY (OPTIMAL ACOUSTIC WAVE FUNCTION)

|  | SYSTOLIC INTEGRALS OF Z(t)dt | DIASTOLIC INTEGRALS OF Z(t)dt | IDENTIFICATION OF VALVULAR EVENT TIMING / MORPHOLOGY | LINE INTEGRALS OF Z(t)dt |
|---|---|---|---|---|
| MAXIMAL SIGNAL FIDELITY |  |  |  |  |
| INTERMEDIATE SIGNAL FIDELITY | Z (PEAK) | dZ/dt | dZ'/dt | dZ''/dt |
| LEAST SIGNAL FIDELITY | TIME OF ONSET OF Z(t) | TIME OF PEAK dZ/dt | TIME OF Z(PEAK) |  |

FIG. 22

DIASTOLIC MECHANICAL ALGORITHM FOR OPTIMIZATION OF AV TIMING USING A PLURALITY OF SENSORS

RELATED APPLICATIONS

This application is a continuation-in-part of U.S. application Ser. No. 11/280,715, filed Nov. 15, 2005, entitled METHOD AND APPARATUS FOR MONITORING THE HEART BASED ON CARDIAC ACOUSTIC PROPERTIES, which is incorporated herein by reference and which claims priority under 35 U.S.C. §119(e) to:

1) Applicant's U.S. Provisional Patent Application No. 60/627,889, filed Nov. 15, 2004, entitled SONOGRAPHIC SYNCHRONIZATION DETECTOR, which is incorporated herein by reference; and 2) Applicant's U.S. Provisional Patent Application No. 60/634,165, filed Dec. 8, 2004, entitled METHOD AND APPARATUS FOR MONITORING THE HEART BASED ON CARDIAC ACOUSTIC PROPERTIES, which is incorporated herein by reference.

FIELD OF THE DISCLOSURE

The present disclosure relates to implantable cardiac stimulation devices and systems, and more particularly, to such devices and systems that are capable of analyzing cardiac acoustic properties to monitor the condition of the patient's heart and to direct programming of the implanted cardiac stimulation device and system. Such implanted devices and systems are capable of delivering therapy (e.g. cardiac resynchronization) and monitoring the heart based on a plurality of signals and the relationship of such signals to intrinsic cardiac acoustic properties. The cardiac sounds may be detected by an acoustic sensor, such as, for example, a sonomicrometer, which may be a separate unit or which may be contained within the housing unit of the implanted cardiac stimulation device or system.

ACRONYMS

Below is a list of acronyms with their definitions provided as used herein:

| | |
|---|---|
| A2 | Sound Generated By Aortic Valve Closing |
| AD | Analog to Digital Conversion |
| AoVQ | Velocity Information Related to Trans-Aortic Valvular Blood Flow |
| AoVQamp | Aortic Blood Flow Amplitude |
| AoVQTI | Aortic Blood Flow Velocity Time Integral |
| AS | Acoustic Sensor |
| BPF | Band-Pass Filter |
| C | Detected Cardiac Sound |
| CRM | Cardiac Rhythm Management System |
| CRT | Cardiac Resynchronization Therapeutic System |
| D | Implanted Device |
| DFP | Diastolic Filling Phase |
| EDP | Early Diastolic Filling Phase |
| FFT | Fast Fourier Transform |
| GSTI | Global Sonographic Tei Index |
| IEGM | Intracardiac Electrogram |
| IVCT | Isovolumic Contraction Time |
| IVRT | Isovolumic Relaxation Time |
| L | Implanted Lead |
| LCP | Lusitropic Cardiac Performance |
| LDF | Late Diastolic Filling Phase |
| LV | Left Ventricular |
| M1 | Sound Generated By Mitral Valve Closing |
| MB | Megabytes |
| MDQ | Magnitude, Duration and Quality |
| MR | Mitral Regurgitation |
| MRVQ | Mitral Regurgitant Blood Flow |
| MRVQI | Mitral Regurgitant Blood Flow Index |
| P2 | Sound Generated By Pulmonic Valve Closing |
| PV | Pulmonary Vein |
| RV | Right Ventricular |
| S1 | Closing of the Mitral and Tricuspid Valves |
| S2 | Closing of the Aortic and Pulmonic Valves |
| S3 | Extra Cardiac Sounds Indicative of Diastolic Dysfunction During Early Diastolic Filling |
| S4 | Extra Cardiac Sounds Indicative of Diastolic Dysfunction during atrial systole |
| SCP | Systolic Cardiac Performance |
| SEP | Systolic Ejection Phase |
| SLI | Systolic-Lusitropic Index |
| SNR | Signal To Noise Ratio |
| SRI | Strain Rate Imaging |
| SVC-RV | Superior Vena Cava-Right Ventricle |
| T1 | Sound Generated By Tricuspid Valve Closing |
| tAoVc | Time of Aortic Valve Closure |
| Tei Index | a Myocardial Performance index |
| TVI | Tissue Velocity Imaging |
| tPSPI | Time of Post-Systolic Positive Impedance |
| tZ(p) dt | Time of Peak Impedance |
| VE | Valvular Event |
| VQ | Valvular Blood Flow |
| VV | Ventricle-to-Ventricle |
| Z(t) dt | Impedance Waveform |

BACKGROUND

Implantable devices for pacing, cardioversion, defibrillation and resynchronization of cardiac electrical and mechanical function are widely available to prevent and treat symptomatic bradyarrhythmias, tachyarrhythmias and dysynchronous myocardial mechanics. Impaired cardiac performance can result from several abnormalities. Such abnormalities include alterations in the normal electrical conduction patterns and mechanical abnormalities in myocardial contractility. These abnormalities are often (though not necessarily) connected to one another and, as such, electromechanical impairments can cause an impairment in cardiac performance as well. Such impairment in cardiac performance often stems from premature or delayed electrical and/or mechanical events in different cardiac chambers and within specific cardiac chambers. For example, conduction abnormalities may occur between the atria and the ventricular chambers, which are known as atrial-ventricular dysynchrony. Abnormalities between right and left ventricular chambers (inter-ventricular) or within the right or left ventricles (intra-ventricular) can result in dysynchrony as well. Dysynchrony leads to ineffective work as a result of forces being generated in specific regions at inappropriate times relative to the opening and closing of the heart valves. It can lead to myocardial relaxation during times where the generation of force in all myocardial segments should be occurring synchronously and in a symmetric fashion in relation to valvular events and myocardial thickening when all myocardial segments should be relaxing, diastole, and receiving oxygenated blood from the lungs. Multiple variations in the location and pattern of dysynchrony may exist in individual patients.

Methodologies exist for optimizing the timing of pacing impulses in such systems including extrinsic measurements using echocardiography and intrinsic methodologies described by the inventor and others. Intrinsic or closed loop systems for monitoring purposes and optimizing interval timing within such implanted devices are in development.

These systems may employ measurements of cardiac performance and indices of dysynchrony. Several methodologies have been proposed including pressure transducers, oxygen saturation sensors, ultrasonic dimension sensors, accelerometers, measurements of electrical activation patterns and impedance based measurements. Such technologies may require large lead bodies, multiple transducers and can place significant energy demands secondary to signal processing. The present disclosure employs an acoustic sensor, such as a sonomicrometer, that detects intrinsic cardiac sound and characterizes a wide range of acoustic properties including but not limited to intensity, frequency, duration and self-similarity. The system then relates this acoustic data to other sensed signals, such as intracardiac electrograms and impedance waveforms, to optimize timing of pacing impulses and to provide data for monitoring and diagnostic purposes.

References that relate to the present disclosure include the following U.S. patents and published patent applications, each of which is incorporated herein by reference: U.S. Pat. No. 6,804,559, "Electromedical Implant," issued Oct. 12, 2004 to Kraus et al.; U.S. Pat. No. 6,795,732, "Implantable Medical Device Employing Sonomicrometer Output Signals for Detection and Measurement of Cardiac Mechanical Function," issued Sep. 21, 2004 to Stadler et al.; U.S. Pat. No. 6,792,308, "Myocardial Performance Assessment," issued Sep. 14, 2004 to Corbucci; U.S. Pat. No. 6,816,301, "Microelectromechanical Devices and Methods of Manufacture," issued Nov. 9, 2004 to Schiller; U.S. Pat. No. 6,572,560, "Multi-Modal Cardiac Diagnostic Decision Support System and Method," issued Jun. 3, 2003; U.S. published patent application number 20040176810A1, "Implantable Medical Device Employing Sonomicrometer Output Signals for Detection and Measurement of Cardiac Mechanical Function," published Sep. 9, 2004 to Stadler et al.; and U.S. published patent application number 20030083702, "Implantable Medical Device Employing Sonomicrometer Output Signals for Detection and Measurement of Cardiac Mechanical Function," published May 1, 2003 to Stadler et al.

SUMMARY

Described herein is a system and method capable of detecting wide frequency range, variable amplitude cardiac acoustic waveforms with minimal extraneous noise. The disclosed acoustic sensing and monitoring system may be incorporated within an implanted unit or used as external monitoring equipment capable of interfacing with implanted cardiac rhythm management devices. The derived acoustic signal is digitally processed and categorized into major and minor sounds. The digital processing may be performed by fast Fourier transform analysis, wavelet decomposition or other techniques. The major sounds are extracted and classified as being related to the opening or closing of the heart valves or related to blood flow through the heart valves. The major acoustical data is used for formulation of a temporal framework and calculation of an index of cardiac performance related to the timing of valvular events, the amplitude of sound generated during the systolic ejection phase and the duration of the various components of the cardiac cycle. Temporal data is related to the intracardiac electrogram for reference purposes and other applications such as timing of events during analysis of impedance signals. The major acoustical data is also used for assessment of valvular function. The minor sounds relate to the remaining signal after subtraction of the major acoustical waveforms. The system analyzes this data and derives a function which quantifies the degree of synchronous wall motion. The mathematical descriptors which are used to derive this function are generated by techniques which include but are not limited to fractal analysis. The resulting data is then compared to labeled examples stored within the template data bank of the system. The labeled examples may be derived from population studies as well as from the patient where such template data is stored during analysis of acoustic properties while other diagnostic information is being acquired. Neural networks or other means for creating a diagnostic scale related to the pathophysiologic findings detected by the system will generate a numerical and audio-visual display conveying relevant data to the clinician in a user friendly format.

In certain embodiments, data obtained from cardiac acoustic sensors are used synergistically with data obtained from other sensor modalities to optimize the function of implanted cardiac rhythm management devices. In one embodiment, an implanted cardiac rhythm management device acquires both acoustic and impedance data from implanted sensors to generate a more robust profile of valvular and other mechanical events in the cardiac cycle. This profile is analyzed and used to automatically adjust the interval timing in a multi-site pacing system and improve hemodynamic performance of the heart.

BRIEF DESCRIPTION OF THE DRAWINGS

Further feature and advantages of the present disclosure may be more readily understood by reference to the following description, taken in conjunction with the accompanying drawings, in which:

FIG. 22 is a table describing varying degrees of impedance signal fidelity requirements.

FIG. 26b illustrates the functioning of the Automatic Optimization Algorithm (AOA) with parameters descriptive of dysynchrony (and not cardiac performance) which are of less fidelity than those of GCP shown in FIG. 26a.

DETAILED DESCRIPTION

Phonocardiography has been employed as a diagnostic tool for evaluation of cardiac function for over a century. Methods of detecting intrinsic cardiac sounds using stethoscopes or complex medical equipment such as echocardiography machines are employed in cardiology practices. Techniques for evaluating cardiac acoustic signals and analyzing such signals with multi-resolution signal analysis, such as wavelet decomposition to extract time-frequency data and using methods such as neural network applications for identification of the heart sounds, have also been described. (See, for example the following references, each of which is incorporated herein by reference: Barschdorff et al. Automatic Phonocardiogram Signal Analysis in Infants based on Wavelet Transforms and Artificial Neural Networks, Computers in Cardiology 1995, Vienna Austria, Sep. 10-13, 1995, pp. 753-756; Edwards et al., Neural Network and Conventional Classifiers to Distinguish Between First and Second Heart Sounds, IEE Colloquium on Artificial Intelligence Methods for Biomedical Data Processing, London, UK, Apr. 26, 1996, pp 1-3; and H. F. V. Boshoff, A Fast Box Counting Algorithm for Determining the Fractal Dimension of Sampled Continuous Functions, Communications and Signal Processing, 1992. COMSIG '92, Proceedings of the 1992 South African Symposium on, 11 Sep. 1992, Pages 43-48.) Such methodologies can be used to assess cardiac performance and quantify dysynchrony for both monitoring purposes and for directing programming of interval timing in implanted cardiac stimulation systems.

Major Sounds

Figure 1:
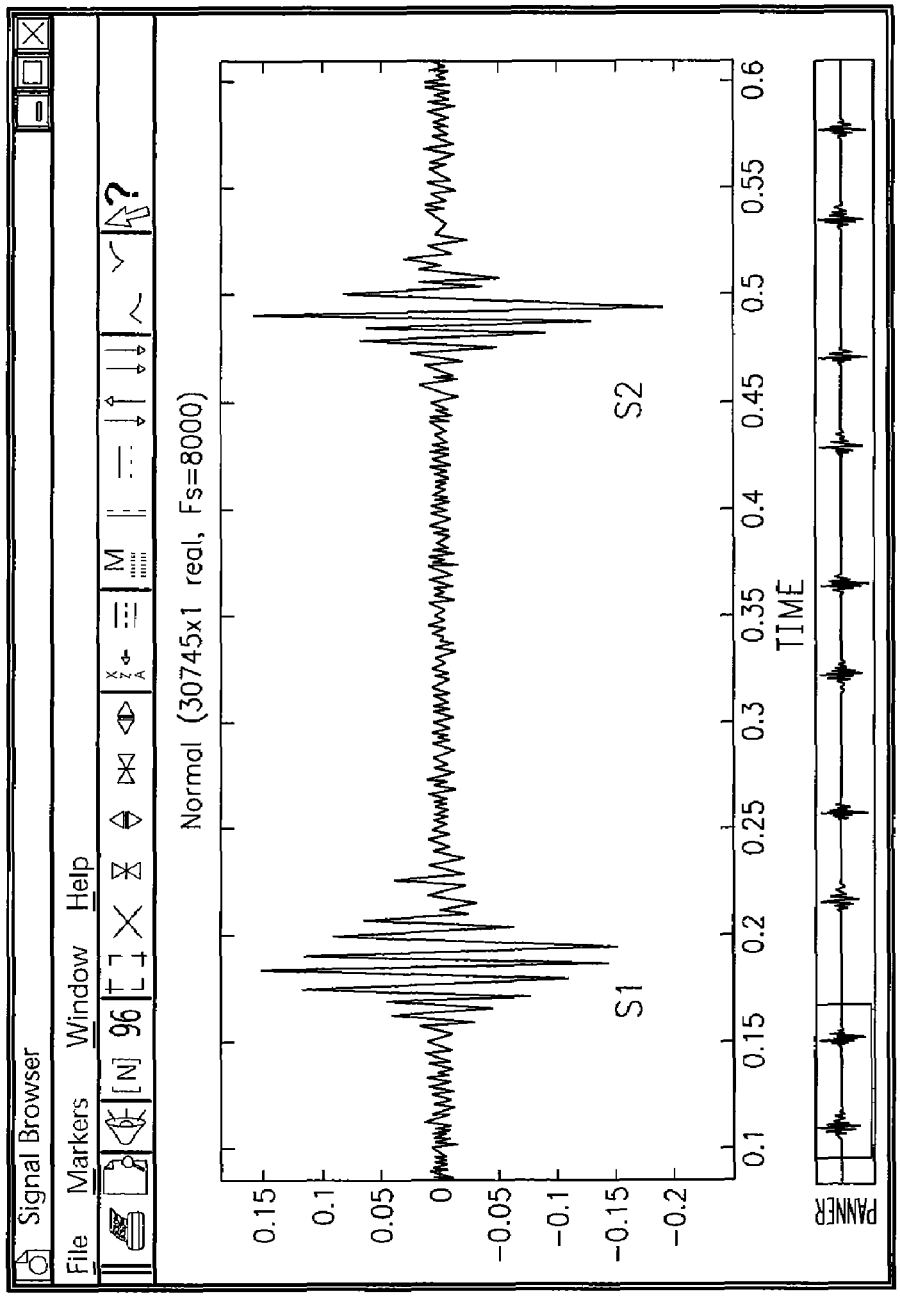
FIG. 1 depicts high amplitude cardiac sounds S1 and S2.

Valvular Events. The highest amplitude physiologically normal heart sounds are denoted as S1 and S2 (FIG. 1) and correspond to the closing of the heart valves, valvular events (VEs). These sounds are comprised of short-lived or discrete, higher frequency events related to the mitral, tricuspid (first heart sounds) and aortic, pulmonic valves (second heart sounds). The timing and amplitude of these sounds relate to cardiac electro-mechanical events and cardiac performance. Changes in the timing, frequency, and amplitudes of these sounds can occur as a result of a variety of factors including normal respiration and pathologic states. Lower frequency sounds related to blood flow within the cardiac chambers and through the valves can also be detected. Extra, high frequency, short-lived sounds (S3, S4) and pathologic sounds that relate to regurgitant or stenotic valves can be detected in a variety of conditions. The details of these relationships can be found in any cardiology textbook.

Figure 2A:
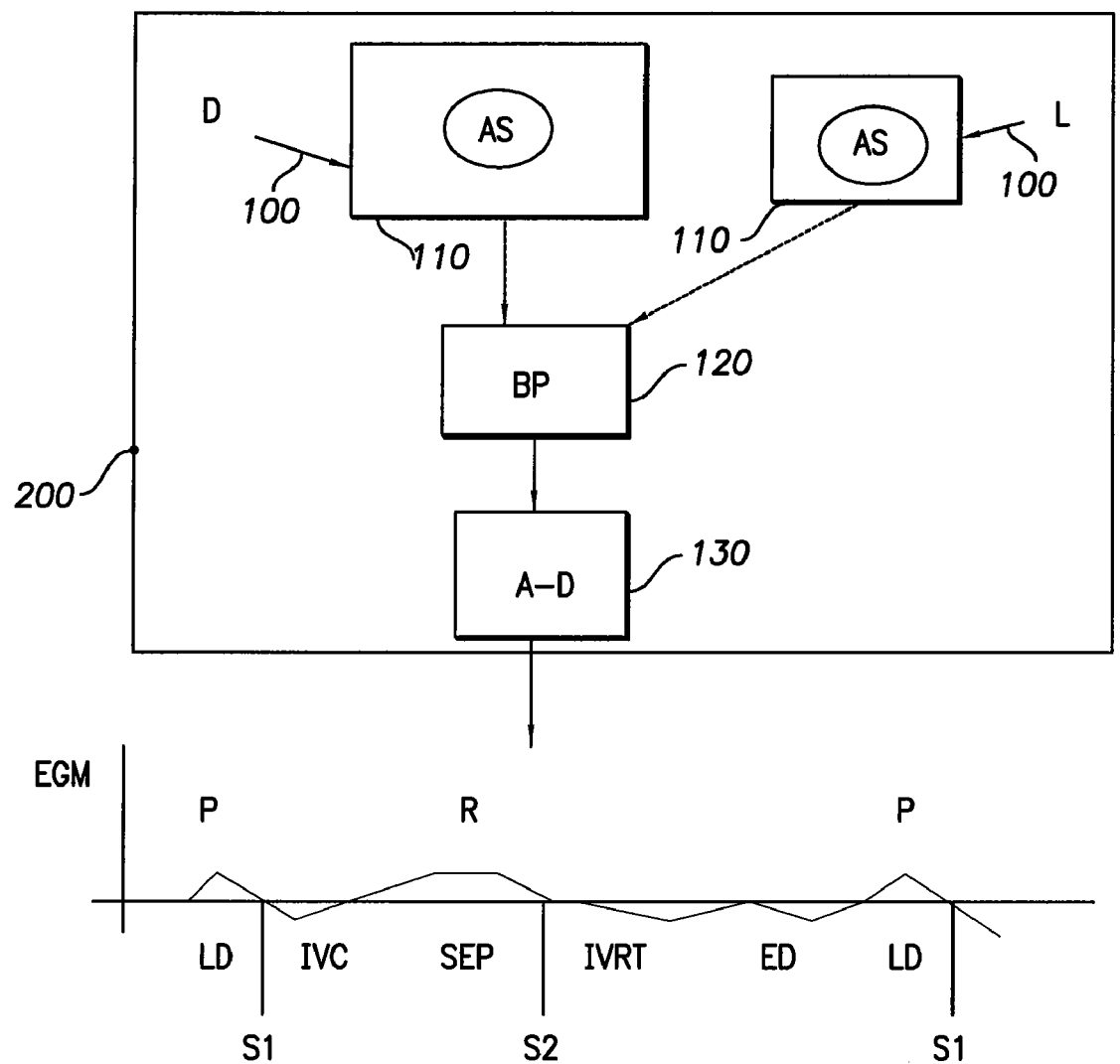
FIG. 2a is a block diagram of the disclosed acoustic monitoring system and how it relates to various components of the intracardiac electrogram.

In FIG. 2a, an implanted acoustic sensor, AS, is used to capture the cardiac sounds in audible and inaudible frequency ranges (step 100). The acoustic sensor, AS, may be part of the hardware in the implanted device, D, in a lead system, L, or a separate unit that may rest on the outside surface of the chest similar to a conventional stethoscope. The lead system may be part of conventional implanted device leads or a separately unit that may be implanted, for example, within the subcutaneous tissues. The received analog acoustic signals are then transmitted (dotted arrows, step 110) and processed using band-pass filtration (BPF) whereby extraneous sounds such as those related to the outside environment, respiration and sensor movement are eliminated (step 120). Determination of times where such extraneous signals are not present using a plurality of sensors is used for determination of time for periodic interval monitoring or algorithm activation as described below. By way of example, such sensors can include accelerometers or respirometers using thoracic impedance data as well as an implanted acoustic sensor such as a sonomicrometer.

Referring to FIG. 2a, Analog-to-digital conversion (AD) of the acquired sonographic data is then implemented (step 130). Alternatively, AD conversion may occur prior to band-pass filtration. The methodologies and technologies required to perform steps 100, 110, 120 and 130 are described in prior disclosures and can be manufactured by those experienced in the art. The acoustic sensor, AS, can be located either in the housing portion (or can) of the device, D, or within a lead system, L, or as a separate transducer. More than one acoustic sensor can be used.

By referencing the temporal relationships of the detected sound to intracardiac electrogram (IEGM) signals, the sounds emitted from the heart can be identified and labeled as the major heart sounds, M1, T1, A2, P2 (mitral, tricuspid, aortic and pulmonic valve closure, respectively). S1 is comprised of M1 and T1. S2 is comprised of A2 and P2. A2 and P2 may differ by tens of milliseconds in time, and this differential (tP2−tA2) may be used for diagnostic purposes, such as, for example, pulmonary hypertension.

The timing of the heart sounds can be referenced to other acquired data such as impedance signals using the intracardiac electrogram as a central signal.

Specific sounds related to time of valve opening may be detected as well. FIG. 2a depicts how such an analysis and referencing to the electrogram can be performed (timing of valve opening not depicted for simplicity purposes but may be employed in current disclosure). Accordingly, it is possible to derive from these major heart sounds the timing of valvular events and the duration of various components of the cardiac cycle within the confines of the sound filtration and digital conversion system, 200. These components are the isovolumic relaxation time (IVRT), isovolumic contraction time (IVCT), systolic ejection phase (SEP) and diastolic filling phase (DFP). The DFP can be further subdivided into the early (EDF) and late diastolic (LDF) filling phases.

During these intervals, specific sounds can be detected related to blood flow through the cardiac valves and chambers. Using conventional echocardiographic techniques one can sample ultrasonographic data from specific regions of interest using pulsed and continuous wave Doppler. The present embodiment may analyze the full spectrum of sound, (audible and inaudible frequency range) and is not specific to any particular location. Furthermore, ultrasound techniques implement active sound reflected back to an ultrasound emitting transducer, wherein the current disclosure detects sound passively.

In an alternate embodiment, multiple acoustic sensors AS can be used which are capable of detecting local or regional sounds and making comparisons of such regional sound data (e.g. with FFT) for analysis and optimization of pacing interval timing either within the implanted device system or through external monitoring equipment. By these means, multi-dimensional (e.g. three dimensional space as a function of time) representation of acoustic events may be derived.

Temporally Derived Cardiac Performance Index. Once the time sequences of the major components of the cardiac cycle have been derived, data related to cardiac performance can be calculated. The Tei index or myocardial performance index, which measures the relationship of specific systolic and diastolic time frames determined with echocardiography, has been shown to correlate with cardiac performance.

The inventor has derived an index, Global Sonographic Tei Index (GSTI), which can be calculated from initial major heart sound temporal data and be used for monitoring purposes or closed loop programming of interval timing in a multi-site pacing system. The GSTI is defined in Equation 1, below:

$$\text{GSTI}=(IVC+IVRT)/SEP \qquad \text{Equation 1}$$

Regional acoustic sensor Tei indices related to local wall motion can be obtained and used for analysis of dysynchrony in systems with more than one implanted acoustic sensor AS (e.g. right ventricular AS and left ventricular AS). Ultrasound techniques using Doppler tissue echocardiography measurements of segmental myocardial performance demonstrate this physiology. See, e.g., "Evaluation of Ventricular Synchrony Using Novel Doppler Echocardiographic Indices in Patients with heart Failure Receiving Cardiac Resynchronization Therapy," Sun, J. P., Chinchoy, E., Donal, E., et. al., J. Am Soc Echo; 17, 2004, 845-850, which is incorporated herein by reference. Data comparing the right ventricular acoustic sensor and left ventricular acoustic sensor can be used to diagnose dysynchrony and to direct interval timing in a cardiac resynchronization therapeutic device.

Derivation of the GSTI represents a simplification of such process because it requires less sophisticated signal processing than a system required for analysis of a wider spectrum of frequencies which relate to minor sounds such as those reflective of valvular function (e.g. intensity of mitral regurgitation) and characterization of the reverberation of pathologically dysynchronous myocardial segments. Once this initial simplified process is complete, the temporal information can be referenced to the IEGM signal and used for delineation of valvular events and intervals of the cardiac cycle with identification the systolic and diastolic phases of the cardiac cycle (FIGS. 2a and 2b) and calculation of the GSTI. This can then serve as a framework template for more complex analyses of minor sounds as described below.

Figure 2B:
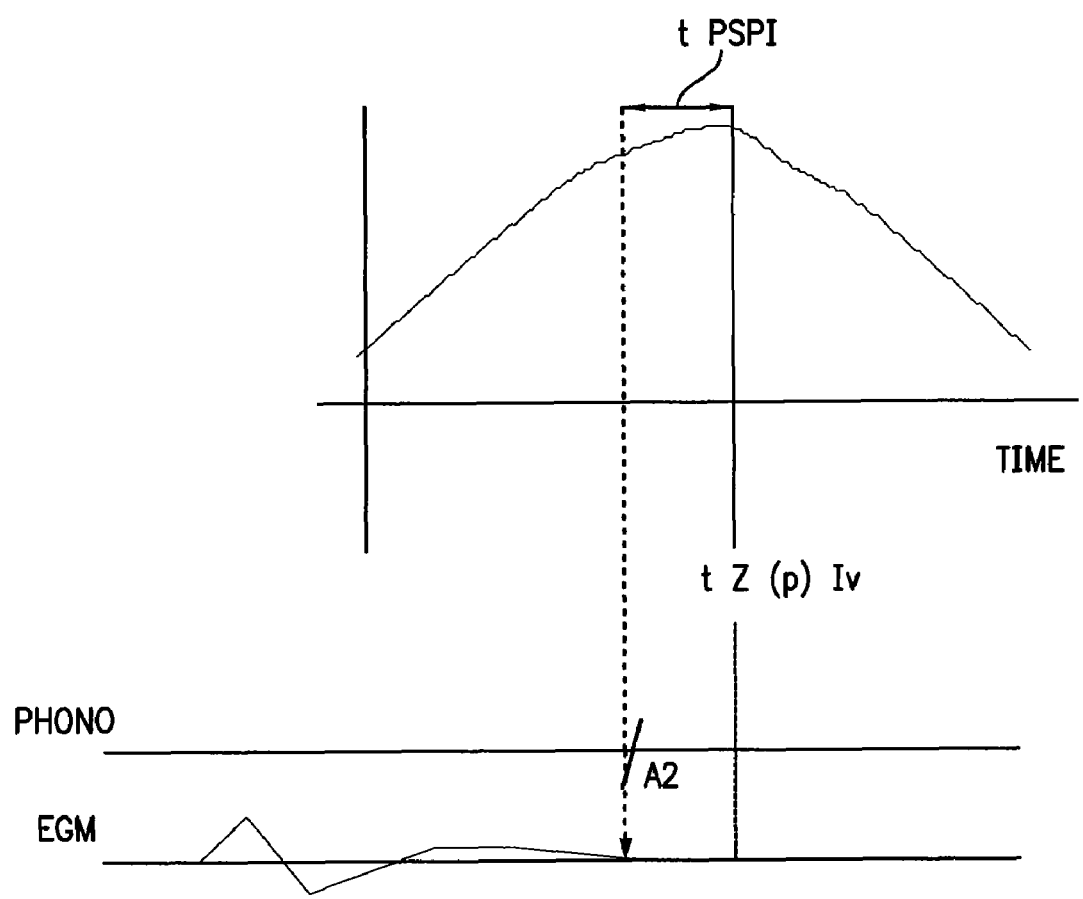
FIG. 2b illustrates how calculation of the time of post-systolic myocardial contractility, derived from impedance data acquired from a left ventricular (LV) lead, will allow for a cardiac resynchronization therapeutic device (CRT) to pre-excite this region by an appropriate time frame to eliminate post-systolic contractility and to resynchronize the heart.

Alternate Applications Using Temporal Data. Once timing of valvular events is referenced to the intracardiac electrogram signal, alternate measurements such as impedance can be evaluated in the context of this temporal framework. The measurement and assessment of cardiac impedance data is described in U.S. Pat. No. 7,010,347 and U.S. Pat. No. 7,065,400, both of which are herein incorporated by reference. By way of example, impedance signals may be used to determine cardiac performance and degree of electromechanical dysynchrony. It may be difficult to reference the various temporal relationships of the impedance signals to valvular events. Implementation of sonographic data (e.g. S1 and S2) will allow for accurate determination of aortic and mitral valve closure. Detection of myocardial contractility based on impedance waveforms obtained from laterally located left ventricular electrodes after the time of aortic valve closure, tAoVc, defined by the sonographic synchronization detector will indicate dysynchrony. Calculation of the time of post-systolic myocardial contractility derived from impedance data acquired from a left ventricular (LV) lead will allow for a cardiac resynchronization therapeutic device (CRT) to pre-excite this region by an appropriate time frame as to eliminate post-systolic contractility and resynchronize the heart (FIG. 2b). In this embodiment, LV impedance waveforms are derived, but the precise time of aortic valve closure, tAoVc, cannot be discerned using impedance data alone. The A2 detected by the acoustic sensor, AS, defines the tAoVc. Analysis of LV impedance waveform, Z (t) dt, and identification of time of peak impedance, tZ(p)lv in this vector, will allow for calculation of the time of post-systolic positive impedance, tPSPI. Pre-excitation of the LV lead so as to cause the post-systolic positive impedance time, tPSPI, to be equal or less than zero will help synchronize timing of contractility. Methods for correlating cardiac acoustic information and cardiac impedance data to provide more accurate timing data for mechanical events of the cardiac cycle are described in greater detail below.

Magnitude, Duration, Quality. The quantity and quality of the derived cardiac acoustic data can be described in a number of ways. The features of the sound will be referred to herein as the Magnitude, Duration and Quality (MDQ), though other descriptors may be used as well. The magnitude relates to the amplitude or power of specific frequencies (which may be a function of time) and, by way of example and for illustrative purposes, can be represented with power spectra. The duration of any acoustic data that has a specific frequency or frequency range relates to temporal data and can be quantified as well. Acoustic quality will have a number of features and will require more complex analyses. Methods such as wavelet decomposition and application of neural networks will allow for mathematical descriptors that define the quality of the sound by analysis of digitally processed acoustic waveforms. Non-linear mathematical descriptors that relate to the degree of chaos are another example of methodology that can be used for characterizing cardiac acoustic properties. Such signal processing will be described after a review of the factors that are responsible for the generation of cardiac acoustics. This digitally processed data or information will be referred to as the acoustic wave function, regardless of the mathematical methodology employed for describing such data.

Valvular blood flow. Sounds related to valvular blood flow will also constitute major sound. Such sounds, because of amplitude and duration may lead to difficulties in acquisition of more minor sounds to be described below. As blood flows through the valves, primarily during time frames where the valves are open and not upon opening and closing, temporal processing and delineation of a framework for reference will differentiate the major heart sounds related to valvular events from those related to valvular blood flow, VQ.

The amplitude, tone, frequency, decay etc. (referred to herein as magnitude, duration and quality, MDQ) of sound related to valvular blood flow, VQ, will vary between individuals and within the same individual under varying circumstances. Respiration, patient position, adrenergic tone will modify the magnitude, quality and duration of valvular blood flow, VQ. As mentioned above, analysis of all sounds including VQ is performed when a plurality of sensors indicate a specific patient state (e.g. resting, relative hypopnea/apnea, minimal extraneous sound, supine position). VQ will be initially removed from the framework analysis. By way of example, Fourier analysis techniques, such as Fast Fourier Transforms (FFT), in both frequency and time domains can be implemented to identify valvular blood flow, VQ, and differentiate sounds related to valvular events, VE, and valvular blood flow, VQ, as well as other minor sounds related to wall motion or reverberation described below. Valvular event sounds will in general be more discrete, sharp and of higher magnitude and frequency than valvular blood flow or other minor sounds related to myocardial motion. Accordingly, the power spectra for VE sounds will be different than that for VQ. The duration of VQ will be longer than that for VE. Thus, VE can be differentiated from VQ by any number of methods including but not limited to those described herein.

One measure of valvular blood flow, VQ, that may be analyzed is the magnitude, duration and quality (MDQ) of the mitral regurgitant blood flow. The MDQ associated with less mitral regurgitation, MR, will be found in patients with less significant pathologic states. The MR sound is usually within the audible frequency range. The MDQ with both stenotic and regurgitant VQ can be analyzed using this technology, though MR is used herein by way of example.

Cardiac Resynchronization Therapy devices (CRT) are implanted in patients with cardiomyopathy and dysynchronous electromechanical myocardial properties. CRT has been demonstrated to reduce the severity of mitral regurgitation, MR, in a number of clinical trials published in the cardiology literature. Optimization of CRT interval timing (temporal relationship between current delivery of pacing impulses delivered to the atria and ventricles in a multi-site pacing system) can further minimize MR. The disclosed system can characterize the MR audio signals with MDQ analysis at varying interval timing as part of a closed loop system and direct programming of ideal interval timing as described in Applicant's previously cited pending patent applications and herein.

Figure 3:
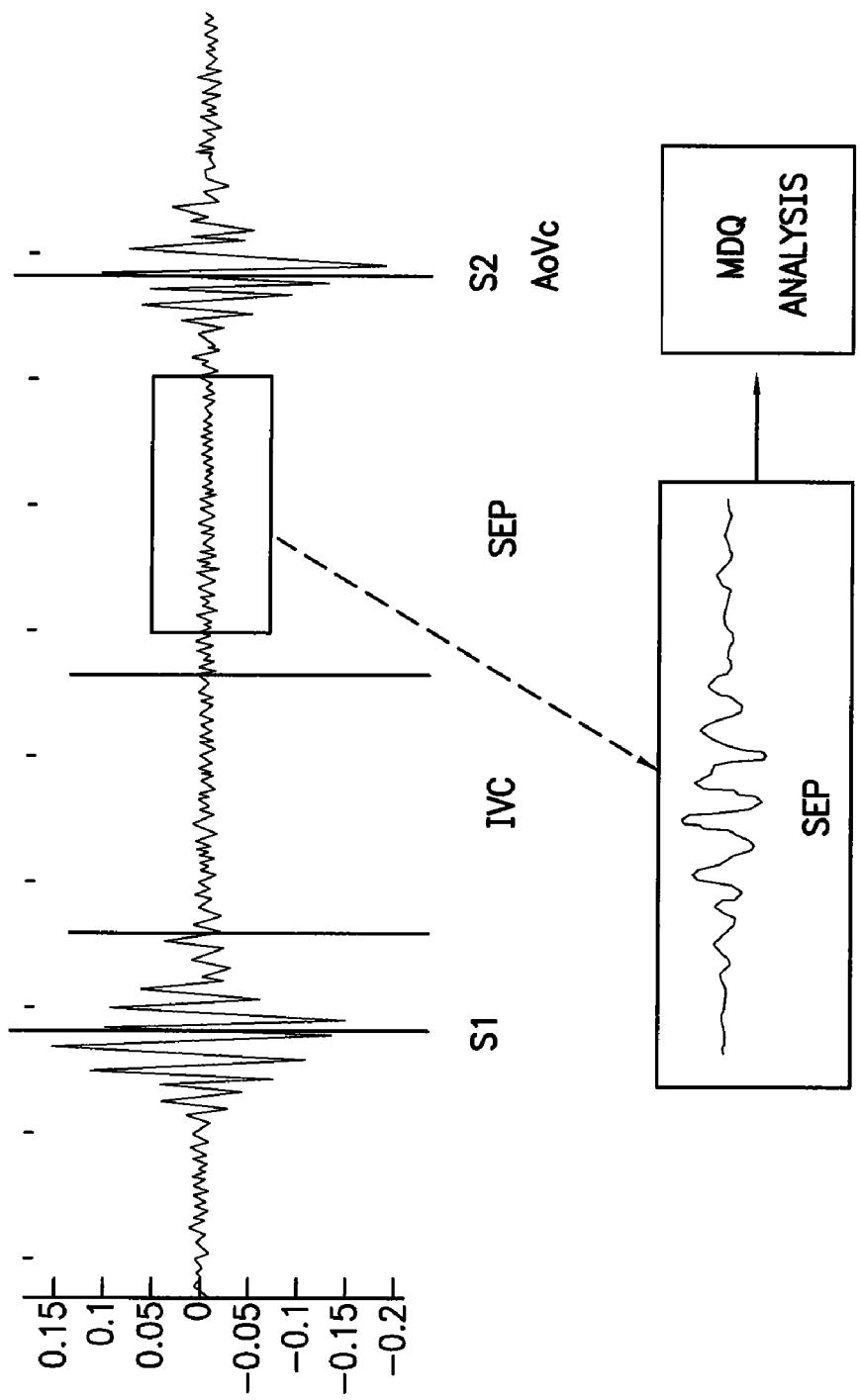
FIG. 3 illustrates how the frequency range, amplitude and other characteristics of sound detected during the systolic ejection phase (SEP) can be analyzed as to define whether valvular blood flow (VQ) is normal or pathologic.

Some of the major sounds related to VQ may also be inaudible or difficult to detect. The duration of other related sounds can be used for referencing the time of valve opening to the electrogram signal or impedance waveform. For example, the sounds related to valvular opening may be more subtle than those related to valve closure. Thus, when the sound related to trans-aortic blood flow begins at the initial portion of the systolic ejection phase (SEP), the system will recognize this as being the time of aortic valve opening. The VQ related to trans-aortic valve blood flow is of importance for other reasons. In the pathologic state where there is aortic stenosis (systolic murmur) or aortic regurgitation (diastolic murmur), this sound will often fall into the audible range. With greater disease severity, the amplitude of these sounds will be increased. Under conditions of advanced stenosis of the aortic valve and impaired cardiac performance, the MDQ will change and the amplitude will decrease. Thus, the amplitude of VQ during the SEP may be bimodal over time in patients who develop progressive aortic stenosis with progressive impairments in cardiac performance or stroke volume. Thus, the frequency range, amplitude and other characteristics of sound detected during the systolic ejection phase can be analyzed as to define whether VQ is normal or pathologic (FIG. 3).

In circumstances where no significant valvular pathology exists, the sound related to trans-aortic valve blood flow will be inaudible. Detection of the sound during the SEP in the inaudible range can be used to determine cardiac performance, while detection of the sound in the audible range can be used to determine disease severity. As way of example, higher amplitude, inaudible sound during the SEP will be detected under conditions of higher stroke volume, whereas higher amplitude, audible sound during the SEP will signify more severe aortic stenosis or mitral regurgitation. The power spectra and composite frequencies detected will help differentiate whether or not the MDQ is consistent with aortic or mitral VQ, as well as identify circumstances where aortic stenosis is severe despite a progressive reduction in amplitude of aortic VQ during the SEP. Thus, the system will analyze and differentiate between sounds with variable frequency ranges and amplitudes. The process of differentiation can implement labeled examples that are stored as template data within the system, as discussed below.

AoVQ Cardiac Performance Index. Velocity information related to trans-aortic valvular blood flow (AoVQ) is used in echocardiographic assessments as a means of calculating stroke volume. Time integration of AoVQ, aortic velocity time integral (AoVTI), derives stroke volume. A directly proportional relationship to the amplitude of detected sound (though inaudible) during the SEP to AoVTI can be expected. This relationship need not be linear.

Figure 4:
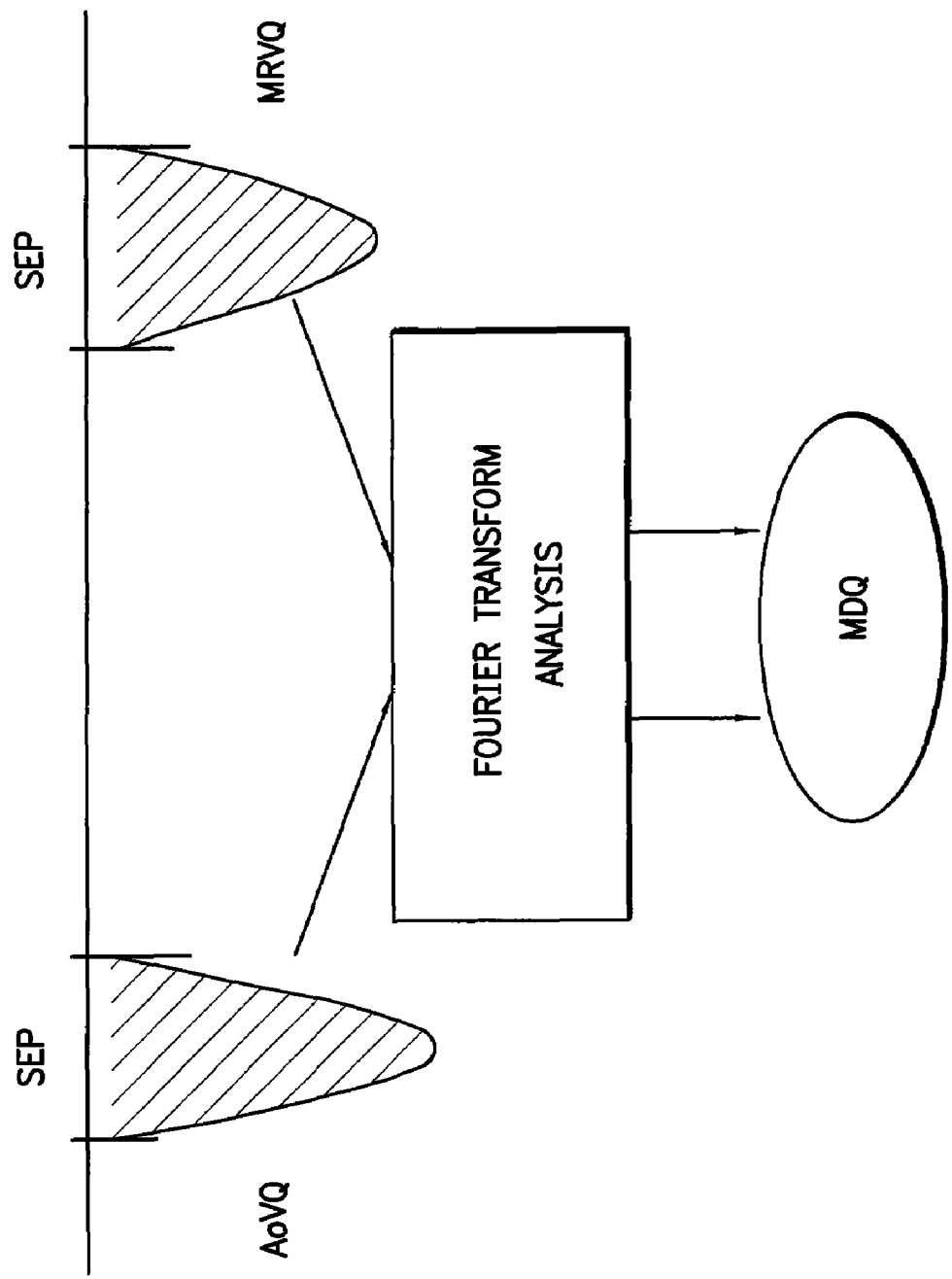
FIG. 4 illustrates one means for performing magnitude, duration and quality (MDQ) analysis with Fast Fourier Transform analysis in the frequency domain.
Figure 5:
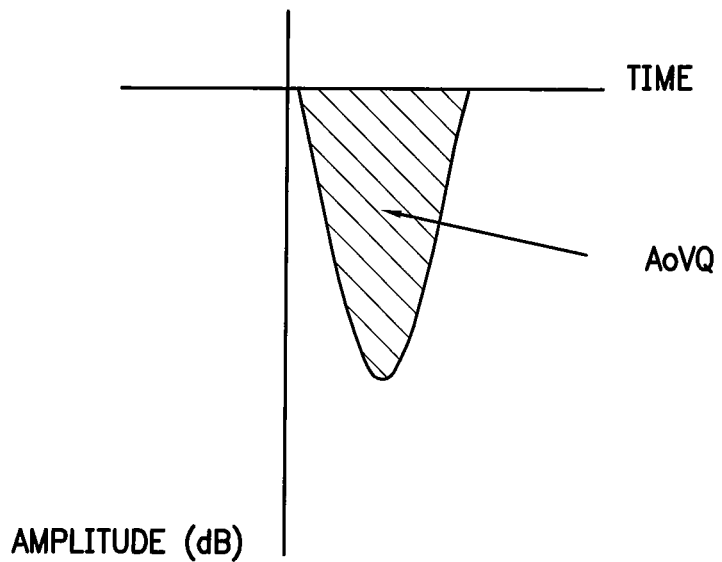
FIG. 5 illustrates how information related to the duration and amplitude of Trans-Aortic Valvular Blood Flow (AoVQ) can be used for measuring cardiac performance.

MDQ analysis of the MR sound and AoVQ is used in the disclosed system for differentiation of these sounds as they occur during similar time frames of the SEP. One means for performing MDQ analysis is with Fast Fourier Transform analysis in the frequency domain, as illustrated in FIG. 4. The importance of differentiation of trans-aortic valvular blood flow (AoVQ) and mitral regurgitant valve closure (MRVQ) is vital as in the non-pathologic state, the higher the amplitude of AoVQ the better the clinical status of the patient, while the higher the amplitude of MRVQ, the greater mitral valvular regurgitation may be present. AoVQ during the SEP can be used to identify the duration of the SEP (as can identification of the time difference between aortic valve opening, AoVo, and AoVc). Referring to equation 1, the duration of the SEP is indirectly proportional to the Tei index. Thus, information related to the duration and amplitude of AoVQ, AoVQ amplitude time integral can be used for measuring cardiac performance, as illustrated in FIG. 5. Such acoustic measurements will be less subject to the inter-observer and intra-observer variability described with ultrasonic pulse-waved Doppler data derived with conventional echocardiography, as the acoustic data will not be subject to errors from changes in the location of the insonified region.

Figure 6:
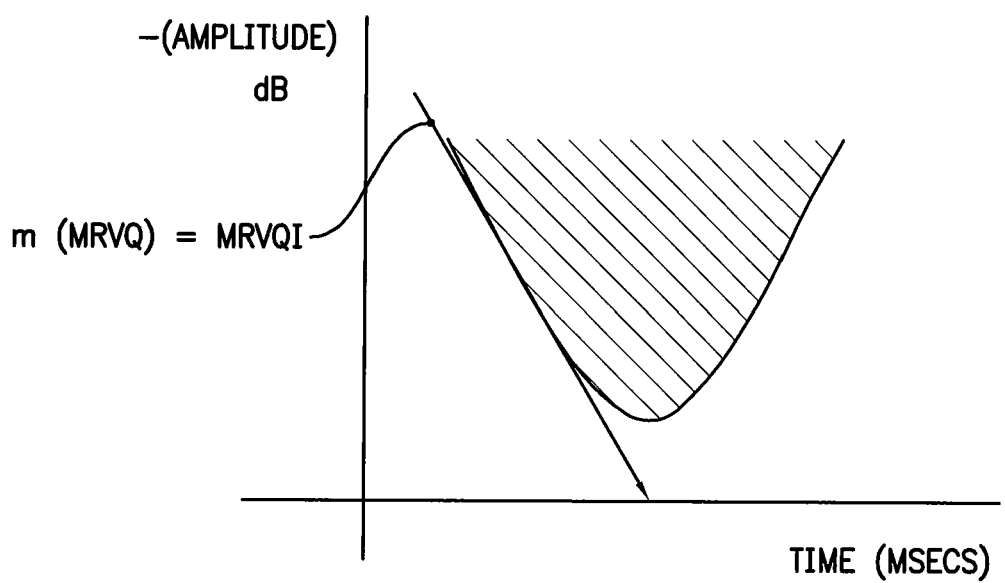
FIG. 6 illustrates how the Mitral Regurgitant Blood Flow Index is determined.

MRVQ Cardiac Performance Index. An alternate method for evaluating cardiac performance is with derivation of the slope of the acoustical envelope related to MR. The amplitude of the MRVQ (whether in an audible or inaudible frequency or amplitude range) is related to the changes in pressure between the left ventricle and the left atrium (LA). The rate of change of pressure within these two chambers during the initial portion of the SEP (MR dP/dt) has been established to serve as a means for quantifying cardiac performance. Similarly, cardiac performance may be derived by evaluation of the slope of the amplitude of MRVQ during the initial portion of the SEP as depicted in FIG. 6. An MR jet derived from pulsed wave Doppler technique derives MR dP/dt. Generally, the clinician will evaluate the slope between 1 and 3 cm/second. A modification of the Bernoulli equation relates dP/dt to the Doppler derived change in velocity, as follows:

$$\text{Pressure} = 4 * V^2 \qquad \text{Equation 2}$$

where V is the Doppler derived velocity

The detail of the derivation can be found in textbooks on echocardiography and fluid dynamics.

The cardiac performance index related to dP/dt between pressure gradient (LV to LA) values of 4 and 36 mm/Hg (conventional methodology) is proportionate to cardiac performance. The MRVQ cardiac performance index (MRVQI) may be derived in a similar fashion. The envelope of the MRVQ waveform can be used in a similar fashion. The slope, m, of the maxima of the acoustical envelope over time will be proportional to MR dP/dt as MRVQ is generated as a function of MR dP/dt, which is illustrated in FIG. 6. The slope can be derived from between the onset of the MR jet and peak of MRVQ acoustical envelope maxima. The slope may be derived between alternate points along the envelope. It should be noted that trace or mild regurgitation detectable with pulsed wave Doppler in the immediate vicinity of the mitral valve occurs in otherwise normal individuals. Thus, an audible signal may be detected in patients without significant MR and used for measurements of cardiac performance as well.

Importantly, comparisons of acoustic parameters need to be applied within a given individual as the amplitude of audible sound in one individual will not necessarily correlate with disease severity when compared to another individual. For example, one patient may have a loud murmur related to MR and have less severe MR than another individual. This can be best understood by considering basic acoustic and fluid dynamic principles. The volume of regurgitant blood flow through a larger orifice may be greater but generate less sound, while the volume of MR through a smaller orifice may be less and generate more sound as a result of multiple factors related to fluid dynamics (e.g. velocity, direction of flow, turbulence, less laminar flow). However, once the sound is characterized in a given individual as a certain degree of MR, increases in the amplitude of MRVQ will be expected as the severity of MR increases.

In broad terms, the disclosed system is capable of differentiating sounds related to different VQ using MDQ analysis, and thus intra-individual comparisons can be made for defining severity of the pathologic state and level of cardiac performance at different times.

Minor Sounds

More complex sounds, minor sounds, related to myocardial motion may also be appreciated with sensitive acoustic sensing, or sonomicrometry, in addition to the major sounds. Such sounds will generally be in an inaudible range. Minor sounds within the audible range related to pathologic states have been defined. The presence of a third or fourth heart sound (S3, S4) may indicate abnormalities in the compliance of the heart and diastolic dysfunction. An S3 or S4 that is inaudible may also be detected by the system disclosed herein. Elimination of S3 and S4 with resynchronization therapy will indicate improvements in diastolic function that relate to a mitigation of delayed myocardial motion and/or contractility after aortic valve closure.

Detection of either audible or inaudible third and fourth heart sounds can be used for monitoring purposes. More complex minor sound that have a spectrum of lower amplitudes and, multiple frequencies may be detected. These minor sounds relate to wall motion and the relative timing of wall motion and reverberation effects.

Myocardial Segment Reverberation. Heterogeneity of regional myocardial motion will cause differing signal intensities and pathologic frequency spectra than globally homogeneous wall motion. Fractionated, chaotic sound will result from circumstances where there is disorganized electromechanical activation, while more homogeneous tones and frequencies will result in the normal synchronous state. One acoustic sensor can be implemented for identifying more organized, synchronous tones and frequencies in a global fashion.

In order to understand how such sounds are generated, we will briefly discuss a developing technology in the field of ultrasound. Sound is a result of vibration. The cardiac chambers are formed by heart muscle, or myocardium, and other tissues that comprise the outer borders of the cardiac chambers. This tissue has motion during the cardiac cycle and thus generates sound. The cardiac chambers themselves play a role in determining the MDQ of generated sound.

Recent advances in echocardiography have allowed for more accurate quantification of tissue motion and deformation. For the purposes of this discussion, we will refer to this as Tissue Velocity Imaging (TVI) and Strain Rate Imaging (SRI), respectively. Doppler echocardiographic assessment at high frame rates with minimal temporal averaging can accurately identify these myocardial properties. Such an assessment is available in currently manufactured echocardiography equipment (e.g. equipment manufactured by General Electric). Analysis of these properties has allowed for identification of a number of disease processes. For the purposes of discussion and by way of example we will focus on the use of this technology for identification of dysynchronous electromechanical events in patients who stand to benefit from CRT implantation.

Longitudinal Myocardial Motion. Normal electromechanical activation patterns can be identified by evaluation of tissue velocity time graphs generated using such Doppler echocardiographic techniques. TVI in a longitudinal plane delineates a specific velocity time graph in a normal individual. Movement of the base of the heart toward the apex occurs during systolic time frames and the opposite motion occurs during diastole. The degree of displacement of the myocardium is greatest at the base and decreases for more apically located segments. Though the degree of displacement changes from base to apex in a graduated fashion, the timing of this motion is synchronous for all segments. This synchronicity can be seen in both the longitudinal and radial planes. Thus, regions of tissue will move at the same time in a symmetrically synchronous fashion. This is apparent in FIG. 7.

Figure 7:
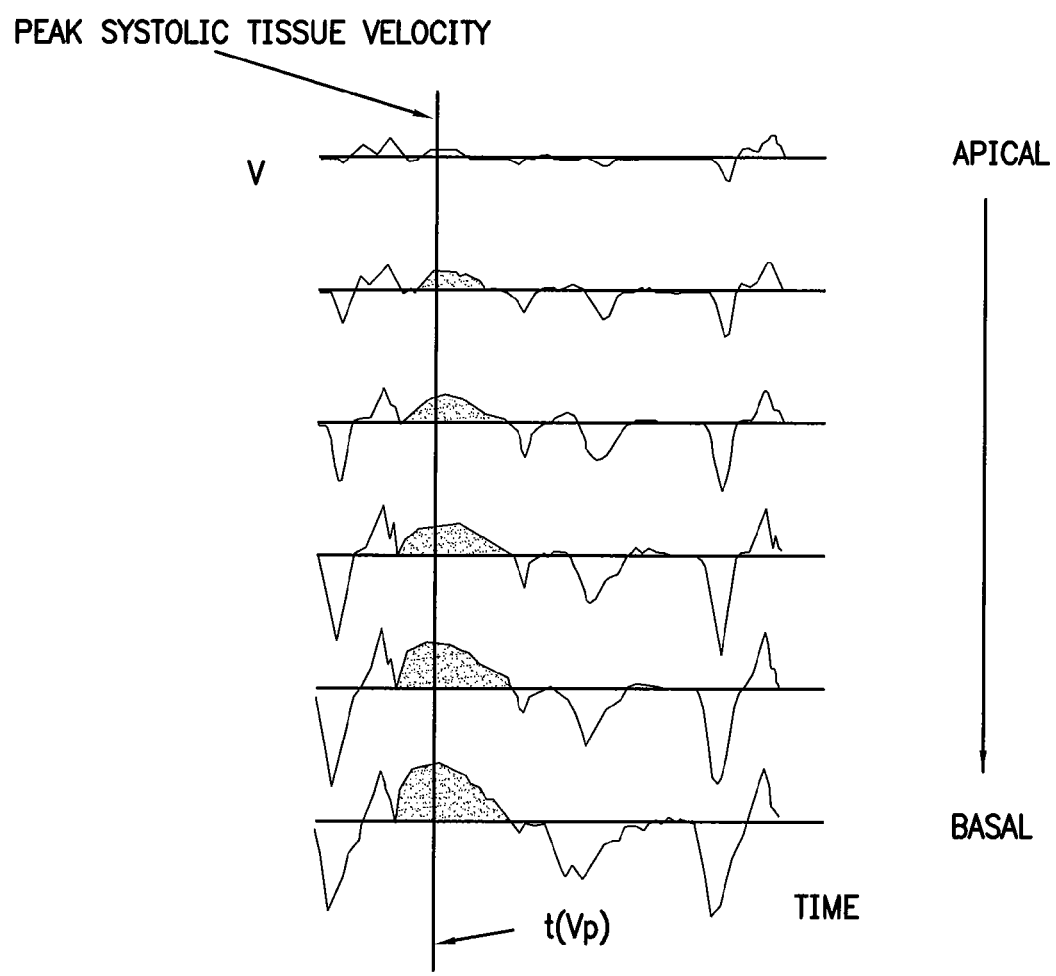
FIG. 7 depicts a TVI velocity time graph and the velocity of multiple segments of tissue simultaneously, wherein the top are more apical segments than bottom, which are more basilar.

FIG. 7 depicts a TVI velocity time graph and the velocity of multiple segments of tissue simultaneously wherein the top are more apical segments than bottom, which are more basilar. Though different regions have different peak velocities and different velocity time integrals (e.g. shaded areas) all regions move synchronously and simultaneously with regard to timing and vector.

Figure 8:
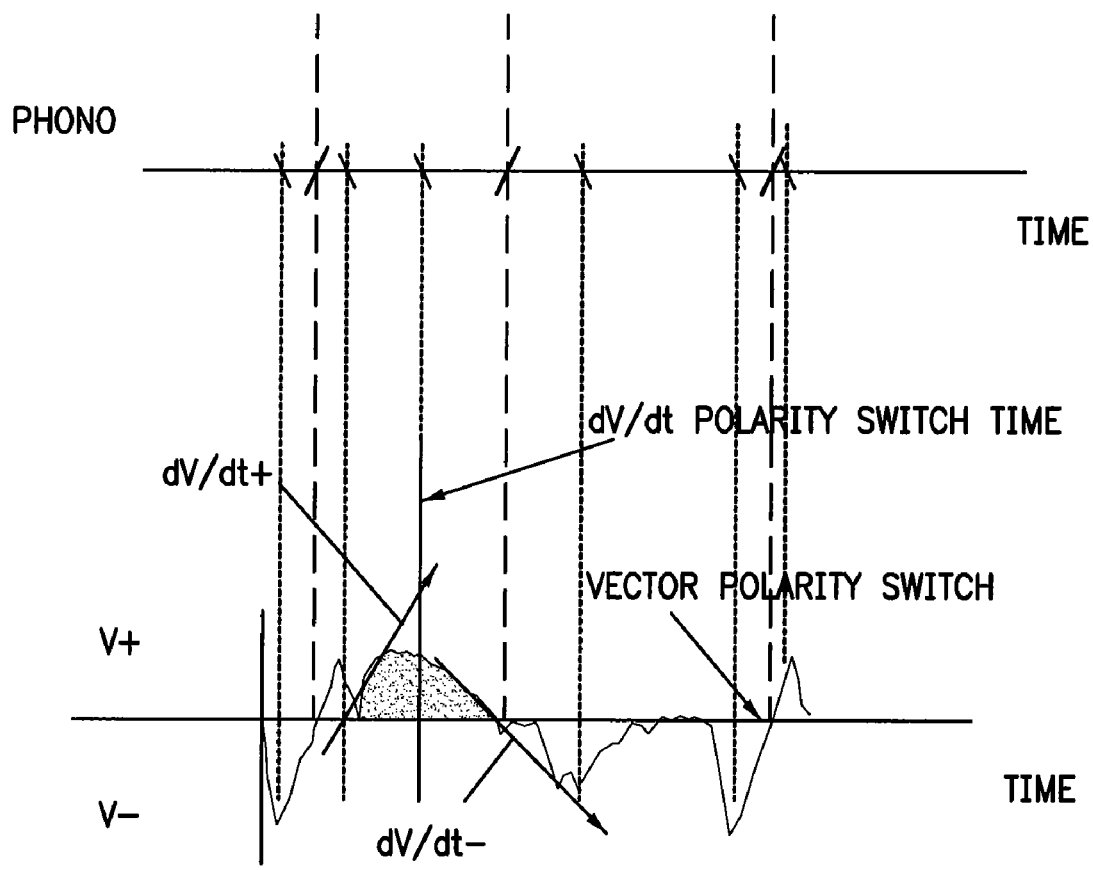
FIG. 8 depicts a velocity time graph from one region of the heart.

Referring now to the velocity time graph from one region, depicted in FIG. 8, we can define the time where velocity is toward the acoustic sensor, or transducer, V+, or, away from the transducer, V− (bottom). During the systolic ejection phase, velocity is normally toward the transducer, V+. We can also define the time when tissue motion changes direction, vector polarity switch, and change from myocardial acceleration, dV/dt+, to deceleration, dV/dt−. The latter is referred to as dV/dt or acceleration polarity switch. These polarity switches cause tissue vibration and concomitant sound which is depicted by the thick short lines on the phonocardiogram in FIG. 8 (top). The thin lines reflect lower amplitude sound related to polarity acceleration switches, and the thicker lines reflect higher amplitude as they correspond to a change in the vector of motion, vector polarity switch.

In normal individuals, essentially all segments obtain peak tissue velocity, t(Vp), at the same time during the systolic ejection phase, SEP, as can be seen in FIG. 7. All segments change vector of motion (positive to negative velocity) at the same time. All segments accelerate and decelerate at the same time (positive and negative dV/dt). This results in a homogeneous and uniform motion. The uniformity of this motion will lead to distinct patterns of sound (MDQ). The highest amplitude, sharpest sounds will occur at specific time frames. As described above, these sharp sounds occur at times when there is a change in the direction of motion (vector polarity) and a change from motion acceleration to deceleration (dV/dt polarity). During times of uniform motion without polarity switches, minimal sound will be generated from the cardiac tissues (though VQ will contribute to sound detected).

Figure 9:
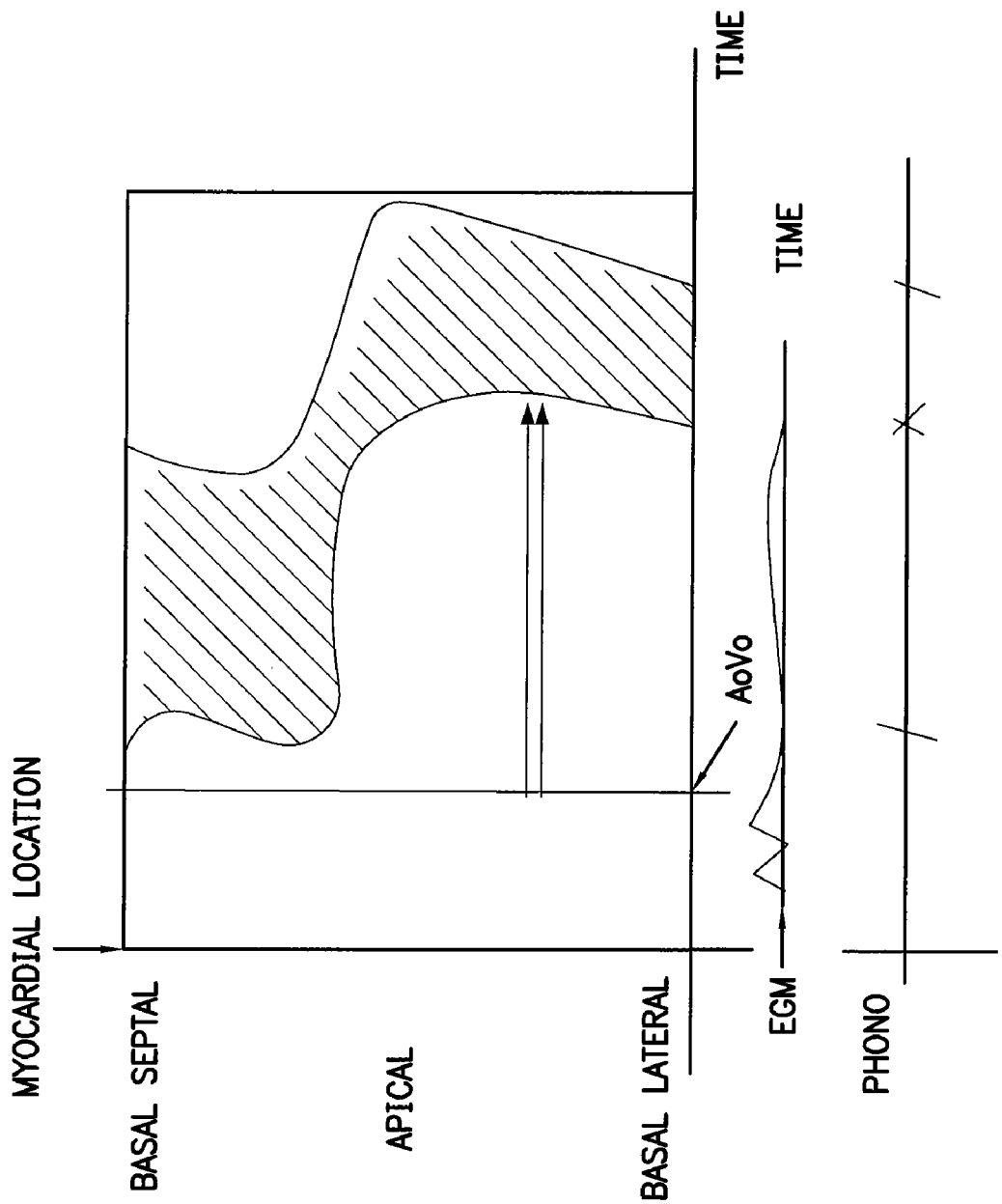
FIG. 9 depicts a representation of curved anatomical M mode where basal septal wall motion changes direction before the basal lateral wall during the systolic time frame at a different time in the pathologic state.
Figure 10:
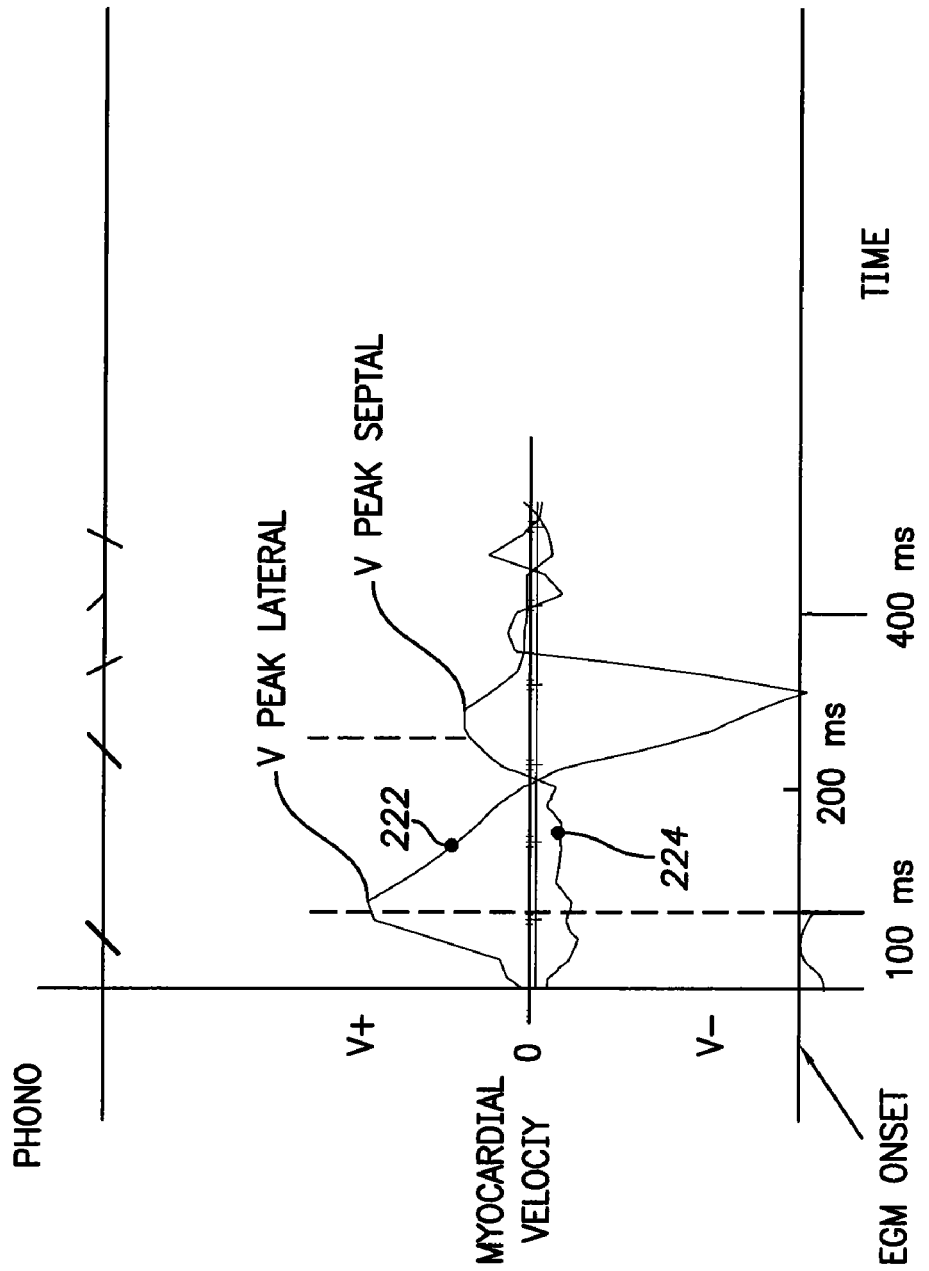
FIG. 10 depicts a velocity time graph of two discordant regions (lateral and septal) in a patient with dysynchrony.

FIG. 9 depicts a representation of curved anatomical mode, M, where basal septal wall motion changes direction before the basal lateral wall during the systolic time frame at a different time in the pathologic state. The difference in this time is shown with the double arrow. Under normal circumstances, discrete sounds will be generated during these uniform motion polarity switches. Under dysynchronous conditions (FIG. 9) a more chaotic sound pattern will result and the minimal sound state that is present under normal circumstances would be replaced by a more chaotic acoustic or sonographic signal. The temporal nature of these sounds and the MDQ can be used to differentiate the state of the myocardium. If dysynchronous electromechanical properties are present, there will be a disparity in the time of regional polarity switches. Thus, the sound generated will be lower amplitude, less discrete, less sharp and have a flatter quality, with more chaotic features. FIG. 10 depicts a velocity time graph of two discordant regions (lateral, 222, and septal, 224) in a patient with dysynchrony. As is readily seen, there are incongruent velocity curves. The resulting sound (phono) will differ, top, than that under conditions of synchrony. These differences can be detected by the disclosed system and used for monitoring purposes and for directing interval timing in a CRT. Specific acoustic properties will be seen in patients most likely to respond to CRT implantation.

Radial Myocardial Motion. Myocardial thickening and thinning occurs mainly in the radial direction. At times when myocardial thickening ends and the heart muscle relaxes, specific sounds will be generated. When the relaxation time frame ends and thickening occurs other sounds will be generated. Such occurrences can be most readily appreciated by evaluation of radial strain measurements (e.g. strain rate imaging, SRI). End-systolic and end-diastolic sounds will be comprised of sound related to regional polarity switches related to motion and those from changes resulting from myocardium changing from a contractile state to a state of relaxation. Dysynchronous relaxation and thickening will lead to different sound patterns that can be evaluated with the disclosed system in similar fashion as described above.

Figure 11:
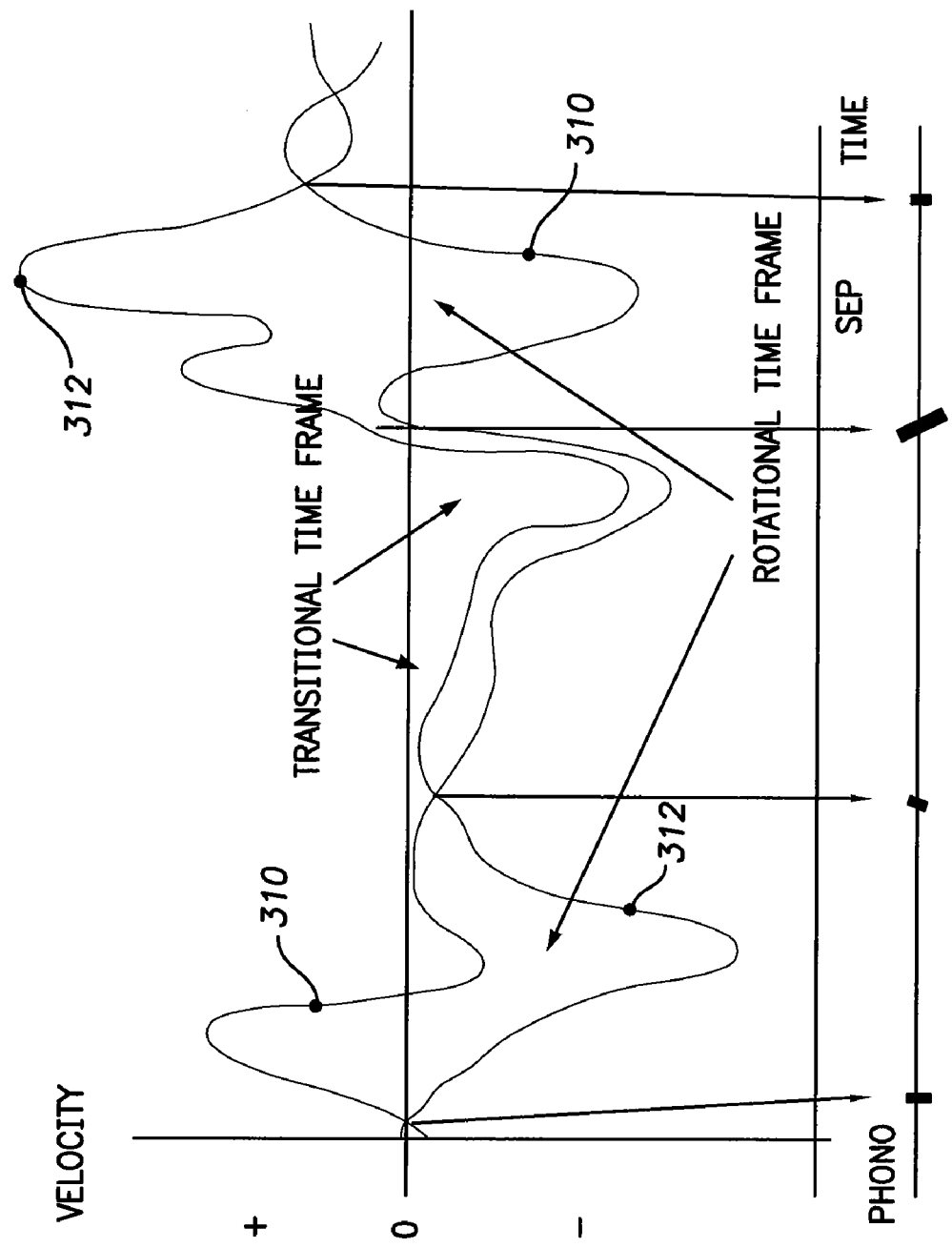
FIG. 11 shows tissue velocity time graphs depicting how cardiac rotation and torsion can lead to different cardiac sounds.
Figure 12:
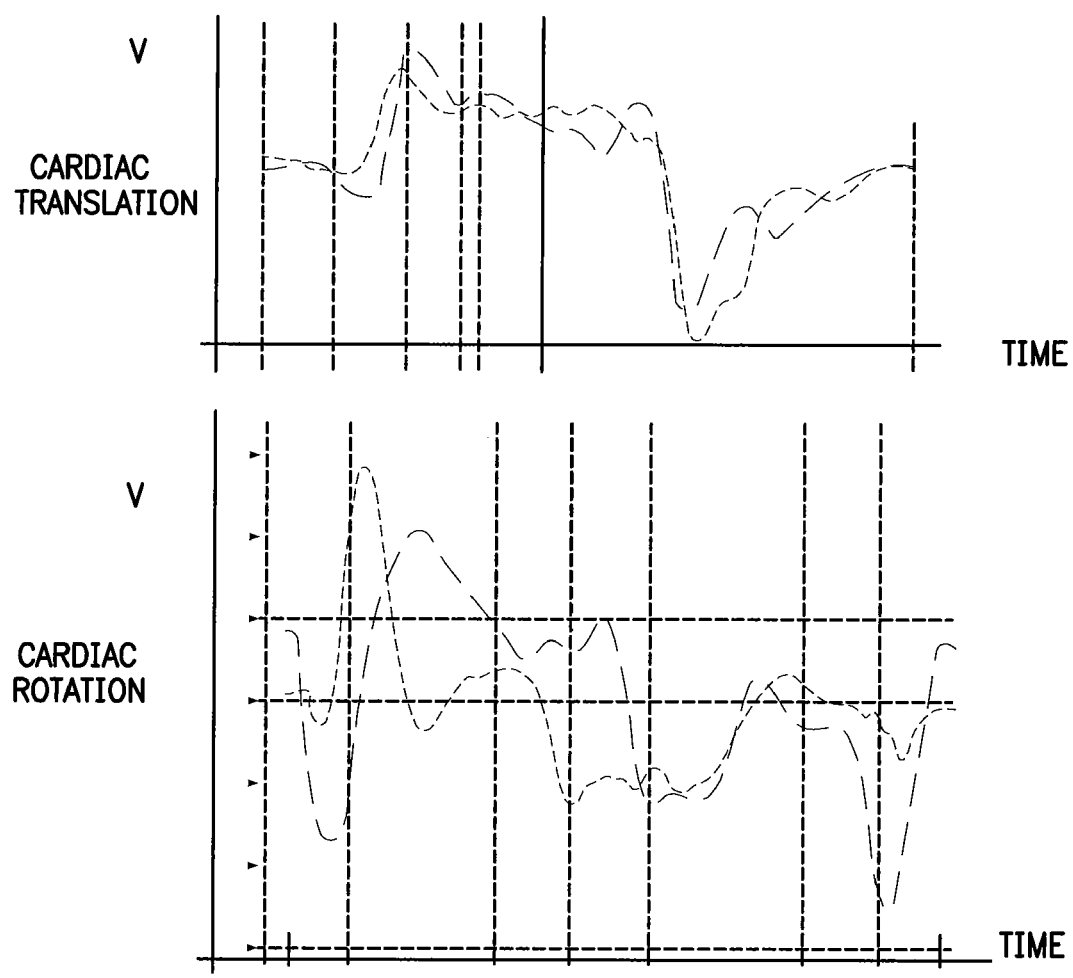
FIG. 12 depicts advanced cardiomyopathy which results in a loss of cardiac rotation and torsion, resulting in a mainly translational motion.

Cardiac Rotation and Torsion. The heart rotates and twists during the cardiac cycle. The apex and base will rotate in different directions (clockwise vs. counterclockwise) during systolic and diastolic time frames of the cardiac cycle. This results in a torsion effect that augments cardiac output and generates a suction effect for diastolic filling. Tissue velocity time graphs depicting this demonstrate how such cardiac rotation and torsion can lead to different sounds as well (FIG. 11). Curve 310 is the tissue velocity of a septal region of interest and curve 312 is from a lateral region of interest imaged from a parasternal short-axis view. Pathologic circumstances will lead to more dysynchronous, asymmetric properties of cardiac rotation and torsion and will change the sounds generated. Additionally, under circumstance of impaired diastolic suction, the volume of sound related to VQ (mitral inflow) will be reduced. Advanced cardiomyopathy may result in a loss of cardiac rotation or torsion and result in translational motion alone, as illustrated in FIG. 12. The velocity time graphs from a patient with end-stage cardiomyopathy (top) will differ from that in a patient with normal LV torsion/motion (bottom). Recently published data using MRI has demonstrated how CRT pacing can affect properties of LV rotation or torsion (Sorger J M, J Cardiovasc Magn Reson 2003; 5: 521-30, which is incorporated herein by reference).

Statistically significant differences in left ventricular (LV) rotation between patients with advanced heart failure and normal controls using tissue velocity imaging can be expected. Impairments in properties of LV torsion will affect the acoustic properties related to torsion and rotation.

Figure 13:
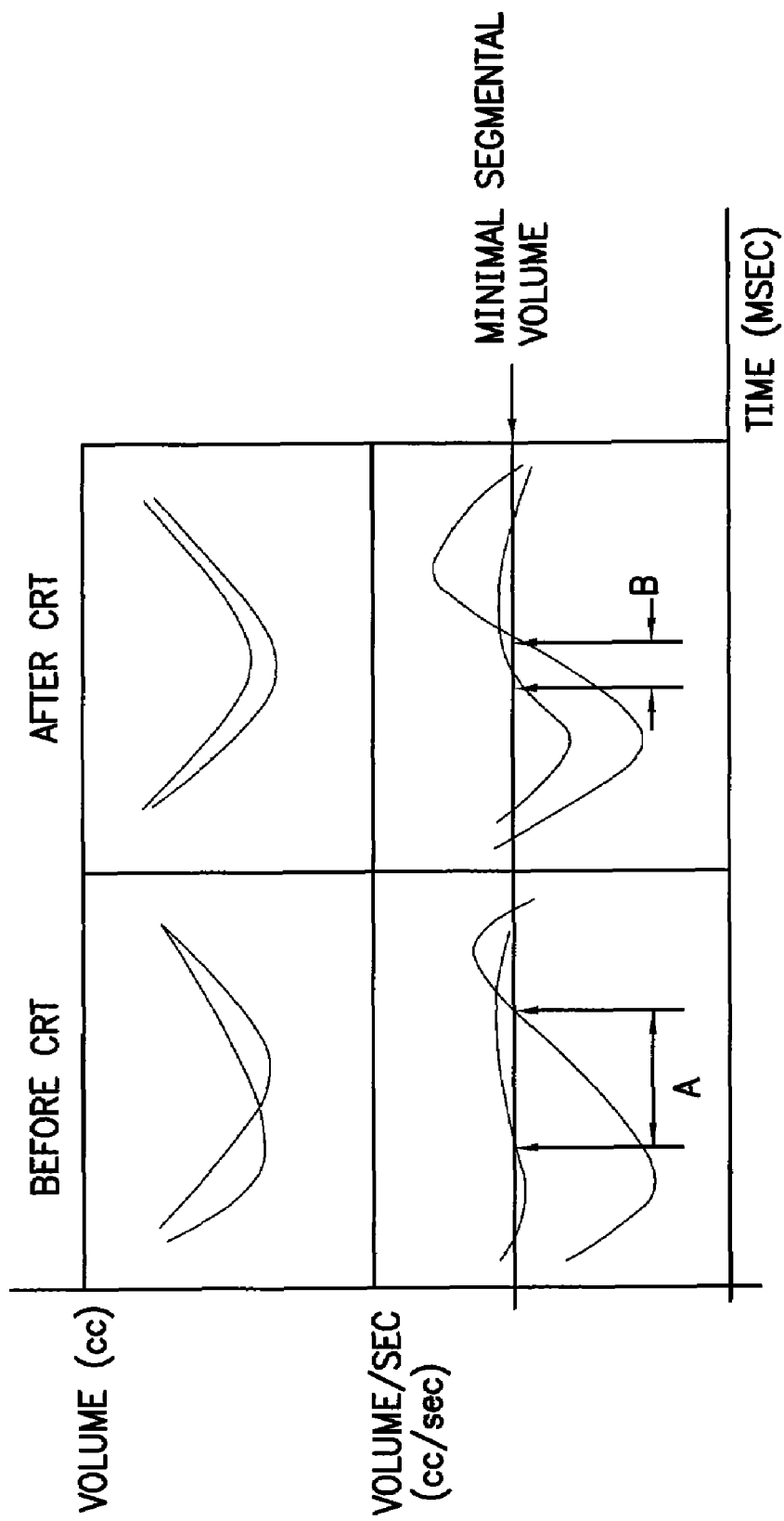
FIG. 13 depicts regional volume over time and the time derivative of regional volume (volume/sec) curves under dysynchronous and synchronous (after CRT) conditions.

Cardiac Chamber Volumetric Effects. The MDQ of these sounds will also be affected by regional and global changes in chamber size. In much the same way that the size of a speaker cabinet affects sound, changes in chamber size and regional differences in the change of volume over time will affect the MDQ. FIG. 13 depicts regional volume over time and the time derivative of regional volume (volume/sec) curves under dysynchronous and synchronous (after CRT) conditions. Such curves can be generated with echocardiography equipment that is currently available (for example, systems manufactured by Philips). Referring to FIG. 13, we see regional volume time curves generated using ultrasound technology for 2 locations within the left ventricle. In the pathologic state, the changes in volume of these regions will differ in both the degree of volume change and time of volume change. Improvements in synchronization can affect both properties (a>b). Under conditions of synchrony, the MDQ will differ from a heart in the pathologic state. Detection of such differences in a given individual will allow for determination of more synchronous conditions.

Figure 14:
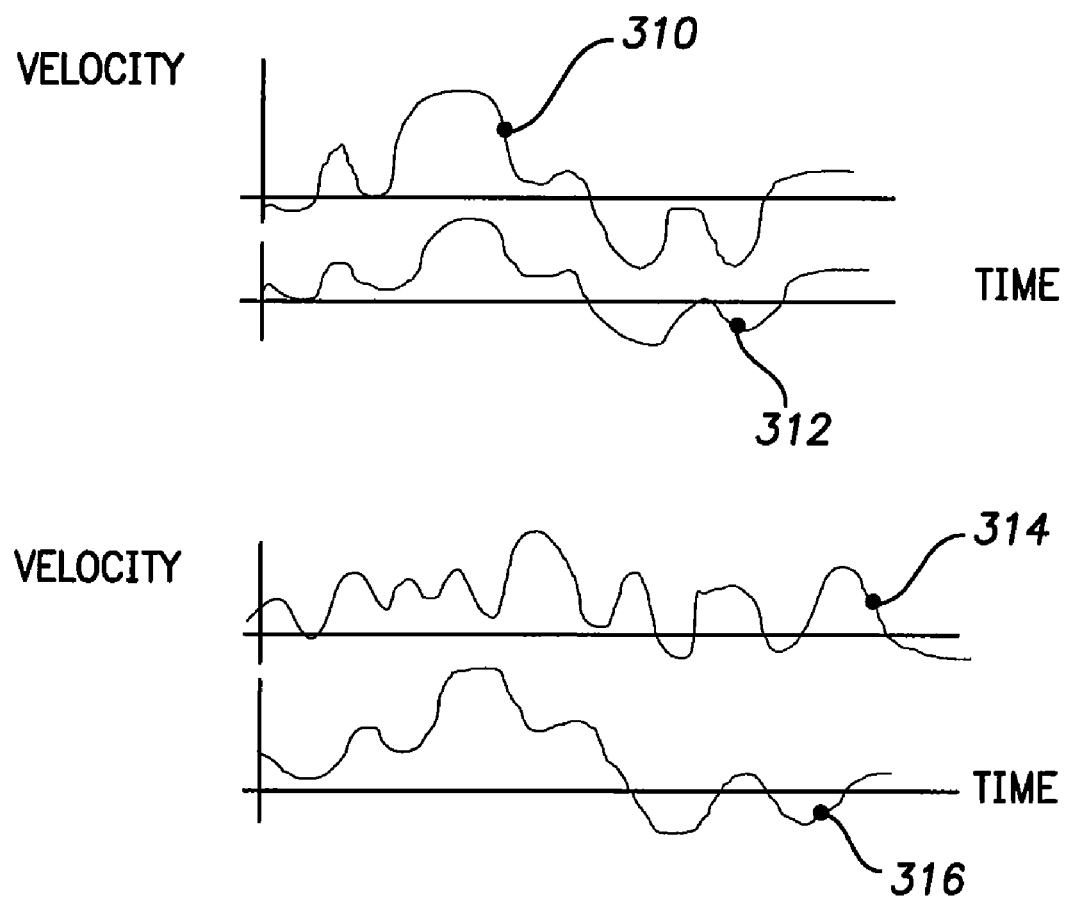
FIG. 14 depicts a normal tissue velocity curves derived from septal and lateral regions of interest (top), as compared to tissue velocity curves from a patient with normal lateral TVI patterns and pathologic TVI patterns from a septal wall region of interest (bottom) that causes reverberation artifact.

Reverberation. As described above, normal conditions will result in uniform motion. Such uniform motion will lead to more distinct sound patterns, sharper sound and less noise during specific time frames. The acoustic wave function will be less chaotic in nature as a result of homogeneous tissue motion and myocardial deformation. Under conditions of dysynchrony, more chaotic acoustic wave functions will result because of acoustic misalignment. Variations in the shape of the cardiac chambers (e.g. less symmetry) will result in more distorted sound quality and loss of harmonics that may result from the normal regional and global volumetric changes during the cardiac cycle. In more advanced cardiomyopathy, with significant increases in LV end-diastolic and end-systolic volumes, lower frequency sounds will be noted and harmonics may be restored as a result of a larger, more globular chamber size. Under dysynchronous conditions, these phenomena will result in distortion and acoustic reverberation artifact as well as acoustic frequency shifts. This can be visualized by evaluation of tissue velocity imaging data in a cardiomyopathy patient with dysynchronous electromechanical velocity time curves. Referring to FIG. 14, we see a normal tissue velocity curves derived from septal (310) and lateral (312) regions of interest (top) and those from a patient with normal lateral TVI patterns (316) and pathologic TVI patterns from a septal wall region (314) of interest that causes what is currently described by those experienced in the art as reverberation artifact. In actuality, this is not artifact. The reverberation in the velocity time curve is a result of impaired myocardial contractility, dysynchronous wall motion and tethering effects from adjacent myocardium that is moving out of phase with the region of interest in a chaotic fashion. Multiple velocity peaks may be detected as well as other abnormalities. The temporal resolution of TVI allows for detection of such "artifacts". Such reverberation will generate specific sounds that can be mathematically described with the acoustic wave function. In such circumstances this signal may appear to be noisy when in fact it is an accurate representation of the pathologic state. Such an acoustic wave function can be described using mathematical formulations of chaos.

Sensor Design And Processing Approaches

Figure 15:
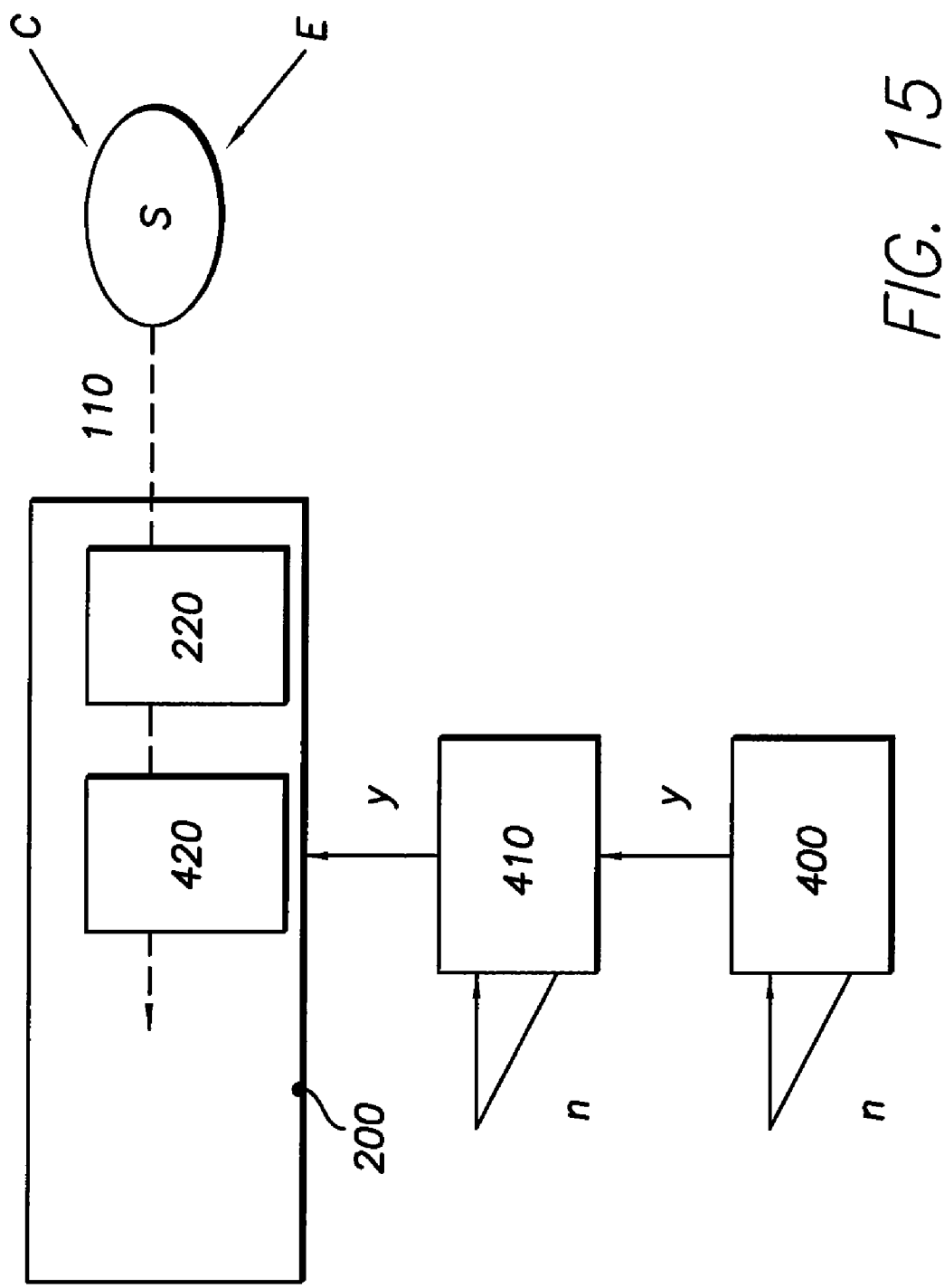
FIG. 15 illustrates use of band-pass filtration and other techniques to remove extraneous sounds.

Sensor Design. The signal which is analyzed by the system is the cardiac acoustic waveform generated by the heart during the cardiac cycle. The sensor design is such that the signal to noise ratio (SNR) will be ideal. Impedance matching of the sensor to the surrounding tissue as to optimize the SNR is necessary. A fluid filled interface between a piezoelectric accelerometer that has a wide frequency response capable of detection of low amplitude, low frequency sounds and short-lived higher frequency sounds related to myocardial reverberation is needed. The acoustic sensor AS should be relatively impervious to ambient noise and the effects of patient motion and friction due to bodily tissues or fluids. Band-pass filtration and other techniques can be incorporated into the system to help remove extraneous sounds as well, as illustrated in FIG. 15. The design of a sensor similar in make to the one needed in this application can be found in a publication by Padmanabhan et al., "Accelerometer Type Cardiac Transducer for Detection of Low-level Heart Sounds: IEEE Transactions on Biomedical Engineering, 40(1), pp. 21-28, January 1993, which is incorporated herein by reference.

Any sensor capable of accomplishing the same or similar results may be used for this system and constructed by those experienced in the art. A plurality of additional sensors is used to identify the appropriate times for acoustic data acquisition. Determination of periods of rest, relative apnea or hypopnea, and position are examples of such sensors that have been incorporated into cardiac rhythm management (CRM) device platforms.

FIG. 15 details such a sensor design with a flow diagram describing how such data can be acquired. Acoustic sensor AS detects cardiac acoustic waveforms, C, which are processed within the sound filtration and digital conversion system, 200, as describe above. Step 110 is enabled by switch 420 if criteria 400 and 410 are met. In step 400, an accelerometer detects that the patient is at rest such that noise related to patient movement is minimal. In step 410, a minute ventilation sensor defines a period of time of relative apnea or hypopnea such that noise related to respiration is minimal. Thus, data acquisition occurs during specific time frames when the SNR will be optimal, and when extraneous sound is at a minimum. In a preferred embodiment, sensor AS is capable of detecting extraneous sound, E, that has been identified by the sound filtration and digital conversion system 200 as being non-cardiac and only enables switch 420 to be closed when cardiac sounds, C, are significantly more audible than E and when differentiator, 220, is most able to be discern C from E. In this example, differentiator 220 is part of 200, though alternate constructions are possible and are within the scope and spirit of the present disclosure.

Acoustic Wave Function. The acoustic wave function is a term the inventor has applied to any function that may be used for providing a mathematical description of acquired cardiac acoustic data (e.g. MDQ) including but not limited to those mentioned within the body of this patent application. For example, the mathematical descriptor may relate to cardiac performance, uniformity of sound, degree of heterogeneity of sound or it may relate to the presence or degree of cardiac pathology, as defined by any analysis of cardiac acoustics.

By way of example, cardiac performance may be analyzed using the AoVQTI, or aortic blood flow time integral, which is a representation of the aortic blood flow during the SEP. The AoVQTI is a function of the product of the peak amplitudes (AoVQamp) (or the upper envelope) of the acoustic signal possessing the frequency spectrum characteristics associated with trans-aortic valve blood flow during the SEP (in absence of aortic stenosis) and the duration of AoVQ (SEP), as reflected below in Equation 3:

$$AoVQTI = t(SEP) * AoVQamp \text{ in units of dB*sec;} \quad \text{Equation 3}$$

Similarly, the integral of the acoustic envelope of AoVQTI as a function of time during the SEP represents AoVQTI, as illustrated in FIG. 5.

A number of methods can be used to accomplish the task of determining AoVQTI or other acoustic wave function features that necessitate characterization of the origin of acoustic data. Neural networks, wavelet analysis, Fast Fourier Transform are examples of available techniques for deriving this function. Discrete Time Fourier Transform (DFT), Vector quantification methods, genetic algorithms, Linear Predictor analyses are other examples.

In a preferred embodiment, mathematical models related to chaos theory are employed to define C as being more organized and uniform with minimal chaos. Under circumstances of synchronous and symmetric wall motion (ideally with minimal mitral regurgitation), the acoustic wave function describing the detected sound, C, will be ascribed a value of 1. Under most chaotic conditions and non-uniform sound, the acoustic wave function will approach zero. The value of the acoustic wave function after effective CRT will be closer to 1.

Heart sound processing with time dependent fractal dimensions can be used for derivation of an acoustic wave function that is descriptive of valvular characteristics and degree of synchronization. An excellent review of how such techniques may be applied can be found in a thesis prepared by Fred Hasfjord, Dept. of Biomedical Engineering, Linkopings University "Heart Sound Analysis with Time Dependent Fractal Dimensions"; Feb. 25, 2004, (http://www.imt.liu.se/~chrah/exjobb/fracdim.pdf) which is incorporated herein by reference. The dimension trajectories calculated with the continuous box method allows for segmentation of the heart sounds by providing a clear distinction between trajectory characteristics. The variance method and Higuchi method are also techniques that can accomplish the same.

Fractal Analysis of Minor Sounds. Once heart sound segmentation has been accomplished, the acquired data may be analyzed in a variety of ways as to provide relevant physiologic information. Removal of the major heart sounds and amplification of the ambient sounds related to wall motion will allow for a more detailed analysis of the minor heart sounds. By way of example, an analysis of the power spectra, and use of FFT techniques in both frequency and time domains to analyze the minor heart sounds will characterize and identify cardiac acoustics related to wall motion, reverberation, synchronicity and symmetry of motion. Time or frequency dependent fractal dimension analysis can be used to identify the degree of chaos present in sound that falls within a specific frequency range or power spectrum and assess properties of self-similarity. The fractal dimension associated with dysynchronous wall motion possessing more disorganized temporal characteristics will differ from that found under circumstances of uniform, synchronous wall motion.

Analysis of the acquired fractal dimension trajectory using different window sizes and window spacing can yield clinically useful information. After removal of the major heart sounds, the system may analyze acoustic properties of time sequence self-similarity. Loss of self similar properties will occur under conditions of dysynchrony. As a greater degree of myocardial wall reverberation and a greater spectrum of acoustic frequencies with greater time variance will be seen in hearts with electromechanical dysynchrony, there will be less self similarity. The width of low dimension peaks and the dimension values of the peaks are examples of parameters that may be quantified with such an analysis, though other parameters may be derived that are within the scope and spirit of the present disclosure.

Acoustic Waveform Compressibility Function. The inventor also has conceived of a means for ascribing values to the acoustic wave function by the system's ability to compress C into a minimal number of bytes. If the system needs to exceed set, graduated values of numbers of bytes sampled for compression of sound C, the sound C is characterized as being more chaotic. For example, if less than 24 megabytes (MB) are needed to adequately define C over one cardiac cycle, then the acoustic wave function will be ascribed a number 1. Such conditions will be met if there is minimal reverberation and uniformity in motion, myocardial acceleration, deceleration and synchronized polarity switches. If 24 to 36 MB are needed the value will be 0.75. If 36 to 48 MB is needed then the value will be 0.50, and so forth. The graduated scale need not be linear. The general idea is that the acoustic wave function in this embodiment is proportionate to the number of bytes needed to be sampled for system 200 to compress received sound C for storage in the system memory. The more chaotic the acoustic waveforms, the more bytes will be required during any given data compression scheme.

One potential limitation to this compressibility acoustic wave function is that under most advanced cardiomyopathy, cardiac rotation is lost and cardiac translation will present with global reductions in myocardial wall thickening. The loss of the characteristic sounds due to rotation, torsion and radial and longitudinal myocardial deformation will generate acoustic waveforms with lower frequency spectra and lower amplitudes secondary to cardiac translation, global hypocontractility and larger chamber sizes. Such circumstances may result in lesser amounts of acoustic data but can be identified by analysis of MDQ characteristics. The distinctive features of the acoustic waveforms in such circumstance are higher frequency, lower amplitude sounds related to dysynchronous, chaotic myocardial reverberation and lower frequency sound related to larger chamber size. The frequency and power spectra associated will serve to identify such conditions. The acoustic waveforms may or may not require more bytes for data compression. Labeled examples and template data acquired from population studies will allow the system to differentiate a variety of pathophysiologic states using techniques such as neural networks, and will serve to identify when the compressibility function can be implemented.

In broad terms, the disclosed system may use a number of algorithms for segmentation and identification of cardiac sounds and acoustic properties. These properties can be quantified and described by the defined acoustic wave function which provides a mathematical descriptor that relates to certain pathophysiologic cardiac conditions. The resulting acoustic wave function can be used to grade severity for monitoring purposes, and to guide closed loop programming of a CRT devices' interval timing.

Data Compressibility Function. The concept of quantifying the memory required for data compressibility may be applied to other technologies including but not limited to analysis of electromagnetic energies other than sound. Thus, the data compressibility function is a simplified means for determining the degree of chaos present in any system which detects electromagnetic energy or other types of data. It is dependent on sampling frequency and the time of each data acquisition window, and as such these parameters need to be constant when any comparisons are made between different states. The data compressibility function constitutes a separate embodiment from the sound-related concepts described in this manuscript, as it may be used for analysis of a variety of data and waveforms. Its relevance to acoustic waveforms described herein is by way of example.

Ensemble Averaging. Ensemble averaging techniques can be implemented in the system. Such techniques will allow for a reduction in random, extraneous noise and allow for more accurate identification of cardiac acoustics. Sounds which are repetitive can be amplified while those that occur in a more random fashion may be eliminated.

Labeled Examples. The inventor recognizes that sound secondary to myocardial reverberation may be removed during ensemble averaging techniques, as such acoustics are more likely to be random and chaotic. Labeled examples from patients who have been identified as having electromechanical dysynchrony can be used to program the system to identify the characteristics of myocardial reverberation and to differentiate such desired data from unwanted extraneous noise. Removal of the major heart sounds during composition of the temporal framework and subsequent fractal dimension analysis, with amplification of the minor sound for further processing, is necessary. As dysynchronous myocardial velocity time curves are more likely to be repetitive over many cardiac cycles than noise, the system will be able to learn which acoustic data is noise and which data is not.

In an alternate embodiment, an interface similar to that described in the parent application may be integral to the system and used for programming a data bank of labeled, template examples that may be stored in the memory of the disclosed device. Such an interface can be used to 'teach' a patient's device which acoustic wave functions correlate with conditions of electromechanical dysynchrony and conditions of synchronization. Use of an interface that receives tissue velocity imaging data and device data while changes in interval timing are occurring will allow for the disclosed system to learn and program storage of labeled examples. The means for designing such an interface are described, for example, in U.S. Pat. No. 7,065,400, which has previously been incorporated by reference herein.

The disclosed cardiac acoustic monitoring system may be part of an external system whereby the acoustic sensor AS is placed on the chest of the patient for acquisition and analysis of cardiac acoustic data. Such an embodiment would not be capable of real time dynamic programming and monitoring, but it could be used at regular intervals for both diagnostic purposes and for optimizing interval timing. Closed loop programming using impedance data that is descriptive of dysynchrony, as described in, for example, U.S. Pat. No. 7,010,347 and U.S. Pat. No. 7,065,400, can accomplish the same task with real time programming of labeled examples within the device. Such a system will allow for the present cardiac acoustic monitoring system to complement the functions of such a closed loop system within the device (e.g. FIG. 2b) and provide an additional or alternate means for monitoring patient status (e.g. cardiac performance, valvular function, degree of dysynchrony).

Multiple Cardiac Acoustic Signals. Use of more than one acoustic sensor AS will allow for more accurate determination of regional acoustic properties. An additional advantage of multiple acoustic sensors is that the directionality of sound can be identified. Specific murmurs originate in different locations and radiate sound in a variety of directions. For example, sounds related to aortic stenosis occur at the base of the heart and radiate superiorly, away from the heart. Mitral regurgitant sounds originate near the apex of the heart and often radiate laterally toward the axilla. As the murmurs of aortic stenosis and mitral regurgitation occur during the SEP, the systems ability to differentiate between these murmurs will be aided by identification of acoustical vectors in addition to VQ MDQ.

Acoustic sensors incorporated within right ventricular (RV) and left ventricular (LV) leads may be used to derive separate regional major or minor acoustic data. An example of major acoustic data would be the delineation of the temporal relationship between the SEP of the pulmonic and aortic valves. This data can be used to quantitate interventricular dysynchrony. Echocardiography techniques of doing the same are described in the cardiology literature. This might be derived with implanted RV and LV lead systems or by external acoustic sensors placed on the chest wall, or a combination thereof. An example of minor acoustic data includes delineation of regional cardiac performance (regional sonographic Tei indices) from an acoustic sensor receiving proximate acoustic data from the RV or septum and one from an LV lead.

Minor heart sounds related to regional myocardial motion may be analyzed similarly after subtraction of major heart sounds as described above. Such data could also be acquired from an acoustic sensor implanted in subcutaneous tissues anatomically located, for example, to receive acoustic data from the right and left heart.

Figure 16:
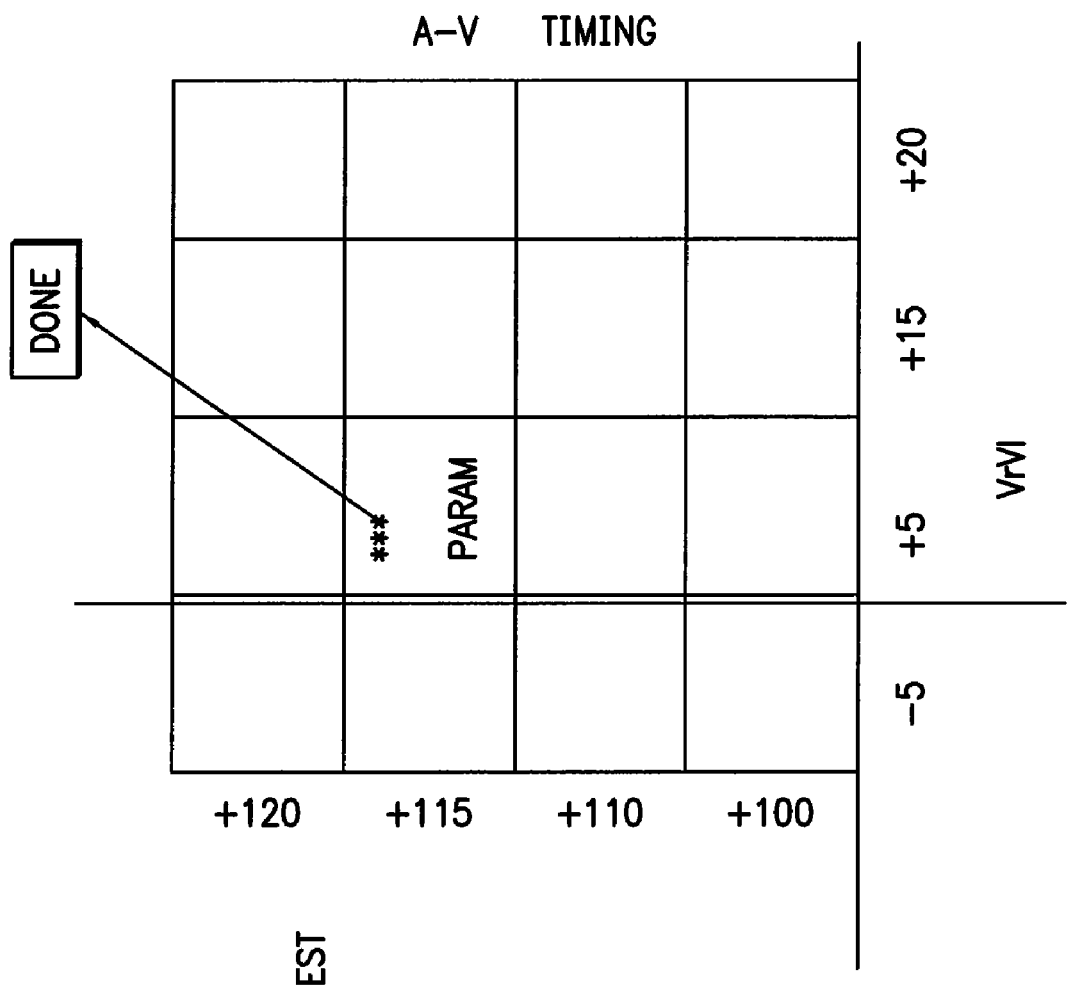
FIG. 16 illustrates the application of the technologies described herein as an internal or external interface between a cardiac acoustic monitoring system and a CRT system.

Matrix Optimization Method (MOM). In a CRT device, modification of interval timing as to optimize cardiac performance and minimize dysynchrony will improve outcome in a significant subgroup of patients with implanted CRT. Examples of algorithms for such optimization are described in U.S. Pat. No. 7,010,347 and U.S. Pat. No. 7,065,400. The application of the technologies described herein as an internal or external interface between a cardiac acoustic monitoring system and a CRT system can be understood by referring to FIG. 16. Data derived by the cardiac acoustic monitoring system, (e.g. acoustic wave function), can be the parameter being optimized, CPPo, using the MOM. By way of example, this technology will use characterization of acoustic wave functions which are seen under synchronous and dysynchronous conditions using a graduated scale. As described in the section on chaos, the normal synchronous state can be assigned a value of 1 and the most dysynchronous state can have a value of 0. As mentioned above, this characterization can be done by performing analyses of normal individuals and those with varying pathologic states and different degrees of disease severity (labeled examples). Those acoustic wave functions which reflect optimal conditions will be found at a specific set of interval timing. Assessment of MR severity and cardiac performance (e.g. GSTI, AoVQ amplitude time integral) can also be performed using this technology. This ideal acoustic wave function can be determined at a time after CRT implant while the patient is undergoing TVI using an interface that serves to communicate acoustic data and ultrasound assessments of synchronization. In such an embodiment, other signals such as impedance data may be incorporated into this analysis. In this fashion, a plurality of data (e.g., acoustic, impedance, TVI) can be used to define ideal conditions for a given patient as to facilitate real time closed loop programming of CRT interval timing tailored for individual patient using the sounds of the heart.

Numerical Scaling And Audio-Video Communication of Diagnostic Information

In the preferred embodiment, the original analog acoustical data acquired by an acoustic sensor undergoes digital signal processing, DSP. The DSP serves to derive temporal data related to valvular events, differentiate major from minor sounds and convey information related to reverberation of cardiac tissue and electromechanical properties. These data can be used in a number of ways to derive indices of cardiac performance, quantify valvular heart disease and identify electromechanical dysynchrony.

The end result data may then be conveyed to the clinician. Any of a variety of display methods may be used to assist the clinician's evaluation of a given patient. A first example is a numerical graphical display of the various cardiac performance indices. By way of example, normal values of AoVQ and MRVQ cardiac performance indices are given a value of 1. The most advanced disease state with lowest stroke volume will be given a value approaching zero. Alternate means for numerically scaling such indices may be used as well. Conventional values of the Tei index may be implemented as well. Such data may be combined to generate a single cardiac performance index. Similar graduated scales may be developed for evaluation of valvular heart disease and electromechanical dysynchrony.

A second example provides audio representation of the acquired data for use by the clinician. The digital signals may be converted to analog format and amplified. In a preferred embodiment, the heart sounds are generated in a frequency range that resembles familiar heart sounds heard through a conventional stethoscope. Video representation of the acquired data may be performed using color imaging techniques similar to blood flow and tissue Doppler displays or alternate method for display.

In one embodiment of the present disclosure, electromechanical dysynchrony may be represented with an audio signal that becomes more disorganized under more dysynchronous conditions. Musical sounds that can include a conventional audio signal (e.g. compact disc) written by any selected composer may be processed to sound as originally composed under circumstances of electromechanical synchrony. The musical signal can be processed to be more chaotic as dysynchronous conditions are detected in a graduated fashion. A video signal can be displayed simultaneously providing the clinician with a numerical scale and audio and video data for evaluation of a variety of pathophysiologic conditions. Such supplemental means for representing the state of the heart will expedite the diagnosis of the pathophysiologic state.

Correlating Acoustical And Impedance Data To Assess And Augment Mechanical Function Of The Heart As mentioned previously, data acquired from acoustic sensors may be used in conjunction with other complementary data sources to provide a more comprehensive profile of mechanical cardiac and valvular function. By using data from different modalities, limitations caused by electromechanical dissociation and reliance solely upon electrophysiological data may be overcome to further optimize resynchronization therapy.

As described in U.S. Pat. No. 7,010,347 and U.S. Pat. No. 7,065,400, impedance waveforms and impedance data obtained from intracardiac electrodes of a CRT device can be used to describe a number of cardiac properties, including properties of dysynchrony and cardiac performance. Acquisition of impedance data can be accomplished, for example, by delivering pulses of 200 uA, 30 us pulse width at a frequency of 128 Hz applied to two electrodes positioned along one vector (electrode pairs) and measuring the resulting voltage between electrodes located along the same vector. These pulses will not depolarize myocardium, will cause only limited battery drain and have a frequency with an acceptable signal to noise ratio. The resultant time dependant impedance, $Z(t)$, peaks when there is maximal systolic ventricular wall thickness and minimal intracardiac blood volume.

The time dependent impedance signals or waveforms derived in this fashion relate to intrinsic myocardial properties. If signals are acquired between specific electrode pairs, the regional myocardial properties can be derived. The integrity of these waveforms may be subject to significant noise (poor signal to noise ratio) and inferior signal quality may result. This is especially true if data sampling occurs in a vector where there is impairment in myocardial contractile properties. Derivation of specific characteristics of these waveforms may suffice, even though overall signal quality is poor. Measurement of peak impedance and first and second order derivatives of impedance waveforms will relate to myocardial contractility. Assessment of the time required for a waveform to reach peak impedance will relate to myocardial synchrony if comparisons can be made to waveforms derived in alternate regions (e.g. right and left ventricular vectors).

Morphologic characterization of waveforms derived along multiple vectors is related to native myocardial contractile and relaxation properties (herein referred to as Global Cardiac Performance) and requires better signal fidelity than measurements of time to peak impedance or peak impedance. A comparison to normal waveform templates or changes in waveform morphology in a given patient reflects inter- and intra-individual variations in myocardial contractile (systolic) and relaxation (diastolic) properties.

Event Timing Using Impedance Data

Event timing relates to opening and closing of the heart valves, such as the closure of the aortic valve. Myocardial thickening that occurs after the aortic valve is closed is work inefficient and will lead to detrimental remodeling secondary to regional strain mismatch of normal contractile tissue and neighboring dysynchronous myocardial segments. Event timing can also relate to mitral valve opening and closing and aortic valve opening. If all events can be delineated we can define isovolumic relaxation, systolic ejection period and isovolumic contraction. This allows, for example, relating any signals monitored within the device to systolic and diastolic time frames throughout the cardiac cycle (temporal systole and diastole) to intracardiac electrogram signals, impedance waveforms, and acoustic signals. For descriptive purposes and by way of example, this invention will focus on aortic valve closure as a valvular event, which can be more readily defined with impedance waveforms. Impedance signals derived from intracardiac electrodes which best elucidate aortic valve closure will be utilized. By defining timing of such events, the appropriate correction factors may be applied to multi-site pacing stimuli. Implementation of such correction factors will allow intrinsically depolarized and extrinsically paced myocardium to contract synchronously during the systolic ejection period while the aortic valve is open (multidimensional fusion).

Event timing relates to times of myocardial contractility and relaxation, mechanical systole and diastole. Mechanical systole and diastole does not occur in all myocardium simultaneously. Delays in electrical activation (conduction abnormalities) and myocardial processes such as infarction (mechanical abnormalities) cause dysynchronous mechanical events. Such dysynchrony can be minimized, in part, by pre-excited stimulation of dysynchronous myocardial tissue at the appropriate time. This pre-excited interval (electromechanical correction factor, EMCF) can be derived through analyses of intrinsic electrograms and impedance signals.

Defining Valvular Events Using Impedance Data

Figure 17:
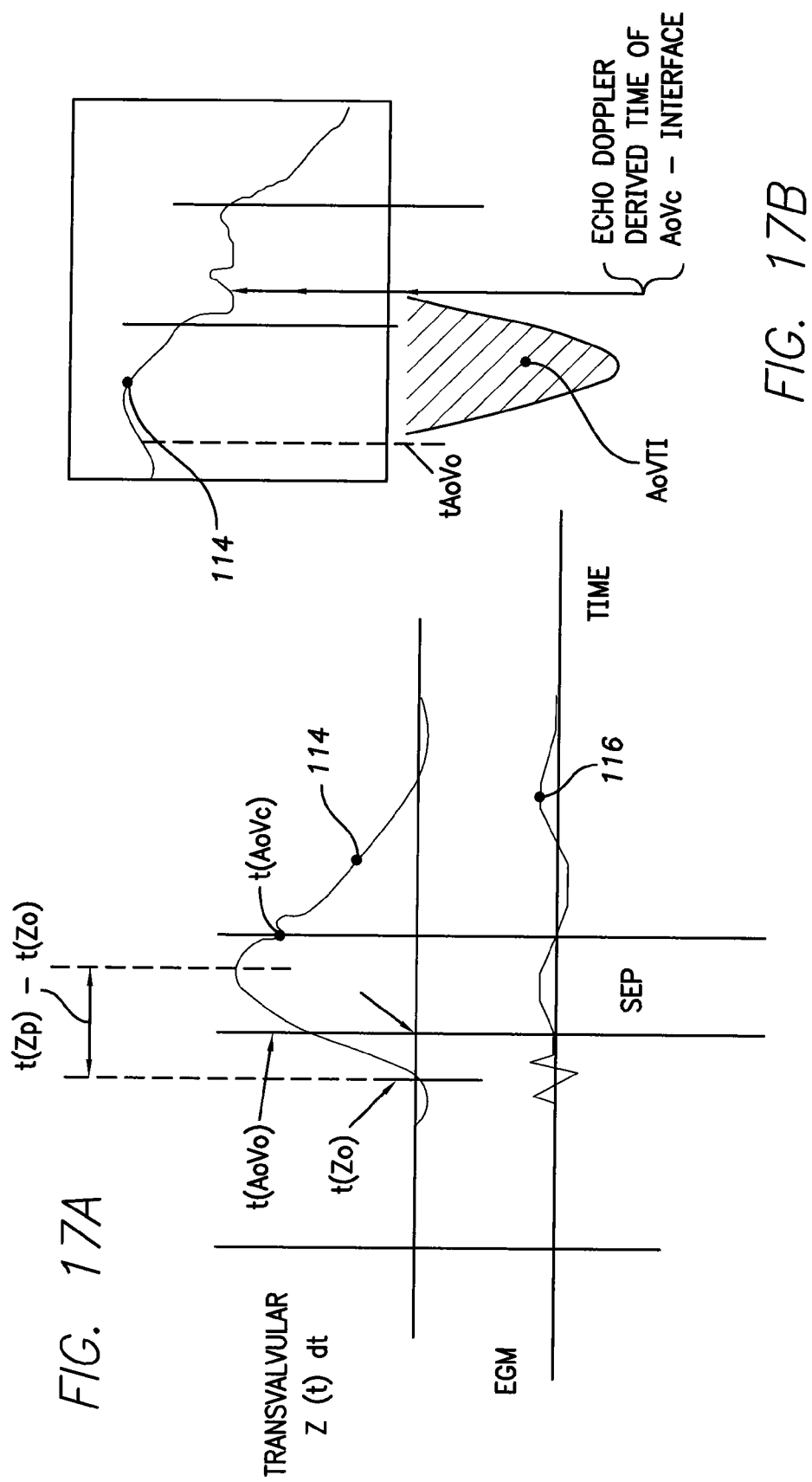
FIGS. 17a and 17b demonstrate valvular event timing during the cardiac cycle and the relationship between the impedance signal and Doppler derived measurements of blood flow across the aortic valve as to accurately denote time of aortic valve closure.
Figure 18:
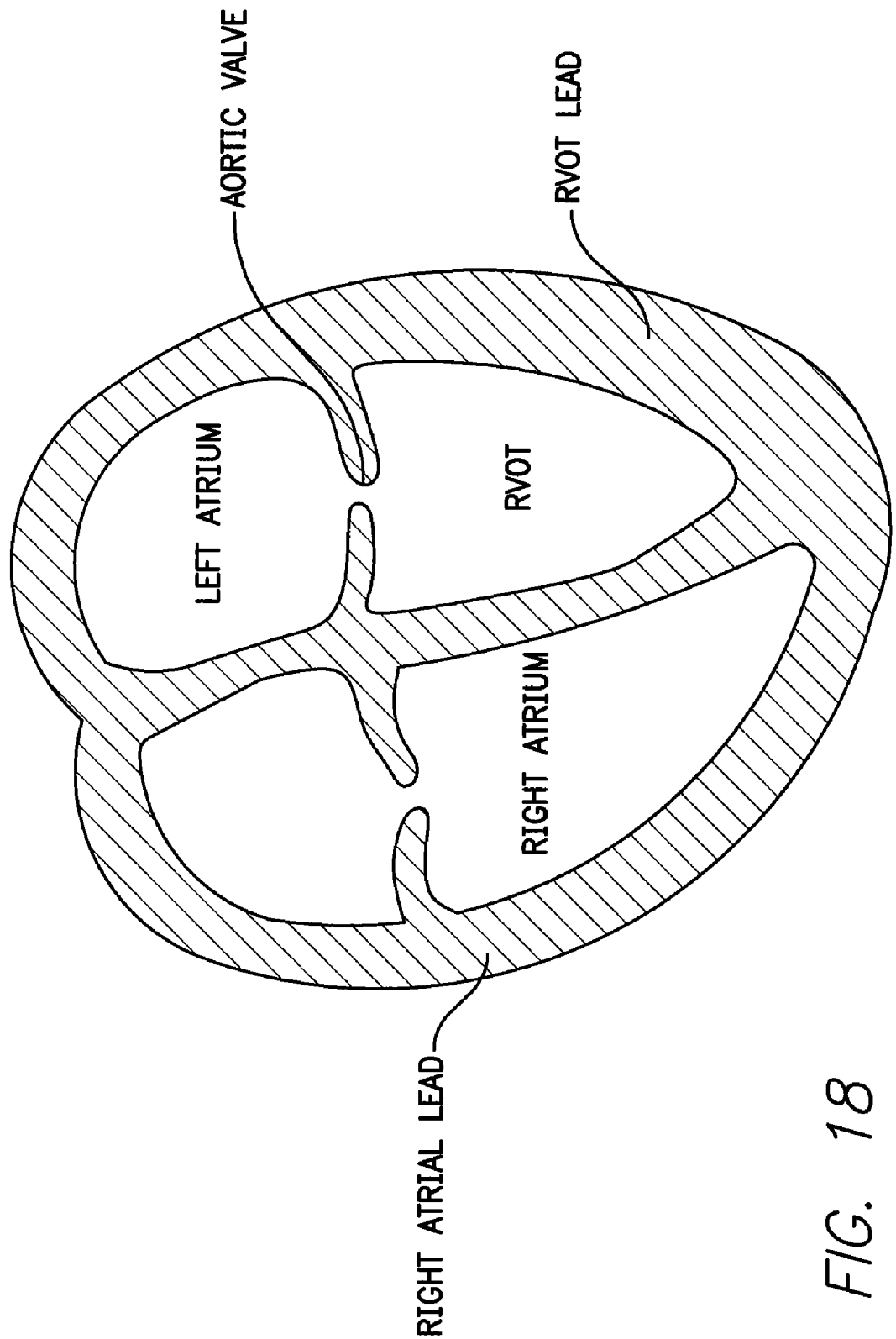
FIG. 18 illustrates cardiac chamber anatomy suitable for lead placement of electrodes that provide trans-valvular (aortic valve) impedance data.

Some valvular events can be defined by multiple sensory modalities. For example, aortic valve closure can be defined by both the A2 component of the S2 acoustic signal, and by notching on the downward slope of the impedance signal (FIG. 17a). Such notching is apparent on signals derived from extra-thoracic impedance measuring devices as well. The nature of the notch can be descriptive of specific pathologic processes such as aortic stenosis/regurgitation and decreased cardiac output. These pathophysiologic states will cause changes in the time from upslope notching (aortic valve opening) and/or downslope notching to peak impedance (FIG. 17a) and the morphology or nature of the notch itself (FIG. 17b). In one embodiment, analysis of this data can be used as part of the vital monitoring system detailing information about the aortic valve and not just timing of aortic valve events. Electrodes that traverse the aortic valve (right atrial appendage and right ventricular outflow tract) will be ideal for obtaining such impedance signals (FIG. 18). Global impedance data derived from multiple intracardiac electrodes can improve signal definition defining aortic valve events as well. Multiple integration techniques (via multi-polar electrodes) and use of summation averaging techniques for optimization purposes may improve signal processing for such impedance data. The exact time in the impedance waveform (morphologic feature of the notch) that correlates with aortic valve events can be defined using the echo interface or other implanted sensors of other modalities if impedance data alone does not accurately define this event (FIG. 17a) and such characteristics can be specified at time of initial data entry.

Characterization of the aortic valve can be done with equations designed to assess timing of aortic valve opening and closure. Delays in the time between onset of positive dZ/dt (or EGM marker) to aortic valve opening will be seen in patients with aortic stenosis:

$$\text{Aortic Valve Function} = f(AoV) = [t\,AoVo - t\,Z(0)/dZ/dt]^{-1} \quad \text{Equation 4}$$

Where t AoVo=time of aortic valve opening; t Z(0)=onset time of positive impedance slope. The units are in ohm/sec$^2$.

The function includes dZ/dt to account for cardiac output though any measurement that describes cardiac performance can be substituted for dZ/dt (e.g. ∫Z(t)dt). Low output states will cause a delay in time to aortic valve opening which will be a confounding variable and lead us to overestimate aortic valve stenosis severity. Comparisons over time in a given patient of Aortic Valve Function may lend insight into progression of aortic stenosis. Analyses of this function in large groups of patients with comparisons to other diagnostic evaluations of aortic stenosis may allow use of f(AoV) for estimation of valve area. This may require derivation of a correction factor based on such data. Similar equations can be made for assessment of aortic valve regurgitation using delays in time to aortic valve closure from either onset of aortic valve opening (systolic ejection phase) or from time of peak impedance, Z(p). Such analyses may require better signal fidelity.

Figure 19:
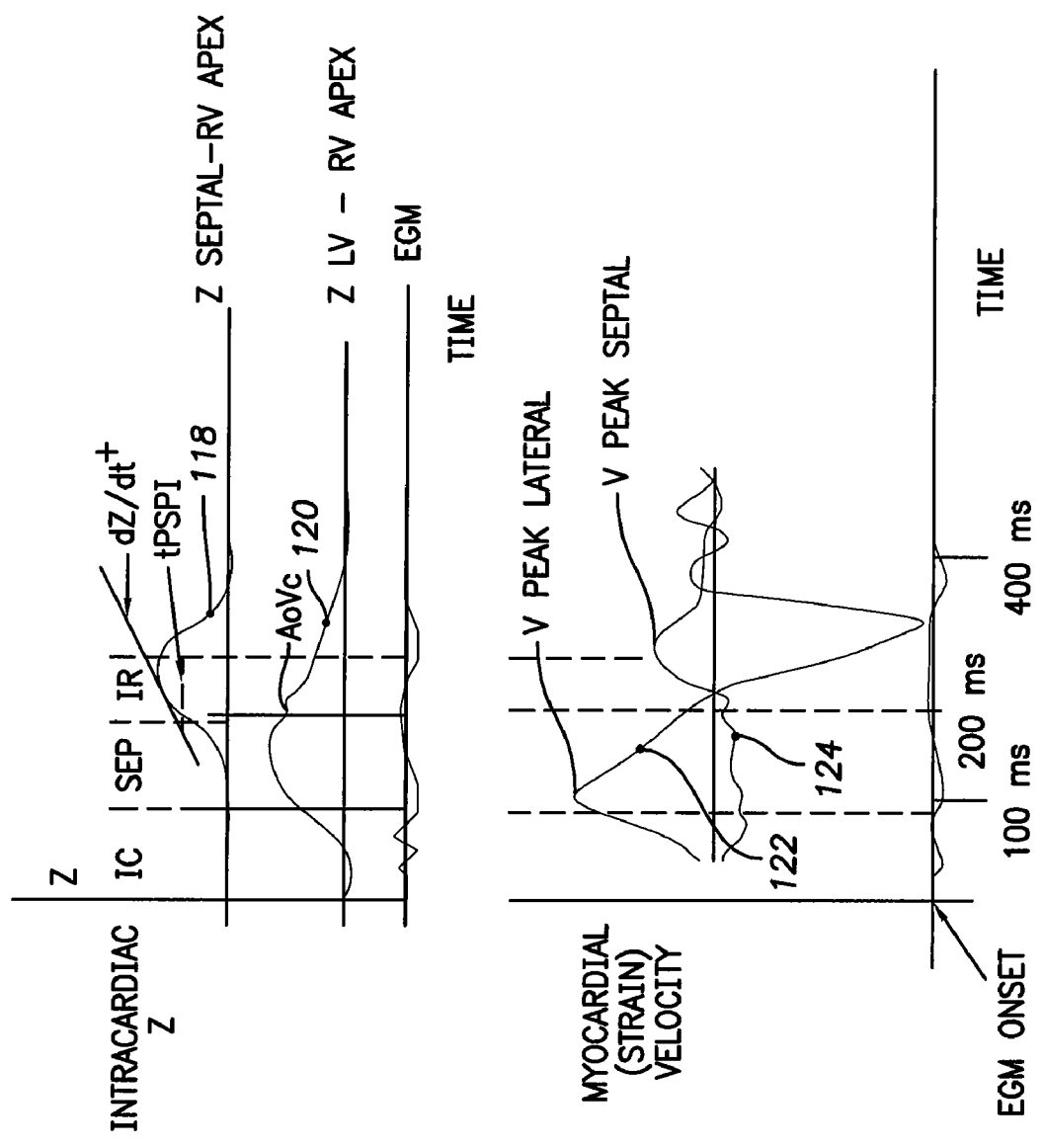
FIG. 19 depicts the relationship of impedance waveforms derived from right ventricular (RV) and LV vectors to myocardial strain (or velocity curves) representative of time to peak impedance and time of peak myocardial strain (or velocity), respectively.

Once valvular events can be identified using the impedance signal, the events can be extrapolated to any of the intracardiac electrograms signals or acoustic signals, for example, for purposes of temporal correlation with other events such as myocardial thickening (FIGS. 17a-17b and 19). Confirmation that a specific signal or summated signals appropriately identify valvular events can be periodically confirmed with an interface with echo. If signal fidelity is adequate this may not be necessary. Techniques such as doubling integration time steps (increased sampling frequency) during intervals where valvular events are historically expected to occur may help eliminate requirements for connectivity with other equipment.

Defining Myocardial Events Using Impedance Data

Mechanical myocardial systole and diastole can be identified by evaluation of impedance signals over time, Z(t) dt, as well. Z(t)dt across myocardial segments are characterized by peaks and valleys. Peaks represent peak myocardial contraction/thickening and minimal blood volume. Blood has a relatively low impedance value and maximally thickened myocardium will have peak impedance values. As Z(t)dt can be derived in specific myocardial segments between local electrodes, information about regional myocardial thickening is contained in this function. This information includes time of peak myocardial thickening and relative degrees of myocardial thickening. Such data can be used to identify changes in timing and degree of local contractility. As timing of contractility only requires identification of peak impedance for a specific segment or vector, optimal signal quality is not necessary. If signal processing optimizes a signal such that other data may be derived from the impedance signal such information can be used for the monitoring system and shed light on regional changes in myocardium (e.g. infarction). Confirmation that a specific signal or signals appropriately identify timing of regional myocardial thickening can be made through an interface with echo or within the device itself with discriminant analysis algorithms. Identification of time of peak myocardial velocity or time to peak myocardial deformation (strain measurement) using cardiac echo or other modalities will correlate to peak regional myocardial impedance (FIG. 19). Time to onset of myocardial deformation, time of minimal regional intracavitary volume or other echo parameters descriptive of myocardial events can be used as well. Ultrasonic modalities are currently available using echocardiographic equipment manufactured by companies such as General Electric, Philips and Acuson. By this mechanism the CRT can be more accurately programmed to have time to peak impedance used as a parameter for the closed loop control system. Importantly, repeated assessment of timing of valvular events with intrinsic impedance data and via the interface may be necessary after changes in interval timing have been programmed, as timing of aortic valvular events may change (e.g. shorter systolic ejection period). Such an assessment can occur within the device if adequate impedance signal quality for defining valvular events is present, or by using multi-modal data to provide a more complete characterization of the cardiac cycle.

Global Cardiac Performance Using Impedance Data

Figure 20:
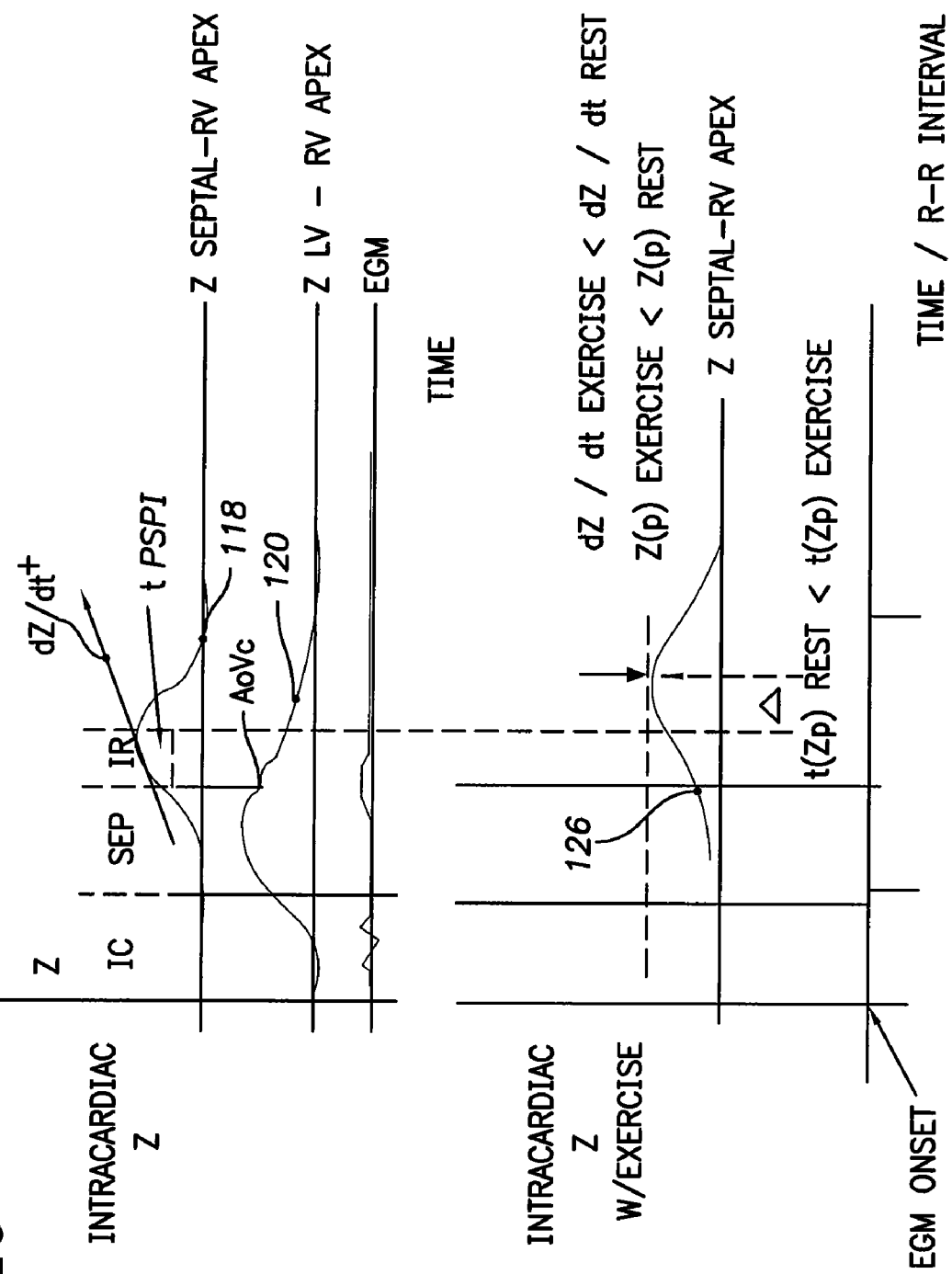
FIG. 20 shows changes in impedance waveforms with myocardial ischemia.
Figure 21:
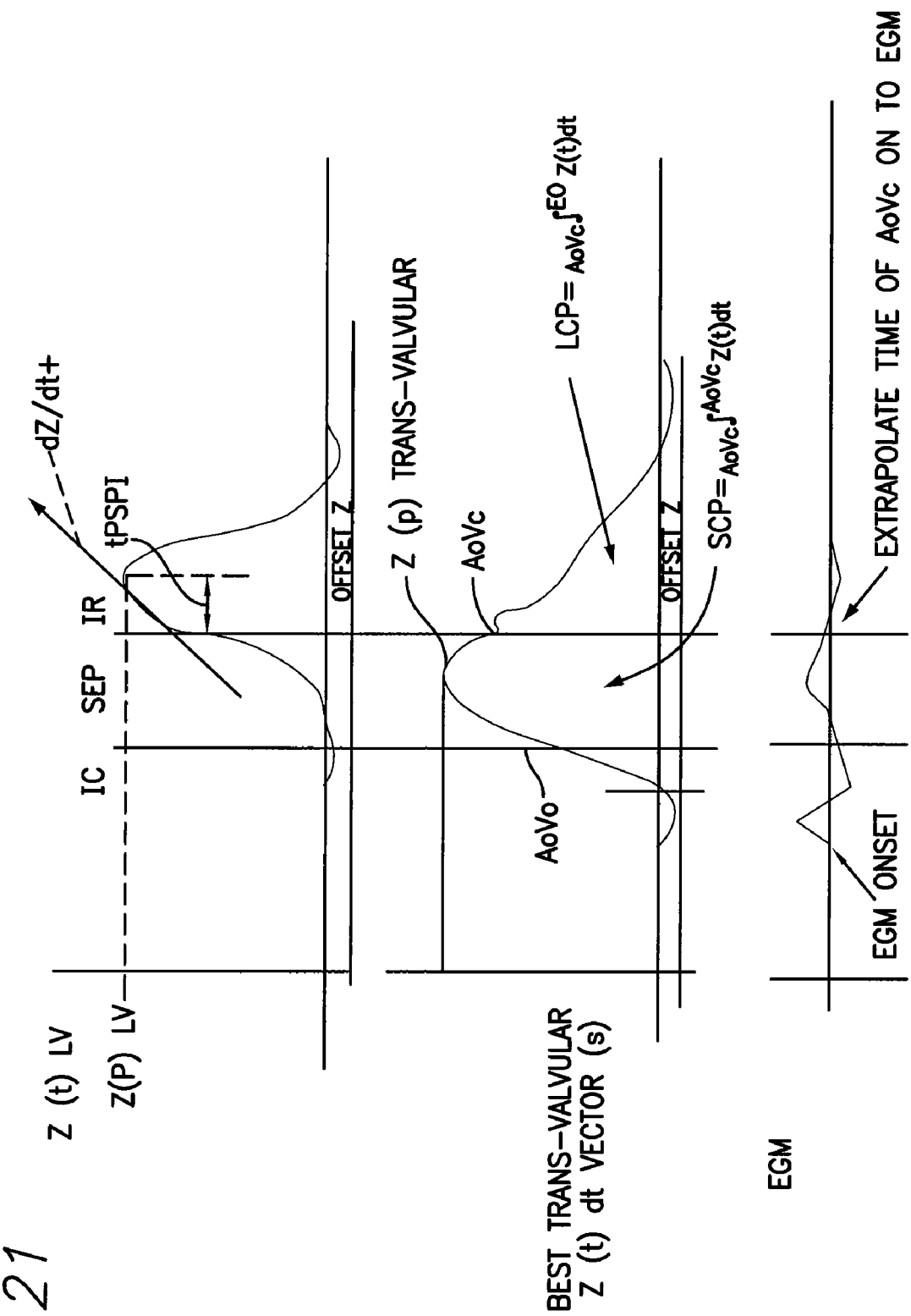
FIG. 21 illustrates various parameters of Global Cardiac Performance based on varying time limits for integration.

Global Cardiac Performance (GCP) may be determined using impedance data from internal electrode pairs/combinations (multipolar) that traverse the heart and are typically positioned at locations that allow for an evaluation of changes in impedance over time in multiple vectors. These electrodes are used to generate multipolar impedance waveforms and may be derived by simultaneously using multipolar electrodes for current delivery and measurement of voltage or techniques of summation averaging of regionally sampled impedance data (using a variety of vectors) over multiple cardiac cycles under similar conditions (e.g. heart rate, end expiration). These multipolar waveforms are less subject to signal disturbances associated with segmental myocardial impairments and delays in regional contraction, which are manifested in waveforms derived from a single vector. Analysis of the Global Cardiac Performance data can also include parameters of peak impedance, first and second order derivatives and time to peak impedance. The latter parameter requires the least amount of signal fidelity and is most useful for comparisons of time of peak contractility in dysynchronous myocardial segments (FIGS. 20 and 21).

Such morphologic characteristics will ideally provide information on systolic and diastolic properties of the patient's cardiac system. Integration techniques may be used during specific intervals of the cardiac cycle (e.g. systole), preferably defined by valvular events (e.g. aortic valve opening and closing).

Figure 23:
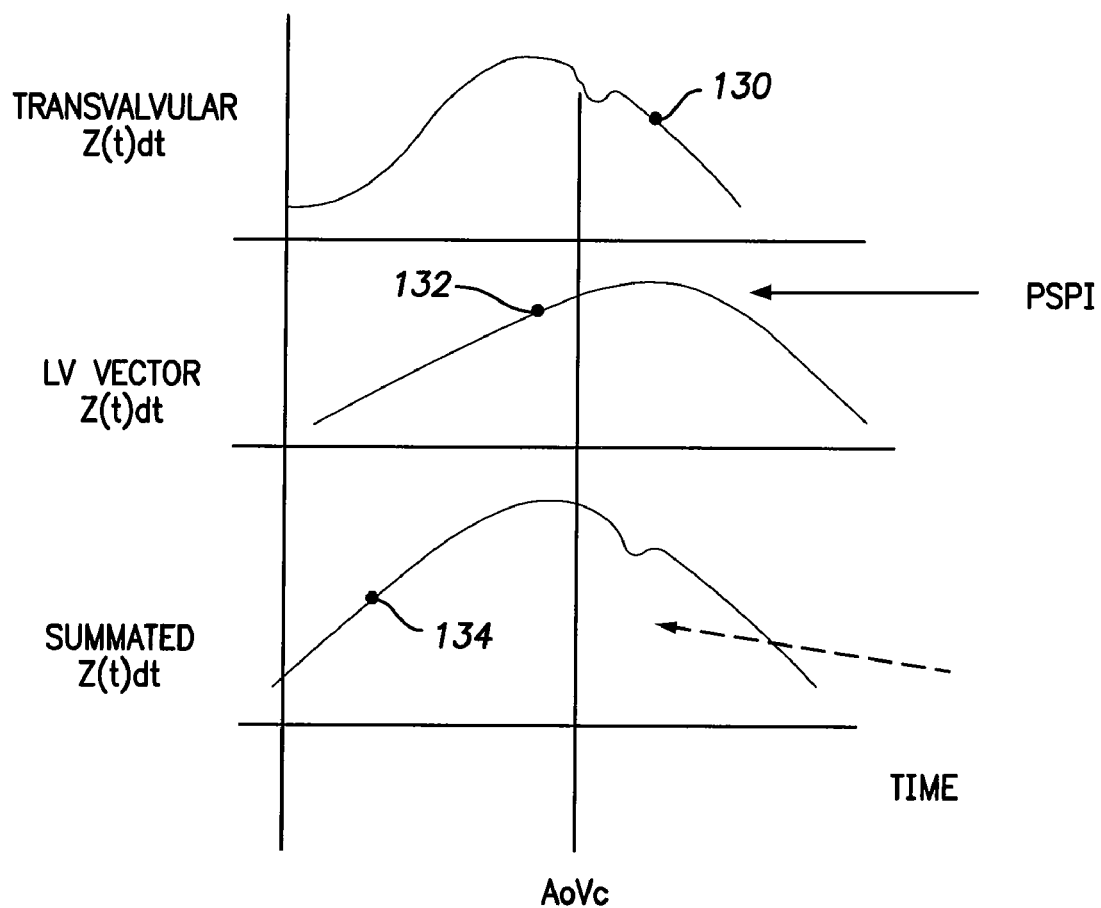
FIG. 23 shows impedance waveforms derived from RV trans-valvular electrodes and LV electrodes which have been summated to derive a more global representation of cardiac performance and dysynchrony.
Figure 24:
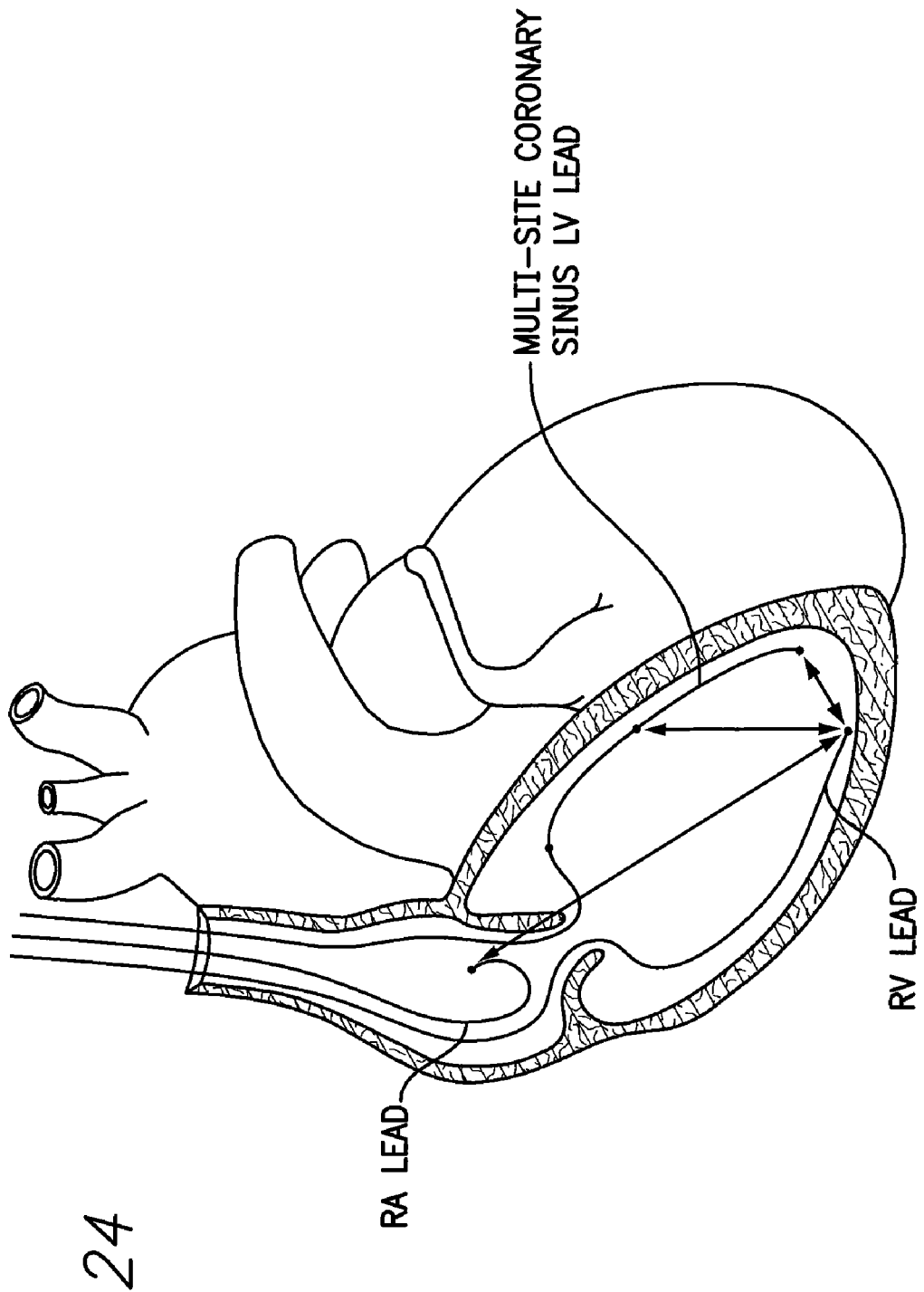
FIG. 24 is an illustration of multipolar impedance signals from triple integration techniques of data acquired in 3 dimensions.

In situations where Z(t)dt is of greater fidelity, more specific information that relates to systolic and diastolic myocardial properties may be derived from the impedance waveform rather than, for example, the time of peak impedance or value of peak impedance (FIG. 22). Such waveforms can also be derived from regional impedance waveforms between one set of electrodes but if possible the data should be reflective of changes in impedance, Z(t)dt, in a global fashion (Global Cardiac Performance) between multiple electrodes (multipolar). Multipolar data acquisition can, but need not, occur simultaneously. For example, right heart Z(t)dt (RA ring and RV tip for current delivery electrodes with RA tip and RV ring as voltage measuring electrodes for derivation of impedance) can be acquired over C cardiac cycles with ensemble averaging techniques. This can then be repeated between the LV and RV apical electrodes and SVC and LV electrodes in a similar fashion. This data can be used for defining regional properties (RA to RV tip representing RV and LV inferior-basal wall) or global properties by summation averaging or integration of regional impedance waveforms as to derive global impedance waveforms (FIGS. 23 and 24). The more global the representation of impedance data, the more information is obtained that relates to both overall cardiac performance and dysynchrony.

Systolic Cardiac Performance

Pure systolic function can be described using impedance data gathered during myocardial thickening. This can be defined as systolic cardiac performance, SCP. Integration of impedance from the onset of systole (or ideally time of aortic valve opening) to time of peak contractility (or ideally aortic valve closure) in one or more vectors would be a specific means of accomplishing this (FIG. 21):

SCP(t)=∫Z(t)dt            Equation 5 where t is either measured from onset of systolic contraction, t=0, to peak contraction, t=p or preferably during the systolic ejection phase if aortic valve events are defined.

In other embodiments, global systolic cardiac performance is assessed using electrical impedance cardiograms obtained from externally applied impedance sensors. External electrical impedance measurements may be used alone or in conjunction with intracardiac impedance data. In some instances, external electrical impedance measurements may be affected other factors such as by changes in posture and characteristics relating to pulmonary circulation.

Lusitropic Cardiac Performance

Integration of impedance during diastole will yield data relevant to myocardial relaxation. This would represent the diastolic or lusitropic cardiac performance, LCP (FIG. 21):

LCP(t)=∫Z(t)dt            Equation 6

The time frames for integration will be between aortic valve closure and onset of myocardial thickening as defined by onset of dZ/dt+. Alternatively (if valvular events are not defined), it can acquired between time of Z (peak) and Z baseline, though this would also comprise impedance values related to myocardial thickening and be less pure. Optimal lusitropy or diastolic relaxation should occur in short order without post-systolic thickening. Post-systolic thickening is an ultrasonic marker of diastolic abnormalities and in its presence, LCP will be a greater value as myocardial segments which are thickening after aortic valve closure will increase impedance values when dZ/dt− should be a steeper negative slope. Measurements of dZ/dt itself after Z (peak) [dZ/dt$^-$] can also be used for assessment of lusitropic properties and incorporated into such analysis much in the same way dZ/dt+ relates to systolic properties.

As a larger area under the initial portion (or ideally during the systolic ejection phase) of the impedance curve will denote better systolic cardiac performance, a smaller area under the latter portion of the impedance curve will indicate more optimal lusitropic properties without regional post-systolic myocardial thickening (i.e. post-systolic positive impedance, PSPI). In circumstances where there are regional delays in myocardial thickening the value of LCP will increase secondary to post-systolic contractility in dysynchronous segments (FIG. 23). Ideal representation of this data could be derived by assessing a systolic-lusitropic index, SLI:

$$SLI = \frac{\int Z(t)dt \text{ systole}}{\int Z(t)dt \text{ diastole}} \quad \text{or} \quad \quad \text{Equation 7}$$

$$SLI = \frac{SCP}{LCP} \quad \quad \text{Equation 8}$$

As contractility improves the numerator will increase and as lusitropic properties improve the denominator will decrease. As overall systolic and diastolic function is optimized the SLI will increase. Use of other data such as first and second order derivative data or slopes of impedance curves during systole and diastole would provide complementary information which can be independently evaluated or even incorporated into equations relating to cardiac performance as well.

Defining the time of aortic valve opening and closure on the impedance curve (potentially visible as notching) will be better defined with higher frequency current pulses as to better delineate systolic and diastolic time frames and more importantly, allow for the determination of post-systolic myocardial thickening, PSMT. One can reduce and potentially eliminate PSMT by delivering pre-excited stimuli based on correction factors obtained in such a fashion. If pre-excitation occurs to the electrode pair which is delayed by Pt PSPI (time of post-systolic impedance) relative to the time where a specific region has an appropriate time of initial depolarization/myocardial thickening, conditions of synchrony are likely to be met (FIG. 21 top).

The vector or vectors from which this data is obtained could represent regional or global properties. If the RV tip to RV coil is used, this data will be more representative of RV function. If the LV tip to can is used this would be more representative of LV function. Use of more than one vector (multi-polar electrodes) would provide more multi-dimensional data and represent global cardiac performance, GCP. This can be represented by using multiple integral equations (e.g. FIG. 24—triple integration).

The above data can be acquired by delivering current pulses between the RV tip and can and measuring voltage between the RV ring and RV coil in order to obtain RV impedance curve data. Similarly, one can deliver current between the RV tip and can and derive impedance curve data using voltage measured between the RV ring and LV tip. Delivering current between the RV tip and SVC/can electrodes while measuring voltage between the RV ring and RV coil as well as RV ring and LV tip would provide more global data either with or without use of multiple integrals. Multiple methods and vectors can be used for delivering current, measuring voltage, and deriving impedance curve data. The general principle is that this technology can be used for both regional and global assessments of cardiac systolic and diastolic properties as described above. Such data can be used for monitoring purposes and for assessing optimal timing intervals for multi-site resynchronization devices. Multi-polar impedance data may be used for evaluation of Global Cardiac Performance and may be incorporated into algorithms that comprise the closed loop control system.

In order to further optimize the clinical relevance of data derived in this fashion, implementation of respiratory impedance data may be used. This can be obtained by analysis of impedance between the SVC coil and can which reflects peri-hilar congestion. Alternatively, this can be obtained from analysis of baseline offset impedance as described above. Current delivery between the RV coil and LV tip would be somewhat parallel to derived voltage data between the SVC and can and would allow the system to acquire single impulse impedance measurements as well as impedance curve determinations in a peri-hilar vector, though any combination of vectors may be used for either current delivery and voltage/impedance determinations. Use of lower frequency current pulses would serve as a low pass filter reducing the contribution of myocardial properties to such data. One can use any vector to acquire this data though perihilar impedance will be more sensitive. As a more euvolemic state will correlate with higher impedance values, transpulmonic impedance data can be incorporated into the numerator (i.e. multiplication) of the above equations to derive a representation of global cardio-respiratory performance, GCRP:

$$GCRP = [\int Z(t)dt \text{ transpulmonic}] \cdot [SLI] \quad \text{Equation 9}$$

It would be more suitable however to normalize real time Ztranspulmonic to baseline measurements that are made when a patient is clinically euvolemic. Determination of euvolemia can be made with invasive measurements of pulmonary capillary wedge pressure or based on clinical assumptions of fluid status. As such, we define the transpulmonic impedance index, TPI:
Equation 10:

$$TPI = \frac{\int Z(t)dt \text{ transpulmonic (real time)}}{\int Z(t)dt \text{ transpulmonic (euvolemia)}} \quad \text{Equation 10}$$

Isolated measurements of transpulmonic impedance can be made at end expiration and end diastole and averaged rather than by integrating the offset impedance over a specific time frame. Incorporation of this data into equation 4 yields a more appropriate representation of GCRP:

$$GCRP = (SLI) \cdot (TPI) \quad \text{Equation 11}$$

where TPI reflects transpulmonic impedance in real time normalized to euvolemic transpulmonic impedance. Euvolemia can be most easily and accurately determined by using the greatest value of transpulmonic impedance (lowest thoracic fluid volume) since the prior time of periodic interval monitoring. It is worth mention that lower values of transpulmonic impedance (increased thoracic fluid content) may result in better cardiac performance as a result of more optimal Starling's forces seen with slight elevations in pulmonary capillary wedge pressure and LV end diastolic pressures. In one embodiment, this optimal transpulmonic impedance value can be derived at a time when patient has had invasive monitoring of such clinical variables or by correlating the optimal transpulmonic impedance value to a time when measurements of Global Cardiac Performance are ideal (e.g. SLI). Changes in transpulmonic impedance that occur with variations in heart rate and respiration need to be accounted for. This can be done by triggering acquisition of impedance data for calculation of these indices during similar conditions (e.g. same heart rate and minute ventilation).

Graphic representation (trend data) of GCRP, SLI, TPI, SCP and LCP will allow the practitioner to make valuable clinical assessments between office visits. Such data can be averaged over 24 hour periods (or other time frame) using periodic interval monitoring. Periodic interval monitoring (PIM), described below, can also be used as part of the control system where the effects of changes in interval timing are analyzed using any of the GCP parameters described above. Such analyses need to account for heart rate. Ideally, measurements made through PIM can be done under similar conditions (e.g. end-expiration). This will improve signal to noise ratios and allow for appropriate comparisons.

Periodic Interval Monitoring—Analysis Activation

Periodic Interval Monitoring (PIM) at programmed intervals (e.g. every hour) occurs within the CRT. PIM serves to activate analysis of impedance, acoustic and other data if optimal conditions for such analysis exist. Optimal conditions include the patient being at rest (unless impedance signals during exercise have been previously determined to be adequate), and during periods of relative hypopnea/apnea. Use of a blended sensor such as an accelerometer and minute ventilation sensor can be used to define end-expiration or if possible a period of hypopnea/apnea where band pass filters can most easily eliminate impedance signal data related to changes in thoracic volume and cardiac translation within the thorax.

Data acquisition can occur during intrinsic rhythm or during active pacing. For example, recently developed pacemakers utilize impedance data during pacing as to define the inotropic state of the heart. These pacing systems (Biotronik—closed loop system) adjust rate responsiveness based on a derived inotropic index, and are well known in the art. Defining intrinsic electromechanical properties (dyssynchrony) initially will serve to direct the system to appropriately pace myocardium and cause resynchronization. This will need to be analyzed thereafter at periodic intervals during pacing as to confirm that adequate resynchronization is occurring. This can occur during pacing using electrodes that describe global cardiac properties or electrodes which have vectors that are similar to the electrodes used for stimulation. Techniques may be used to implement the same electrodes that are used for stimulation for data acquisition of impedance waveforms as well. Alternatively, and additionally, pacing may be terminated for reassessment of pathologic electromechanical properties with repeat adjustment of interval timing at periodic intervals.

Stochastic Optimal Control System

Figure 25:
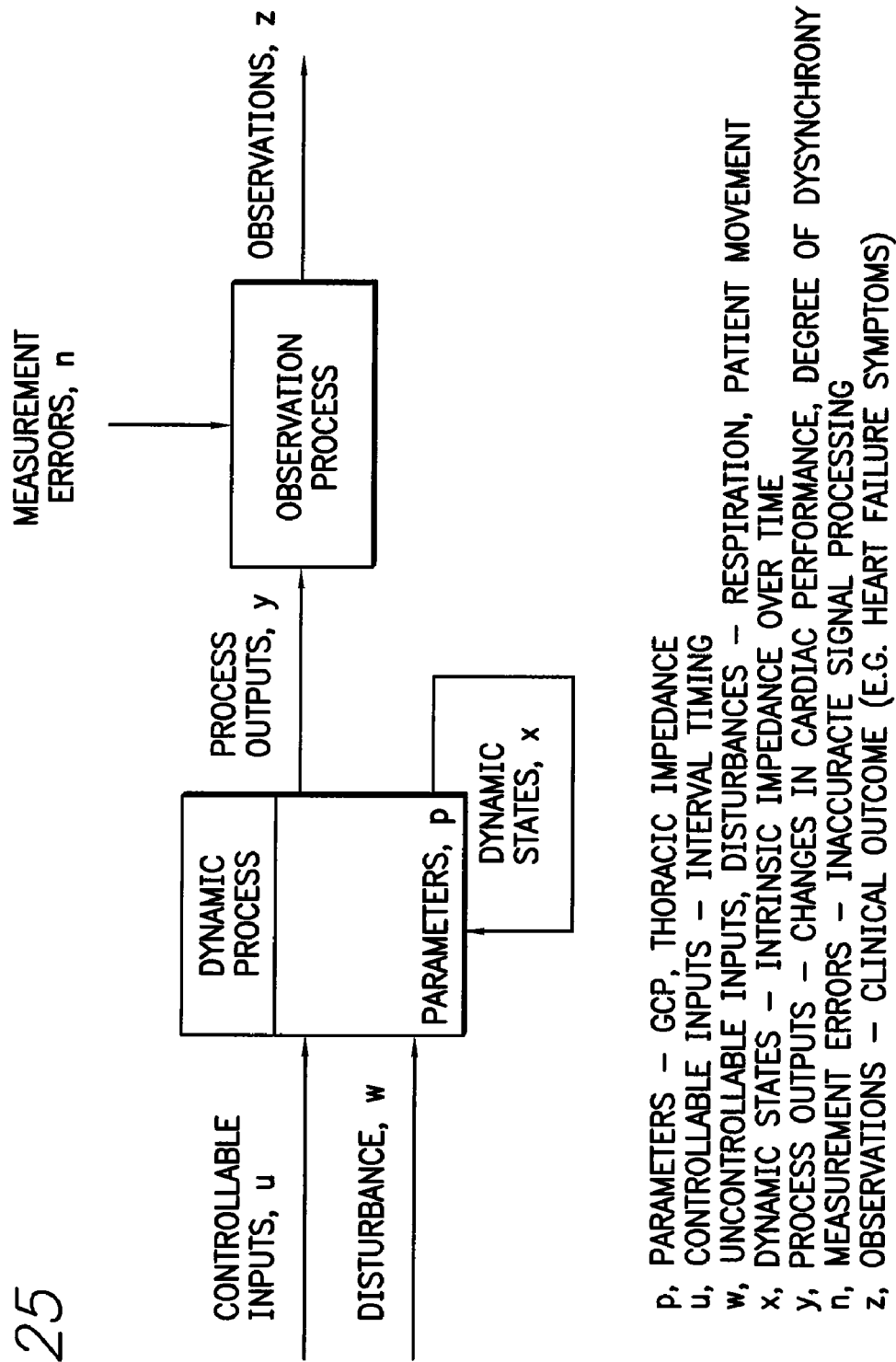
FIG. 25 is a representation of one embodiment of stochastic optimal control system that may be used with cardiac resynchronization therapy devices.

The control system evaluates a family of variables as to achieve the outcome of improving a patient's congestive heart failure symptoms and long-term prognosis. Such a control system falls into the category of a Stochastic Optimal Control System (FIG. 25). In order to achieve optimal control, the system must recognize disturbances such as impairments in impedance signal fidelity. Multivariate statistical analysis techniques (described below) will serve this purpose. Controllable inputs to the system are changes in interval timing. Uncontrollable inputs are respiration, cardiac translation and patient movement. Use of blended sensors to determine time of data acquisition and determination of time frames of cardiac translation where data sampling is minimized will help optimize the control system. In this fashion, the dynamic states measured by the system (e.g. Z(t)dt) and derived parameters (e.g. GCP) will be utilized as to direct programming of interval timing as to optimize process outputs (e.g. cardiac performance, resynchronization) and improve clinical outcome.

Automatic Optimization Algorithm

Figure 26A:
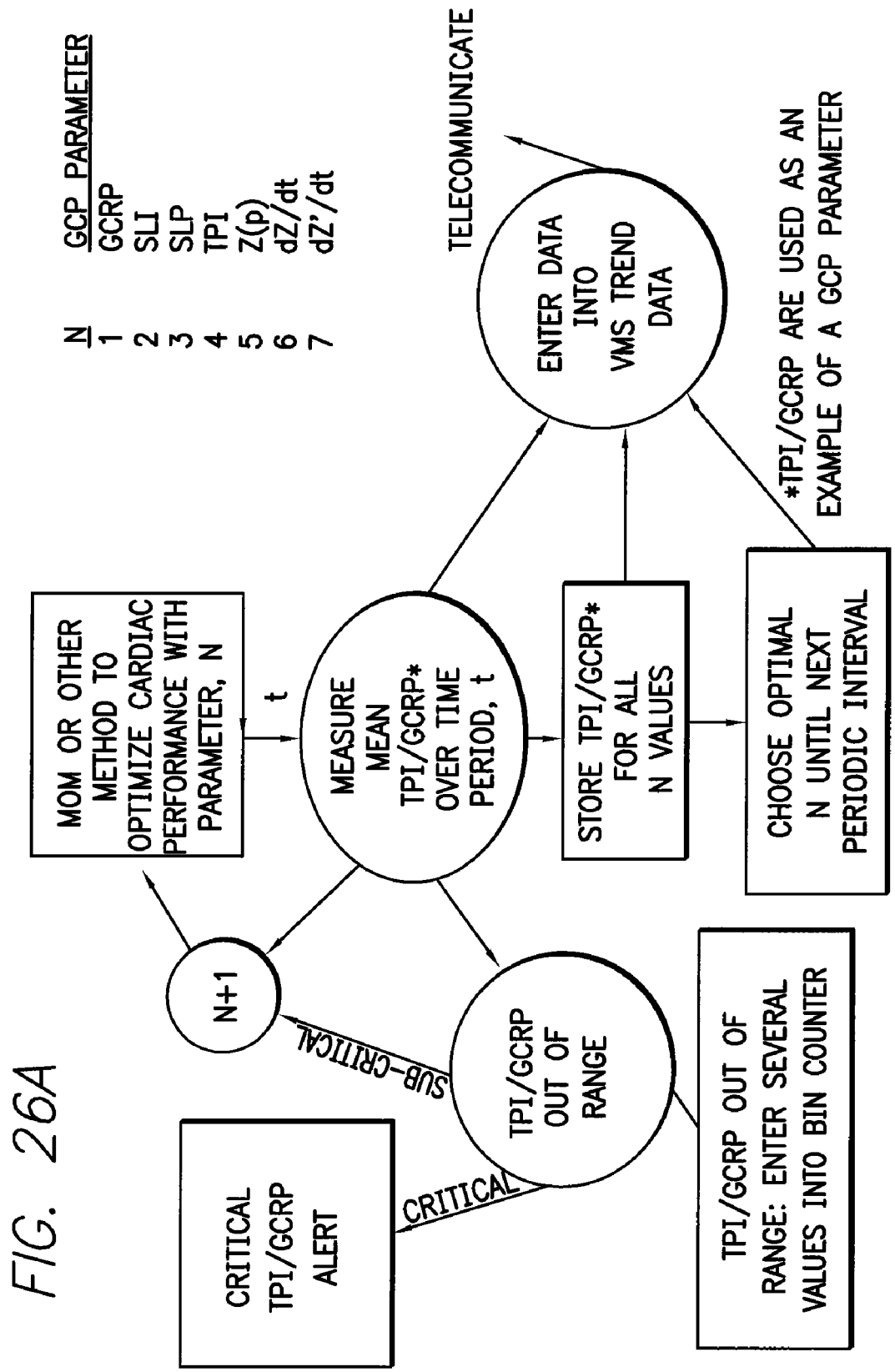
FIG. 26a illustrates the functioning of the Automatic Optimization Algorithm (AOA) with parameters reflective of Global Cardiac Performance, GCP.
Figure 26B:
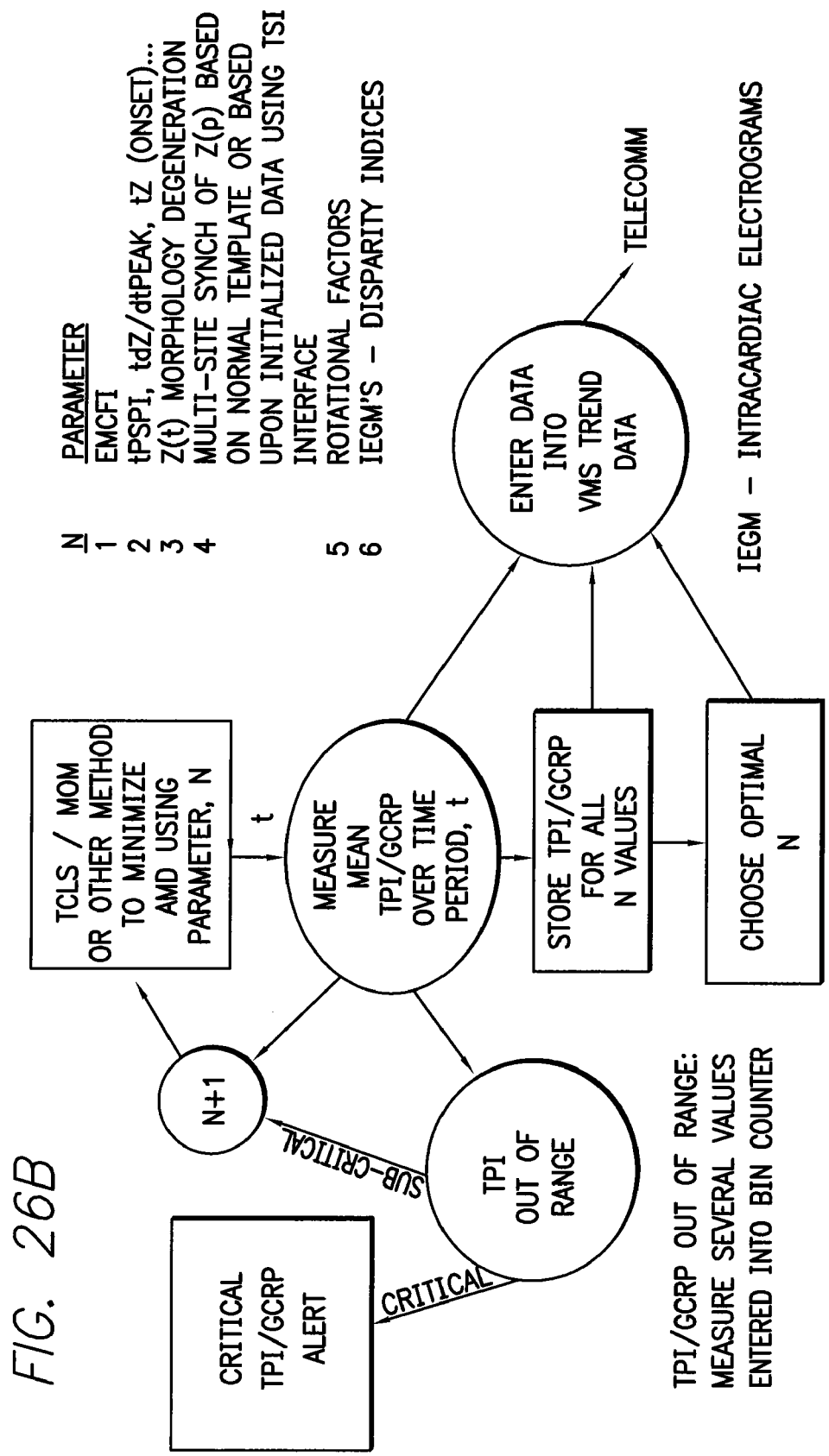
Figure 26C:
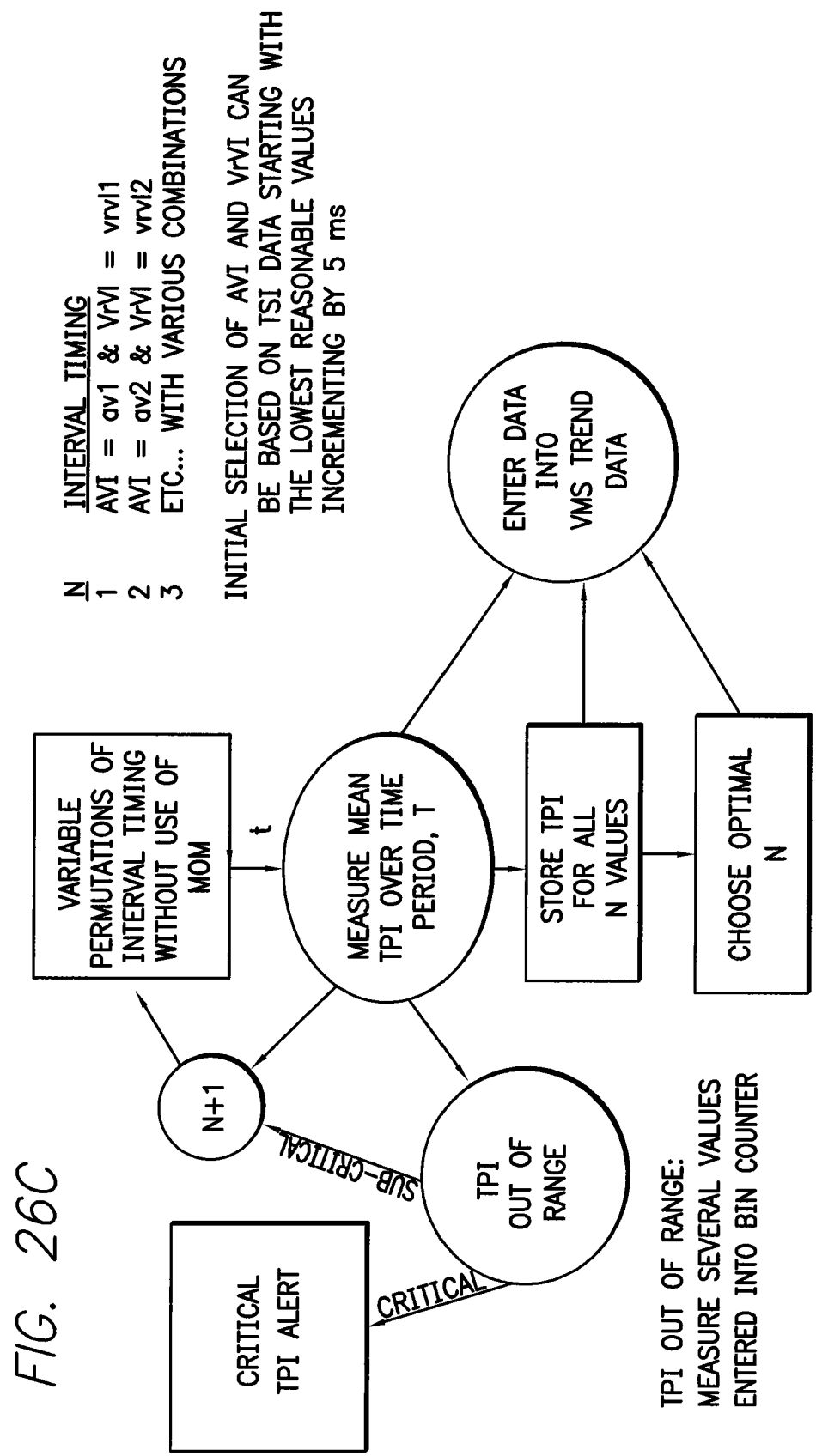
FIG. 26c illustrates how an AOA can use measurements of transpulmonic impedance to evaluate the efficacy for any given set of interval timing without need for higher fidelity data.

Automatic Optimization Algorithms (AOA) evaluates the effectiveness of programmed CRT interval timing over specific intervals of time and serves as an overseeing control system. The AOA can evaluate Global Cardiac Performance using intrinsic measurements of impedance (e.g. dZ/dt, peak Z, integrals of Z(t)dt with varying limits, Z offset (thoracic fluid volume)). This is described in greater detail in U.S. Pat. No. 7,065,400, and is depicted in FIGS. 26a-c. Which parameters are evaluated depends on signal fidelity as discussed above. The AOA can parameter switch as needed though the clinically most useful parameter should be utilized whenever possible (e.g. GCRP). Discriminant analysis or other techniques will serve to direct the switch of parameters utilized in the control system. Parameters such as EMCFI describe dysynchrony. Time to peak dZ/dt and time to onset of Z(t)dt are alternate parameters of dysynchrony that can be used if the time of the peak impedance value can not be defined. Ideally parameters representative of Global Cardiac Performance that relate to synchronization and cardiac performance can be utilized (FIG. 26a). Parameters that describe timing and synchronization alone (FIG. 26b) will be suitable but do not represent as much clinically relevant information. In circumstances where no parameter can be used because of inadequate impedance signals, specific sets of interval timing may be tried over specific time frames while trends in transpulmonic impedance are evaluated (FIG. 26c). In this situation the MOM will not be utilized as no cardiac performance parameter can be optimized.

If a sub-critical circumstance arises then the Automatic Optimization Algorithm will cause a parameter switch so that a different parameter is used for overseeing the system which may be more effective for evaluation of the clinical response to CRT interval timing. Such parameter switching may be necessitated if signal fidelity does not allow use of a specific parameter as well. The AOA can modify interval timing to a default setting or if a critical circumstance arises an emergency default pacing modality can be implemented.

Vital Therapeutic System—Crt Interval Timing

Figure 27:
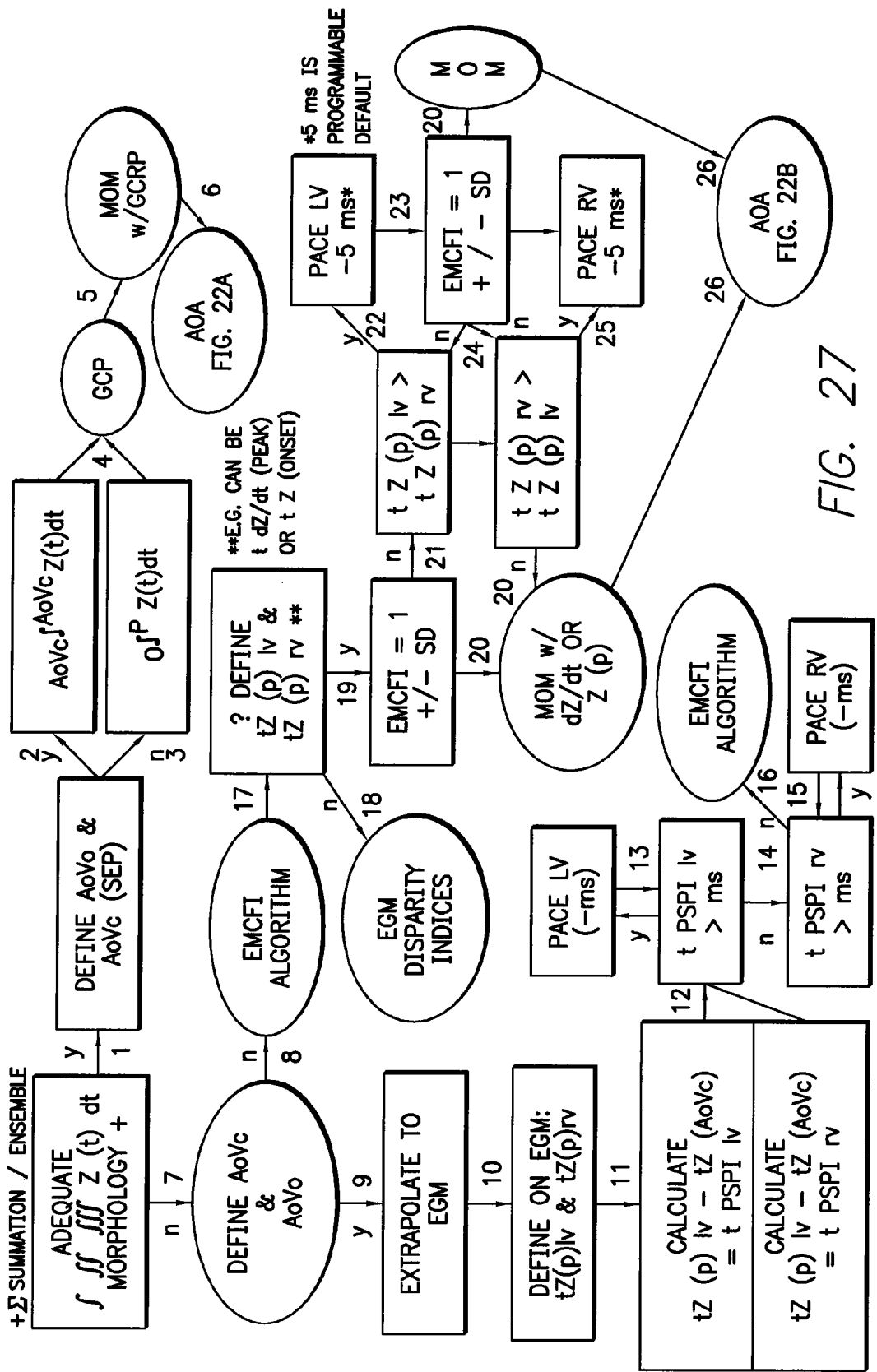
FIG. 27 is a flow diagram for the Vital Therapeutic System, VTS, and details how interval timing is modified using a variety of techniques based on the degree of signal fidelity.

The methodology employed to modify interval timing is illustrated in FIG. 27. This has similarities to the AOA whereby the higher fidelity impedance data yielding the most clinically relevant data is utilized to direct CRT timing. In the circumstance where measurements of Global Cardiac Performance parameters can be utilized (step 1), signals of the higher fidelity, descriptive of Z(t)dt morphology, can be implemented. If valvular events are identifiable (step 2), the VTS may use integration techniques over systole and diastole to derive parameters of Global Cardiac Performance (step 4). The system will then use such GCP parameters in the Matrix Optimization Method, step 5, and for the Automatic Optimization Algorithm (step 6 and also depicted in FIG. 26a). The specific parameter optimized, CPPo, will ideally reflect both cardiac performance and dysynchronous properties. If systolic and diastolic time frames can be determined, the parameter used will be the SLI. This data can be supplemented with measurements of the TPI and the GCRP can be used in the best of circumstances. The set of interval timing which maximizes GCRP is then programmed. If needed, parameter switching can occur (e.g. inadequate characterization of diastolic time frames) and a pure measurement of systolic function such as SCP or even Z(p), peak impedance, can be evaluated at any programmed interval timing. If valvular events are not identifiable but the impedance waveform morphology is adequate, integration techniques over relative systolic and diastolic time frames will occur from time of onset of the positive slope (upward deflection) of the impedance signal, Z(0)dt to peak Z, Z(p)dt, and from time of Z(p)dt to the time when Z(t)dt reaches its baseline value, respectively (step 3).

If signal morphology is intermediate but valvular events can be defined (step 7), time of post-systolic positive impedance can be determined and used to make a gross change in interval timing (e.g. pre-excite the appropriate electrode as to cause t PSPI to be ≦0). If valvular events are not identifiable but time of peak impedance is determined then the EMCFI algorithm is utilized (step 8). The EMCFI algorithm is less ideal, for example, as RV and LV timing may be synchronous but after aortic valve closure (global electromechanical delays). Use of additional control systems such as MOM and the AOA will help optimize interval timing programmed in this fashion. The EMCFI algorithm however is capable of more fine tuning than the t PSPI algorithm. After the t PSPI algorithm has caused pre-excited stimulation as to insure stimulation during the systolic ejection period, further optimization in timing can occur using the EMCFI algorithm. The t PSPI algorithm can be ideally implemented at time of initial data entry during intrinsic rhythm and further modifications in interval timing can occur using the EMCFI algorithm thereafter.

Eliminating Post-Systolic Postitive Impedance Time (tPSPI)

In step 9, time of aortic valvular events are extrapolated to the intracardiac electrogram, IEGM, used as a reference. In step 10 time of peak impedance in the specific vectors subject to synchronization (e.g. LV and RV) are extrapolated on the reference IEGM. A calculator then determines the t PSPI for each vector in step 11. In steps 12 to 15, changes in interval timing for stimulation of electrodes in these vectors occur until peak myocardial impedance is no longer post-systolic but occurs during the systolic ejection phase (step 16 and also depicted in FIG. 19). A similar algorithm can be employed in circumstances where there is pre-systolic positive impedance.

Emcfi Algorithm

The EMCFI algorithm will require less fidelity than either the GCP or t PSPI algorithms. This algorithm will necessitate identification of time of peak impedance (step 17). If this is not possible (step 18), the system can use Disparity Indices derived from IEGMs obtained in various vector combinations (see Electrogram Disparity Indices). Once time of Z(p) is determined the system calculates the EMCFI (step 19). If the EMCFI approaches unity (step 20) the set(s) of programmed interval timing that cause EMCFI to approach one +/− a given standard deviation are used in MOM (step 20) with the highest fidelity impedance parameter possible (e.g. Z(p) or dZ.dt). If EMCFI is not close to unity, changes in interval timing occur until EMCFI approaches unity (steps 21 25). After interval timing that corresponds to CPPo using MOM is programmed the AOA serves to oversee the system as an additional control at periodic intervals (step 26).

In an alternate embodiment, equations that describe the relationship between relative times of peak impedance and stimulation patterns (varying interval timing) can be utilized to more readily determine the appropriate delay times between current delivery in the specific vectors. Such an equation can be more readily derived by using the echo interface and will likely be exponential in nature. The exponent will be a different number during increases in heart rate that may occur with exercise. Such a change in the equation will require analysis of electromechanical relationships during exercise or inotropic stimulation. The device can autonomously derive this equation and if changes in the equation becomes necessary (evidence of increased dyssynchrony) the DMS can alert the physician that a patient's clinical status has changed.

In another embodiment, measurements of cardiac performance such as a determination of inotropy (e.g. dZ/dt or SCP) can be made with impedance signals and serve to modify which equations are used to direct interval timing. These equations would have to be individualized and based on either data acquired with an echo interface or by historical values of time to peak impedance at different sets of interval timing under varying inotropic states.

Figure 28:
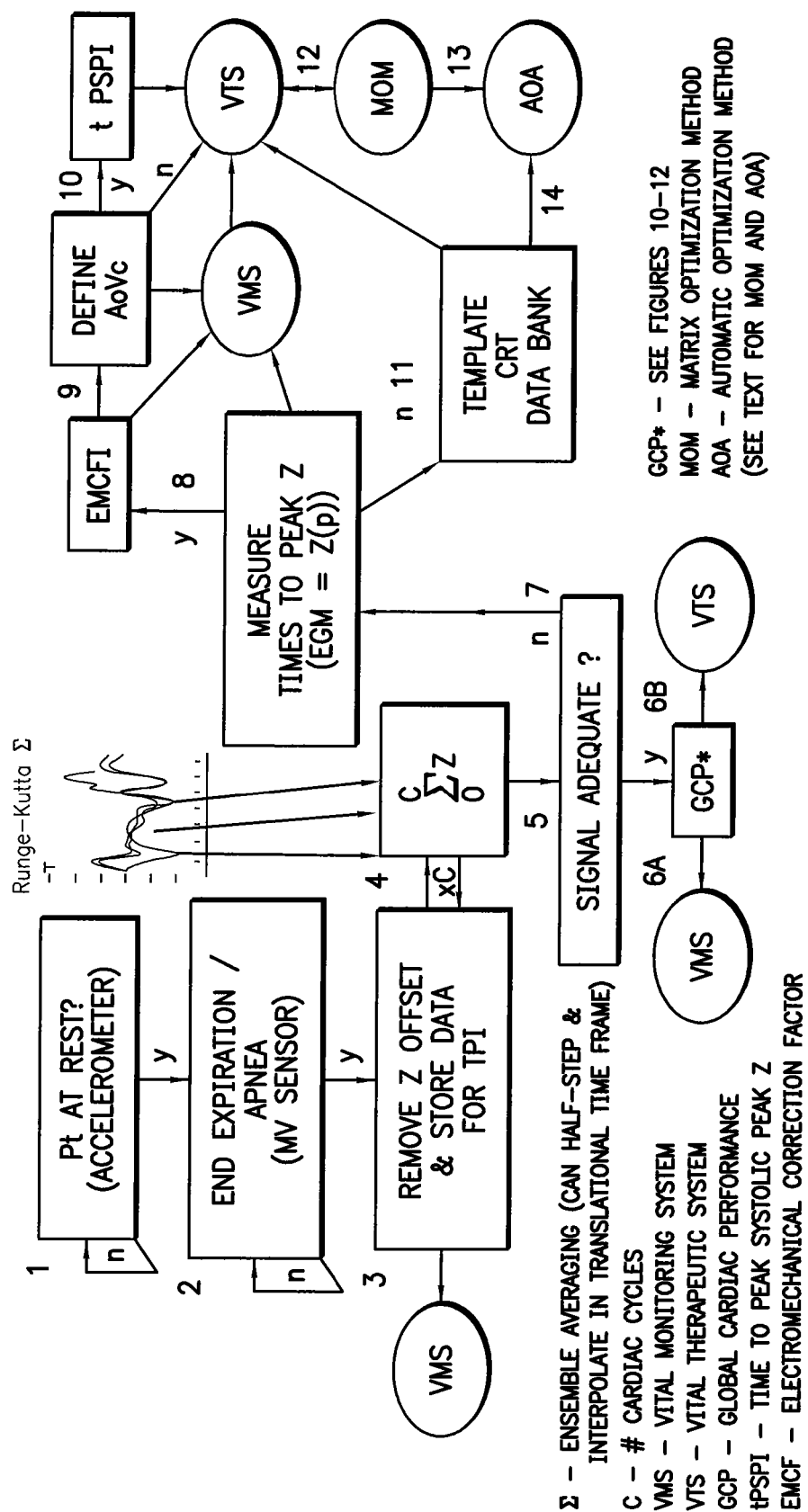
FIG. 28 illustrates how the dynamic control system acquires impedance data, determines signal adequacy and chooses which parameters to use for optimization of interval timing and monitoring purposes.

In circumstances where impedance data is not able to be used at all the system can use an alternate means of optimizing timing that relies on assessment of a disparity index based on intracardiac electrograms (see below), or based on predetermined defaults as depicted in step 11, and in FIG. 28. The AOA in this case would utilize measurements of TPI as to oversee the control system.

Disparity Indices Of Intracardiac Electrograms

In an alternate embodiment, intracardiac electrograms derived from multi-site electrodes can be used for deriving a disparity index. The greater the disparity of intrinsic electrical activation patterns the more dyssynchrony is present. The disparity index can be used in a closed loop system as a parameter for determining optimal CRT interval timing. Relative timing of various features of IEGM signals will describe dyssynchronous activation patterns better than surface ECG. This is because IEGMs provide a window into activation patterns that appear fused on a surface ECG. Analysis of IEGM to derive a disparity index can include but is not limited to evaluation of relative onset of EGM deflection, time of peak and termination of EGM "R" waves, duration of EGM "R" waves.

In a non-CRT device, such a disparity index can trigger an alert to inform the physician that intracardiac electrogram signals are suggestive of dyssynchrony and that an upgrade to a CRT device should be considered. Use of the can electrode in a non-CRT device will help incorporate electrogram data that represents left ventricular activation patterns. Any number of variables that reflect relative timing of depolarization in different vectors can be used to derive disparity indices for such an embodiment.

The descriptions herein relate mainly to conventional biventricular pacing systems and temporal relationships between dual site ventricular pacing stimuli. Resynchronization therapy may employ multiple electrodes for stimulation between and/or within the cardiac chambers. Optimal interval timing includes atrial-ventricular intervals (AVI) and possibly multi-site pacing with additional electrode pairs (VaVb) in addition to conventional biventricular electrodes (VrVI). AVI can be programmed based on equations described in the literature, AV optimization techniques using echo or intrinsically within the closed loop system. The details of the MOM have described in more detail above and in the parent U.S. Pat. No. 7,065,400.

Av Optimization Using Impedance Data

One example where cardiac resynchronization therapy may be utilized is in the optimization of AV timing. Ideally, atrial systole is completed just prior to aortic valve opening, AoVo. The additional ventricular filing resulting from this atrial "kick" may contribute up to about 20% of the total ventricular filling. In turn, enhanced ventricular filling or preloading causes increased ventricular ejection of blood. This relationship between ventricular filling and ventricular ejection is known as the Frank-Starling principle. In a normal heart, AV delay is in the range of about 120 msec to about 200 msec. Too short of an AV delay causes truncation of atrial systole, which reduces ventricular filling, and results in lower cardiac output due to a sub-optimal Starling curve. Furthermore, due to elevated atrial pressures at the start of ventricular systole, the atrial-ventricular pressure gradient is reduced and may potentially cause diastolic mitral regurgitation (MR). On the other hand, too long an AV delay results in a loss of atrial kick because atrial systole occurs during the early portion of diastolic filling and is offset by subsequent slower passive filling during the same diastolic phase. Excessive AV delays may also be associated with decreased cardiac performance as a result of a prolonged diastolic filling period and delayed isovolumic contraction with loss of synchrony between time of optimal end-diastolic left ventricular, LV, volume and pressure, and time of cardiac output/forward flow.

To optimize the AV interval delay, sensor-derived timing of mitral valve closure and onset of cardiac systole may analyzed as changes in interval timing are made within an implanted device as part of a closed loop system or in combination with extrinsic sensor modalities. This diastolic mechanical information may be used alone, or analyzed along with algorithms for optimizing ventricle-to-ventricle, VV, interval timing between RV, LV or multi-site leads in a CRT device to achieve optimal systolic and diastolic cardiac performance.

Figure 29:
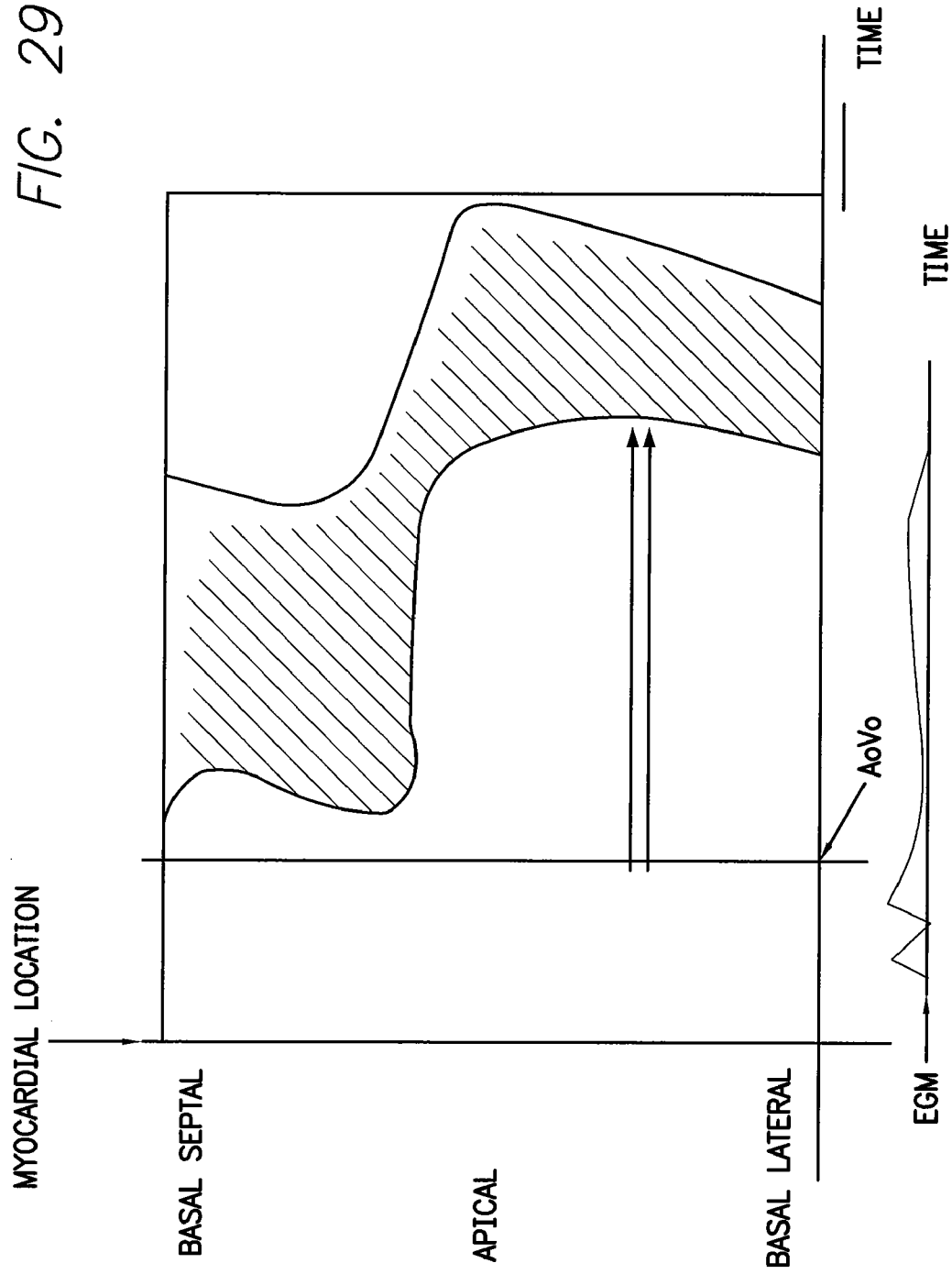
FIG. 29 is a picture of curved M mode data (General Electric) illustrating how delays in timing affect regional myocardial thickening.
Figure 30:
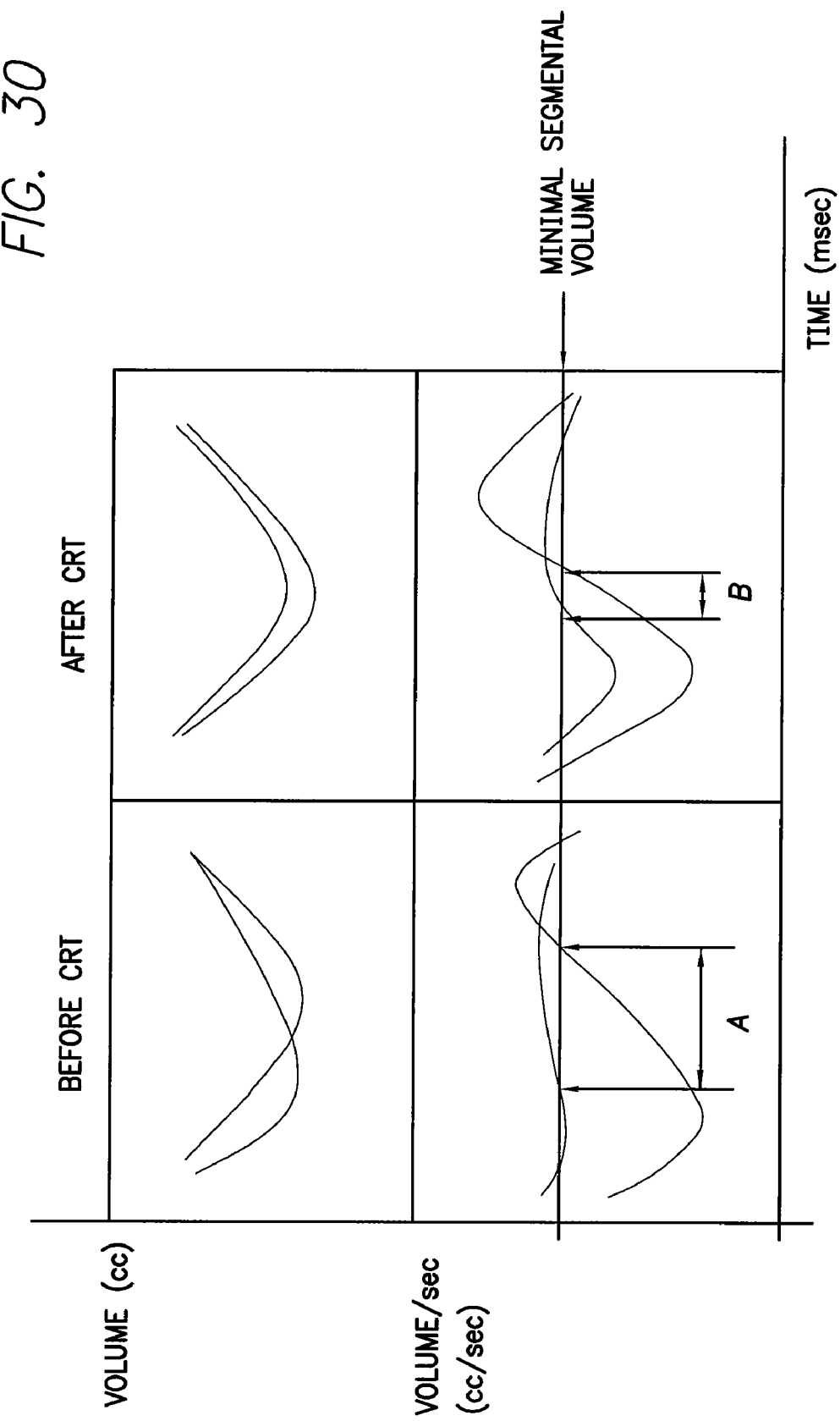
FIG. 30 illustrates how resynchronization can reduce or eliminate delays in regional myocardial thickening by analysis of charges in regional volume time curves (TomTec Imaging-Phillips).

Impedance data can be utilized for AV optimization purposes. One method of achieving this can be by injecting current impulses during the cardiac cycle and determining end-diastole when the impedance value is at a minimum. Potential limitations in the application of such impedance data for AV optimization are several-fold. Onset of initial ventricular contraction should occur after maximal filling of the ventricular chambers. This will correspond to a time frame when trans-cardiac impedance is at a nadir. Dyssynchronous hearts, however, have regional variations in mechanical end diastole. This has been demonstrated in the ultrasound literature. FIG. 29 demonstrates an ultrasound modality, curved M mode imaging. In this example, one can visualize that specific myocardial segments begin contracting (regional end-diastole) after other segments. These delays can approach 500 milliseconds. If the impedance waveforms relate to myocardial segments with delayed contractility, AV optimization can occur after aortic valve closure. Ultrasonic imaging can demonstrate this by analysis of regional changes in volume as well. FIG. 30 depicts time to minimal regional volume using Philips three dimensional echocardiographic imaging before and after resynchronization.

In order to address these limitations, one can use multiple impedance waveforms in a variety of vectors with summation averaging techniques. Alternatively, multi-polar impedance data acquisition will more accurately reflect global changes during the cardiac cycle. Electrodes with vectors that traverse the atrial chambers or great vessels will potentially be 180 degrees out of phase with ventricular events and should not be utilized for data acquisition. Ideally, AV optimization should occur after inter- and intra-ventricular dysynchrony has been minimized. In this fashion, there will be more congruence between regionally obtained impedance waveforms.

Figure 31:
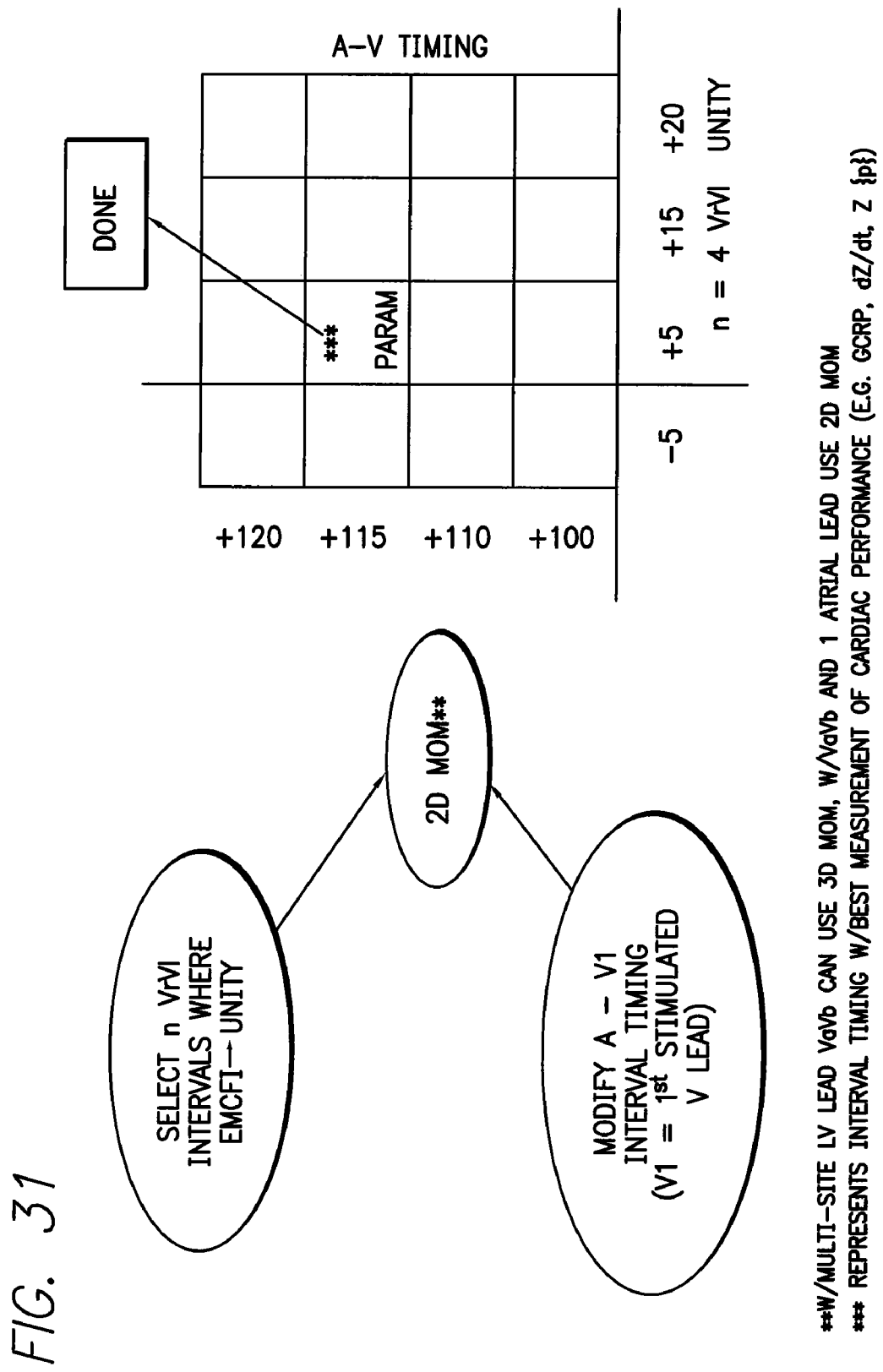
FIG. 31 shows how interval timing in a CRT device is chosen by using the Matrix Optimization Method as to derive which combination of AV and RV-LV intervals optimize a specific cardiac performance parameter.

An additional issue is that for any changes in interval timing in one dimension, further modifications in interval timing will be needed in another dimension. For example, changes in VrVI may cause a change in the systolic ejection period, which necessitates adjustments in the AVI from the time of original programming. For this to occur dynamically, the MOM algorithm can be utilized (FIG. 31 and described in U.S. Pat. No. 7,065,400). By way of example, a three dimensional mathematical array can include several permutations of AVI, predetermined VrVI where EMCFI approaches unity, and several VaVb. The parameter which best describes Global Cardiac Performance (e.g. GCRP if signal integrity is ideal or peak dZ/dt if less than ideal) will be the one optimized using this methodology. Use of these modalities for fine-tuning interval timing will optimally optimize synchrony without the pitfalls of using regionally derived impedance data as to direct AV timing.

Av Optimization Using Multimodal Sensors

Due to limitations that may exist in any one type of cardiac sensor modality (e.g. impedance, electrograms, acoustic data), use of only a single sensor type may provide an incomplete profile of cardiac function and performance. By using multimodal array of sensors, however, a more comprehensive and accurate picture of cardiac function may be achieved, allowing for greater optimization of various cardiac timing intervals.

In one example, a combination of cardiac acoustic data and intracardiac impedance measurements may be used to optimize the AV and/or PV timing interval. Sensor-derived timing of mitral valve closure is based on recognition of S1, the first heart sound. Any of a variety of transducers may be used derive the time of S1. Examples of such a transducer include but are not limited to a sonomicrometer, accelerometer, a cardiomechanical sensor (CMES) employing embedded piezoelectric material on an implanted lead or alternate piezoelectric sensor. In other embodiments, valvular events may be identified using non-acoustic mechanical sensors, including but not limited to mechanical sensors embedded in the myocardium or pressure sensors implanted to detect chamber pressures.

While cardiac sounds simplify the detection of aortic valve closure, the delineation of aortic valve opening timing, tAoVo, is more difficult to identify with cardiac acoustics. Although aortic valve opening is correlated with the cardiac systolic phase (aortic outflow) and may be evaluated using an analysis of global systolic myocardial deformation, recognition of cardiac acoustical information corresponding to systolic forward blood flow may be difficult, even when a systolic aortic flow murmur is present. Thus, other sensor modalities may be used to identify cardiac events not optimally identified by acoustic sensors.

Impedance data may be used to assess the state of myocardial contractility. However, use of regionally derived data (e.g. impedance data acquired from left ventricular, LV, electrodes) may result inaccuracies secondary to electromechanical dysynchrony in a regional vector. Inaccuracies may result from ventricular wall infarcts that paradoxically expand during ventricular systole. Therefore, the analysis of the onset of global (rather than regional) myocardial deformation may provide more accurate means for defining onset of cardiac systole. Sensors capable of deriving such global information include but are not limited to an accelerometer, CMES, or multipolar electrodes that acquire global impedance data. In one example, the onset of global cardiac systole can be identified by time of onset of positive global dZ/dt or peak global dZ'/dt (Z"), the latter of which will be used for illustrative purposes in this disclosure. Once the relative time of S1 and Z" are identified (t Z"–t S1), the timing difference between these two events, delta t S1 Z", can be calculated and evaluated as changes in AV timing are made.

A lower or even negative value of t S1 Z" will be found when atrial systole is truncated, as the mitral valve remains open even after aortic valve opening. A greater value will be found as the AV delay is too prolonged, where mitral valve closure is followed by a prolonged isovolumetric ventricular contraction before aortic valve opening. In one embodiment, the programmed AV timing is optimized to at S1 Z" value just greater than 0, to achieve aortic valve opening immediately after mitral valve closure. The t S1 Z" value may be a fixed number or may be calculated based upon one or more other factors, including but not limited to mitral inflow, stroke volume (e.g. AOVTI), intraventricular dyssynchrony. Optimization of t S1 Z" may be also achieved using the algorithms described herein (e.g. MOM, using R-LV delay, LV-LV delay, and/or RA to LA delay) or other algorithms known to those with skill in the art. In some embodiments, the fixed or calculated t S1 Z" value is in the range of about 70 msec to about 300 msec. In other embodiments, delta t S1 Z" is in the range of about 100 msec to about 200 msec.

Alternatively, a diastolic mechanical index, DMI, based upon the quotient of t S1 (numerator) and t Z" (denominator), can be analyzed and when the AV interval corresponding to a value of t S1 Z" just greater than unity, sz+, is found, this AV interval is selected. The target value of sz+ can be assumed to be equal to a value of one, or in a preferred embodiment, sz+ is chosen based on some previously derived extrinsic (e.g. echocardiographic data) or intrinsic (e.g. peak Z, SLI) measurement of systolic and/or diastolic cardiac performance. Use of an interface between echocardiography equipment and device/device programmer as described in U.S. Pat. No. 7,065,400, may be used to derive the desired baseline value for sz+.

In more preferred embodiments, the optimization of AV timing is performed in conjunction with the optimization of other cardiac timing intervals to account for the interrelationships therebetween. For example, changes in AV timing may exacerbate right-left dysynchrony. Similarly, changes in VV timing may affect optimal atrial-ventricular function. To maximize the benefits of AV timing optimization, a dual chamber or CRT device may be configured to perform AV timing optimization, before, during and/or after RV to LV timing (or other multi-site interval timing) and is serially evaluated as changes in VV timing will affect atrial ventricular synchrony.

Figure 32:
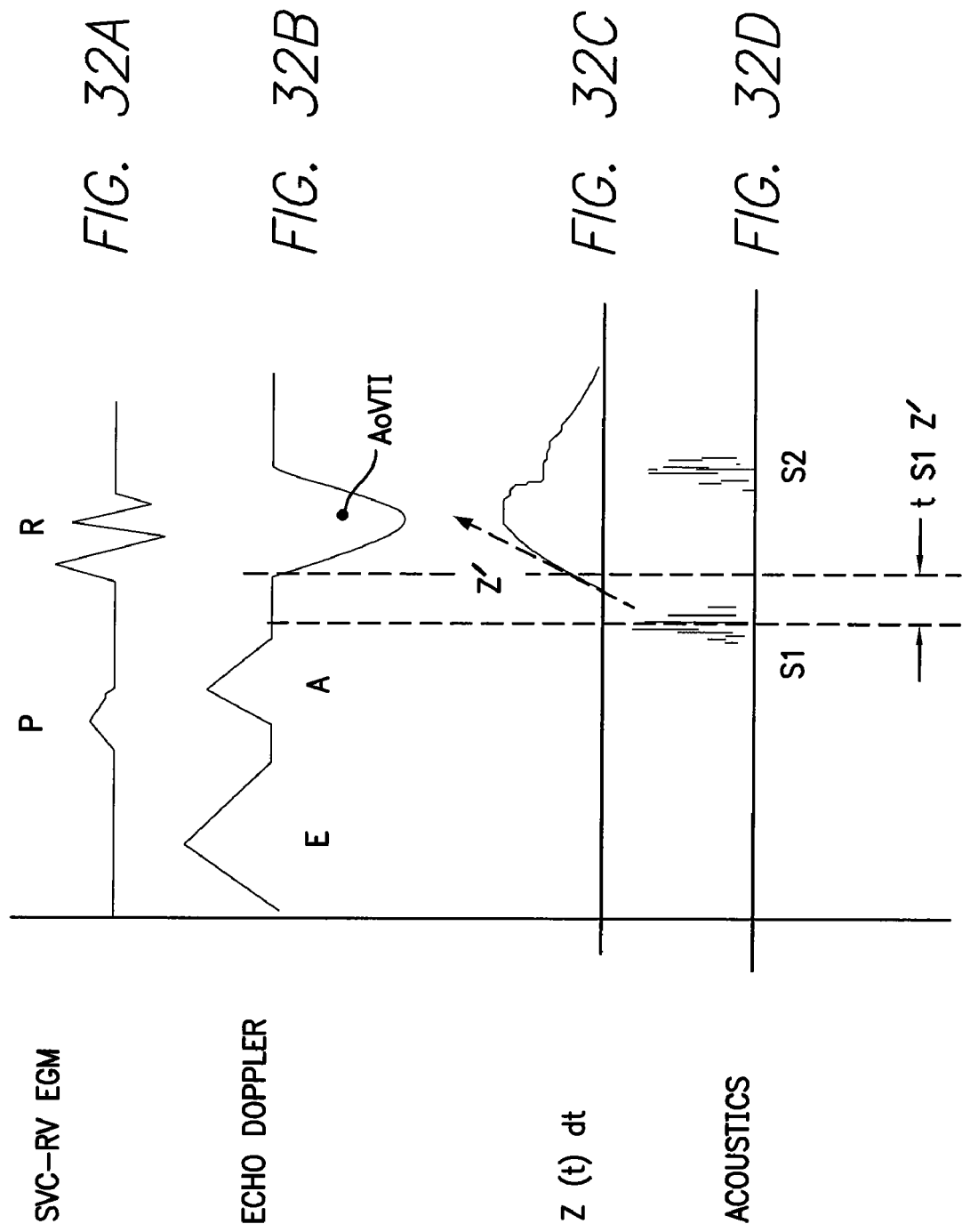
FIGS. 32a to 32d are a schematic depicting the temporal relationships between various sensor modalities.

Referring to FIGS. 32*a* to 32*d*, the general temporal relationships between an intracardiac electrogram, M-mode Doppler tracings of the aortic valve, global impedance waveforms and cardiac acoustic plots are depicted. FIG. 32*a* is a schematic representation of an intracardiac electrogram, IEGM, acquired from the SVC-RV coils. The IEGM is illustrative of atrial and ventricular electrical activity and demonstrates some of the fiducial points on the IEGM that may be used to construct a temporal framework demonstrating relationships of other sensor information as described in the parent application and herein. FIG. 32b is a schematic representation of M-mode pulsed wave Doppler taken at the left parasternal window. The E wave represents the opening and passive filling of the mitral valve, and the A wave is indicative of atrial systole and mitral valve closure. This data can be acquired at periodic intervals and displayed on the device programmer or alternate monitor as part of a Vital Monitoring System. Referring to FIG. 32c, the start of mechanical systole may be identified as the maximal slope of positive increase in dynamic impedance, Z". This corresponds to time of onset of aortic outflow, AoVTI, illustrated in FIG. 32b. In FIG. 32d, the time of mitral valve closure and the time of aortic valve closure, AoVc, may be identified by the S1 and S2 acoustic sounds, respectively. FIGS. 32a to 32d demonstrate that the analysis of myocardial electrical activity may not accurately identify cardiac mechanical events, implantable alternatives to externally applied echocardiographic sensors may be used to assess the mechanical characteristics of cardiac function.

Figure 33:
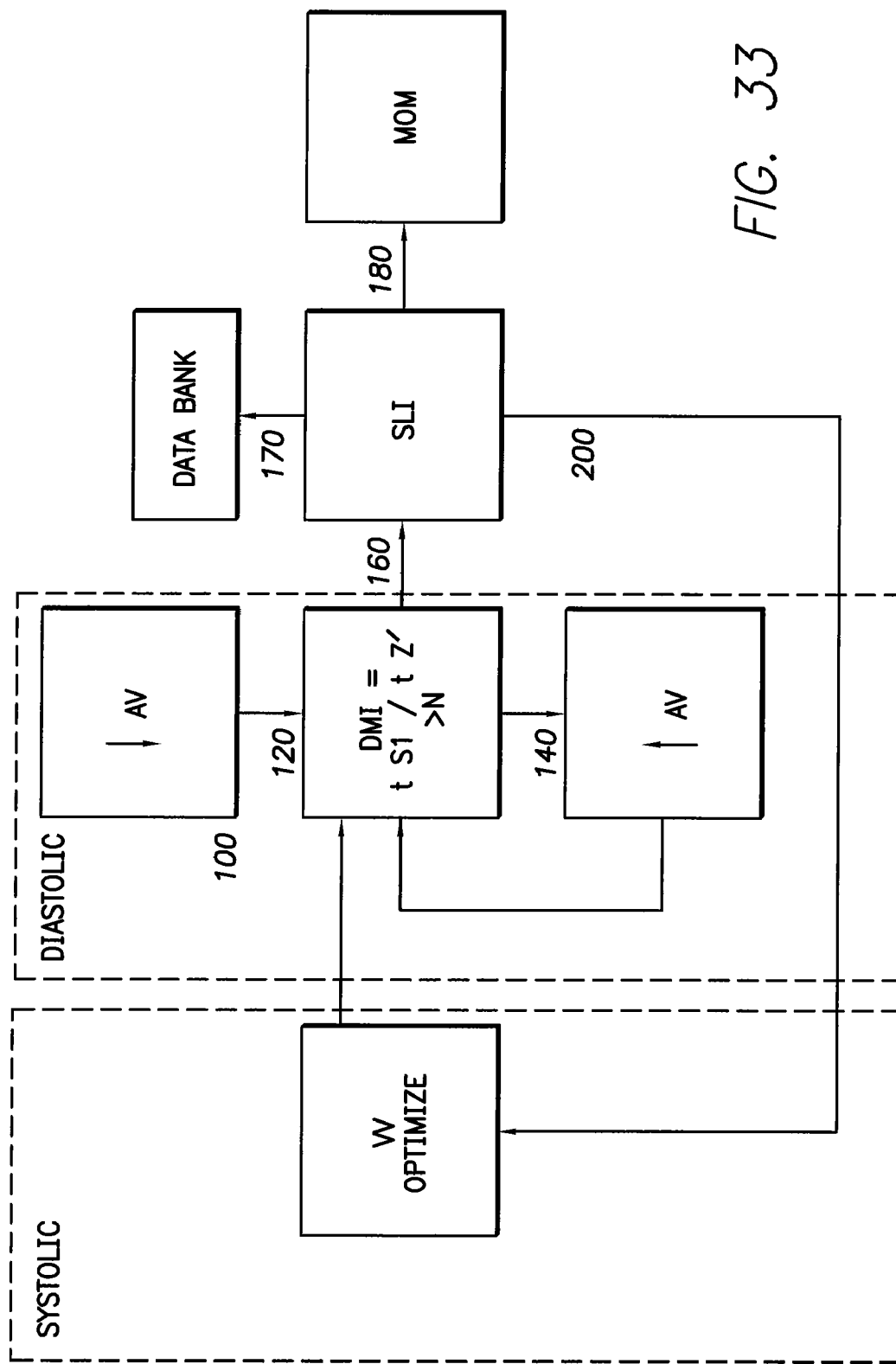
FIG. 33 is a flowchart of one embodiment of the invention for evaluating and adjusting the AV timing interval of a CRT device.

In FIG. 33, one embodiment of the invention comprises an algorithm whereby step 100 involves programming an initial narrow default AV delay (e.g. 50 msec). This will insure initial truncation of atrial systole, and provides a suboptimal baseline function level from which the optimization of the AV delay may begin. The diastolic mechanical index, DMI, is calculated at query box 120. If DMI is found to be greater than a specified value, N, the AV delay is increased. N can be unity or, as described above, a preset value determined during a prior evaluation. If DMI is too great a value then at step 140 the AV delay is increased by a specified time and query 120 is repeated. Once the optimal DMI is found, step 160 ensues and a measurement of cardiac performance (e.g. SLI) is made. Other measures of that assess the relative difference in mitral valve closure and aortic valve opening may be substituted for the DMI.

Measures of cardiac performance can be based on data generated from analysis of an impedance waveform as described herein, or alternate means. Cardiac performance data may be stored in a data bank, step 170, and can be referenced as needed. A range or set of optimal DMI values can be found that are within a preset range. The corresponding set of AV delays can be evaluated along with a number of W delays using the Matrix Optimization Method, MOM, at step 180. Alternatively, step 200 can proceed as part of any Systolic Mechanical Algorithm. The Systolic Mechanical Algorithm may comprise any of the variety of one or more methods described in the above referenced applications (e.g. ultrasonic interface) or otherwise described elsewhere. By way of example, VV optimization can be performed as to identify the parameters for achieving optimal SCP. Once the appropriate VV delay is identified and programmed, step 120 is repeated as to confirm appropriate diastolic properties still exist. This may be beneficial as changes in ventricular activation may affect AV synchrony as well. This algorithm can be repeated any number of times, for example, with a binary search. The Automatic Optimization Algorithm, AOA, as described previously, can confirm that the Systolic and Diastolic Mechanical Algorithms are functioning appropriately as part of an overseeing control system. Specific lock-outs for various interval timings (e.g. AV<50 msec or AV>PR interval) can be programmed as to prevent non-physiologic programming. Of note, though systolic and diastolic optimization is illustrated by example in this application, overlap evaluations of systolic and diastolic cardiac performance can be made at any point in the algorithm. By way of example, VV optimization can be performed using algorithms that derive the SLI, a measurement of the quotient of the integral of Z (t) dt, during systolic ejection phase and during diastole. One of skill in the art will understand that he various algorithm components may be rearranged in a different order to perform the same function.

In another embodiment, cardiac acoustic data can be evaluated for identification of diastolic MR. Diastolic MR may occur with prolonged AV delay that causes a reversal of the left atrium-to-left ventricle pressure gradient in late diastole. This in turn results in reduced ventricular filling and systolic function. Although the reversal of the pressure gradient is thought to promote mitral valve closure, the closure is often incomplete. Various means for detecting MR are described in the parent application. If MR is occurring before S1, diastolic MR is present. Detection of diastolic MR can prompt the system to increase or adjust the AV delay in similar fashion to step 120 and empirically assess the effect at step 160. Such an analysis can be complementary to analysis of DMI and also provide a form of functional redundancy in the system.

Prevention Of Positive Feedback

In the event an impedance signal is misinterpreted in a significant fashion as a result of an unexpected disturbance (e.g. not cardiac translation) the Vital Control System will not be able to pace with interval timing that falls outside a predetermined range of values. This range of values can be programmed using default intervals, based on echo interface or template data. The template data based on a specific individual's needs during a specified prior time frame will better serve the patient, unless some major change in the patient's underlying status occurs (infarction). The Automatic Optimization Algorithm is capable of detecting such a dramatic change acutely (with parameters of Global Cardiac Performance: dZ/dt, Z(peak), dZ'/dt, various integrals of Z(t) dt such as LCP, SCP) and on a more chronic basis. The parameters most applicable to chronic measurements are those incorporating measurements of thoracic fluid volume (pulmonary vascular congestion) such as Z offset, and GCRP (SLI×trans-pulmonic impedance). By these mechanisms a deleterious condition will be avoided.

The present disclosure is not intended to be limited to the embodiments shown and described herein, but is to be accorded the widest scope consistent with the principles and novel features disclosed herein. For all of the embodiments described above, the steps of the methods need not be performed sequentially.

I claim:

1. A method for adjusting the timing of a cardiac treatment device, comprising:
    providing an implantable device comprising a first programmable timing, a first implanted sensor system having a first sensory modality comprising intracardiac dynamic impedance, and a second implanted sensor system having a second sensory modality, different from the first sensory modality;
    detecting a first valve mechanical event time from the first implanted sensor system;
    detecting a second valve mechanical event time from the second implanted sensor system;
    generating a comparison value based upon the first valve mechanical event time and the second valve mechanical event time;
    comparing the comparison value to a target value; and
    adjusting the first programmable timing based upon the difference between the comparison value and the target value.

2. The method for adjusting the timing of a cardiac treatment device as in claim 1, wherein the second sensory modality is cardiac acoustics.

3. The method for adjusting the timing of a cardiac treatment device as in claim 1, wherein the second sensory modality is vascular pressure.

4. The method for adjusting the timing of a cardiac treatment device as in claim 1, wherein the first valve mechanical event time is aortic valve opening.

5. The method for adjusting the timing of a cardiac treatment device as in claim 1, wherein the second valve mechanical event time is mitral valve closure.

6. The method for adjusting the timing of a cardiac treatment device as in claim 1, wherein generating the comparison value comprises calculating a difference between the first valve mechanical event time and the second valve mechanical event time.

7. The method for adjusting the timing of a cardiac treatment device as in claim 1, wherein generating the comparison value comprises calculating a ratio of the first valve mechanical event time and the second valve mechanical event time.

8. The method for adjusting the timing of a cardiac treatment device as in claim 1, wherein the first programmable timing is an AV timing interval.

9. The method for adjusting the timing of a cardiac treatment device as in claim 1, wherein the target value is determined using echocardiography.

10. A method for adjusting the timing of a cardiac treatment device, comprising:
- providing an implantable device with a programmable timing setting;
- detecting a first valve mechanical event time using an acoustic sensor;
- detecting a second valve mechanical event time using an impedance sensor;
- generating a comparison value based upon the first valve mechanical event time and the second valve mechanical event time;
- comparing the comparison value to a target value; and
- adjusting the programmable timing of the implantable device based upon the difference between the comparison value and the target value.

* * * * *